United States Patent
Wurtz et al.

(10) Patent No.: US 11,530,183 B2
(45) Date of Patent: *Dec. 20, 2022

(54) PIPERIDINONE FORMYL PEPTIDE 2 RECEPTOR AND FORMYL PEPTIDE 1 RECEPTOR AGONISTS

(71) Applicant: BRISTOL-MYERS SQUIBB COMPANY, Princeton, NJ (US)

(72) Inventors: Nicholas R. Wurtz, Pennington, NJ (US); Pravin Sudhakar Shirude, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/898,889

(22) Filed: Jun. 11, 2020

(65) Prior Publication Data
US 2020/0299237 A1 Sep. 24, 2020

Related U.S. Application Data

(62) Division of application No. 15/776,933, filed as application No. PCT/US2016/065504 on Dec. 8, 2016, now Pat. No. 10,717,708.

(60) Provisional application No. 62/265,885, filed on Dec. 10, 2015.

(51) Int. Cl.
| | |
|---|---|
| *C07D 211/76* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 405/10* | (2006.01) |
| *C07D 405/12* | (2006.01) |
| *C07D 409/10* | (2006.01) |
| *C07D 413/10* | (2006.01) |
| *C07D 413/12* | (2006.01) |
| *C07D 417/12* | (2006.01) |

(52) U.S. Cl.
CPC .......... *C07D 211/76* (2013.01); *C07D 401/04* (2013.01); *C07D 401/10* (2013.01); *C07D 401/12* (2013.01); *C07D 401/14* (2013.01); *C07D 405/10* (2013.01); *C07D 405/12* (2013.01); *C07D 409/10* (2013.01); *C07D 413/10* (2013.01); *C07D 413/12* (2013.01); *C07D 417/12* (2013.01)

(58) Field of Classification Search
CPC .................................................. C07D 211/76
See application file for complete search history.

(56) References Cited

U.S. PATENT DOCUMENTS

| 9,822,069 | B2 | 11/2017 | Takahashi et al. |
| 10,029,983 | B2 | 7/2018 | Takahashi et al. |
| 10,252,992 | B2 | 4/2019 | Takahashi et al. |
| 10,717,708 | B2 * | 7/2020 | Wurtz ........................ A61P 9/00 |
| 11,186,544 | B2 * | 11/2021 | Wurtz .................. C07D 409/10 |

FOREIGN PATENT DOCUMENTS

| WO | 2002060859 A2 | 8/2002 | |
| WO | 2006063113 A2 | 6/2006 | |
| WO | WO-2006063113 A2 * | 6/2006 | ........... C07C 275/30 |
| WO | 2016189876 A1 | 12/2016 | |
| WO | 2016189877 A1 | 12/2016 | |
| WO | 2017091496 A1 | 6/2017 | |
| WO | 2017100390 A1 | 6/2017 | |
| WO | 2018227058 A9 | 12/2018 | |
| WO | 2018227061 A1 | 12/2018 | |
| WO | 2018227065 A1 | 12/2018 | |
| WO | 2018227067 A1 | 12/2018 | |

OTHER PUBLICATIONS

Parkesh et al., "Design of a Bioactive Small Molecule that Targets the Myotonic Dystropy Type 1 RNA via an RNA Motif-Ligand Database and Chemical Similarity Searching", JACS, vol. 134, pp. 4731-4742 (2012).

* cited by examiner

*Primary Examiner* — John S Kenyon
*Assistant Examiner* — Gillian A Hutter
(74) *Attorney, Agent, or Firm* — Hong Liu

(57) ABSTRACT

The disclosure relates to compounds of formula I, which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, chronic obstructive pulmonary disease (COPD), and related diseases.

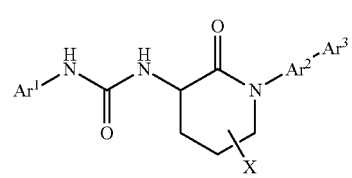

I

12 Claims, No Drawings

PIPERIDINONE FORMYL PEPTIDE 2 RECEPTOR AND FORMYL PEPTIDE 1 RECEPTOR AGONISTS

CROSS-REFERENCE TO RELATED APPLICATION

This application is a Divisional of U.S. patent application Ser. No. 15/776,933, filed May 17, 2018, now allowed, which is the 371 National Stage of International Application No. PCT/US2016/065504, filed Dec. 8, 2016, which claims priority to U.S. Provisional Patent Application U.S. Ser. No. 62/265,885, filed Dec. 10, 2015, hereby incorporated by reference in their entireties.

BACKGROUND OF THE INVENTION

The present invention relates to novel piperidinone compounds, which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to a small group of seven-transmembrane domain, G protein-coupled receptors that are expressed mainly by mammalian phagocytic leukocytes and are known to be important in host defense and inflammation. FPR2 shares significant sequence homology with FPR1 and FPR3. Collectively, these receptors bind a number of structurally diverse agonists, including N-formyl and nonformyl peptides which act as chemo attractants and activate phagocytes. The endogenous peptide Annexin A1 and its N-terminal fragments also bind human FPR1 and FPR2. Importantly, eicosanoid lipoxin A4, which belongs to a class of small pro-resolution mediators (SPMs), has been identified as a specific agonist for FPR2 (Ye R D., et al., Pharmacol. Rev., 2009, 61, 119-61).

Endogenous FPR2 pro-resolution ligands, such as lipoxin $A_4$ and Annexin A1 bind to the receptor triggering a wide array of cytoplasmatic cascades such as Gi coupling, $Ca^{2+}$ mobilization and β-arrestin recruitment. Activation of FPR2 by lipoxin $A_4$ modifies the effects of peptidic agonists, such as serum amyloid A (SAA), and has alternative effects on phosphorylation pathways depending on the cell type. Lipoxins regulate components of both innate and adaptive immune systems including neutrophils, macrophages, T-, and B-cells. In neutrophils, lipoxins modulate movement, cytotoxicity and life span. In macrophages, lipoxins prevent apoptosis and enhance efferocytosis. In most inflammatory cells, lipoxins also down-regulate expression of several pro-inflammatory cytokines, such as IL-6, IL-1β and IL-8 as well as up-regulate expression of anti-inflammatory cytokine IL-10 (Chandrasekharan J A, Sharma-Walia N, J. Inflamm. Res., 2015, 8, 181-92). The primary effects of lipoxin on neutrophils and macrophages are termination of inflammation and initiation of resolution of inflammation. The latter is primarily responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive loss of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 receptor with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

DESCRIPTION OF THE INVENTION

The invention encompasses compounds of formula I, which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of formula I

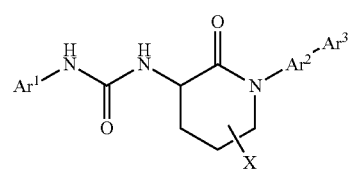

where:

$Ar^1$ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl, and is substituted with 1-3 substituents selected from cyano, halo, alkyl, haloalkyl, alkoxy, haloalkoxy, alkylthio, and $SO_2R^6$;

$Ar^2$ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;

$Ar^3$ is aryl or heteroaryl, and is substituted with 0-3 substituents selected from cyano, halo, alkyl, haloalkyl, hydroxyalkyl, alkoxyalkyl, $(NR^1R^2)$alkyl, $(CO_2R^3)$alkyl, $(CONR^4R^5)$alkyl, $(SO_2R^6)$alkyl, hydroxy, alkoxy, haloalkoxy, cycloalkoxy, $NR^1R^2$, $CO_2R^3$, $CONR^4R^5$, $SO_2R^6$, oxo, aryl, and heteroaryl;

$R^1$ is hydrogen, alkyl, alkylcarbonyl, alkylsulfonyl, or haloalkylsulfonyl;

$R^2$ is hydrogen or alkyl;

or $NR^1R^2$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and $R^3$ is alkyl or haloalkyl;

$R^4$ is hydrogen, alkyl, or $(R^7R^8N)$alkyl;

$R^5$ is hydrogen or alkyl;

or $NR^4R^5$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;

$R^6$ is alkyl or $R^7R^8N$;

$R^7$ is hydrogen or alkyl;

$R^8$ is hydrogen or alkyl;

or $NR^7R^8$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and X is hydrogen, halo, hydroxy, or alkoxy;

or a pharmaceutically acceptable salt thereof.

Another aspect of the invention is a compound of formula I where:

$Ar^1$ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl, and is substituted with 1-3 substituents selected from cyano, halo, alkyl, haloalkyl, alkoxy, haloalkoxy, alkylthio, and $SO_2R^6$;

$Ar^2$ is phenyl or pyridinyl substituted with 0-3 substituents selected from cyano, halo, alkyl, haloalkyl, alkoxy, and haloalkoxy;

$Ar^3$ is phenyl, pyridinyl, pyridazinyl, pyrimidinyl, pyrazinyl, pyridinonyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl and is substituted with 0-3 substituents selected from cyano, halo, alkyl, haloalkyl, hydroxyalkyl, alkoxyalkyl, $(NR^1R^2)$alkyl, hydroxy, alkoxy, haloalkoxy, cycloalkoxy, $NR^1R^2$, $CO_2R^3$, $CONR^4R^5$, and $SO_2R^6$;

$R^1$ is hydrogen, alkyl, alkylcarbonyl, alkylsulfonyl, or haloalkylsulfonyl;

$R^2$ is hydrogen or alkyl;

or $NR^1R^2$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;

$R^3$ is hydrogen or alkyl;

$R^4$ is hydrogen, alkyl, or $(R^7R^8N)$alkyl;

$R^5$ is hydrogen or alkyl;

or $NR^4R^5$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;

$R^6$ is alkyl or $R^7R^8N$;

$R^7$ is hydrogen or alkyl;

$R^8$ is hydrogen or alkyl;

or $NR^7R^8$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and X is hydrogen, halo, hydroxy, or alkoxy;

or a pharmaceutically acceptable salt thereof.

Another aspect of the invention is a compound of formula I where $Ar^1$ is phenyl, pyridinyl, pyridazinyl, thiazolyl, or benzodioxoyl and is substituted with 1-3 substituents selected from cyano, halo, alkyl, haloalkyl, alkoxy, haloalkoxy, and alkylthio; $Ar^2$ is phenyl or pyridinyl and is substituted with 0-3 substituents selected from cyano and halo; $Ar^3$ is phenyl, pyridinyl, pyrimidinyl, pyridinonyl, thienyl, pyrazolyl, isoxazolyl, benzodioxoyl, and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

Another aspect of the invention is a compound of formula I where $Ar^1$ is phenyl or pyridinyl and is substituted with 1-3 substituents selected from halo, alkyl, haloalkyl, alkoxy, haloalkoxy or alkylthio.

Another aspect of the invention is a compound of formula I where $Ar^1$ is phenyl or pyridinyl and is -1,4-substituted with 1 halo, alkyl, haloalkyl, alkoxy, haloalkoxy or alkylthio substituent with respect to the nitrogen attached to $Ar^1$ and also substituted with 0-2 fluoro substituents.

Another aspect of the invention is a compound of formula I where $Ar^2$ is phenyl or pyridinyl and is substituted with 0-3 substituents selected from cyano, halo, alkyl, haloalkyl, alkoxy, and haloalkoxy.

Another aspect of the invention is a compound of formula I where $Ar^2$ is -1,4-substituted with respect to the nitrogen and the $Ar^3$ to which it is attached.

Another aspect of the invention is a compound of formula I where $Ar^2$ is phenyl or pyridinyl and is -1,4-substituted with respect to the nitrogen and the $Ar^3$ to which it is attached and is substituted with 0-3 substituents selected from cyano, halo, alkyl, haloalkyl, alkoxy, and haloalkoxy.

Another aspect of the invention is a compound of formula I where $Ar^2$ is phenyl or pyridinyl and is -1,4-substituted with respect to the nitrogen and the $Ar^3$ to which it is attached and is substituted with 0-3 substituents selected from cyano and halo.

Another aspect of the invention is a compound of formula I where $Ar^3$ is phenyl, pyridinyl, pyrimidinyl, pyridinonyl, thienyl, pyrazolyl, isoxazolyl, benzodioxoyl, and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

Another aspect of the invention is a compound of formula I where $Ar^3$ is phenyl, pyridinyl, pyrimidinyl, pyridinonyl, thienyl, pyrazolyl, isoxazolyl, benzodioxoyl, and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

Another aspect of the invention is a compound of formula I where $Ar^3$ is phenyl or pyridinyl and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

Another aspect of the invention is a compound of formula I where X is hydrogen.

Another aspect of the invention is a compound of formula I where X is halo or hydroxy.

For a compound of Formula I, the scope of any instance of a variable substituent, including $R^1$, $R^2$, $R^3$, $R^4$, $R^5$, $R^6$, $R^7$, $R^8$, X, $Ar^1$, $Ar^2$, and $Ar^3$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo "Aryl" means a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

Heteroaryl includes N-substituted pyridinonyl:

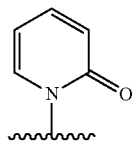 [SMILES: *n1ccccc1=O]

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms including the structure below with the indicated carbon. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

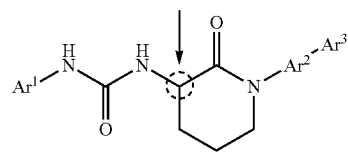

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, $Ca^{2+}$ mobilization and transcription. The family interacts with a diverse set of ligands that includes proteins, polypeptides and fatty acid metabolites which activate both pro-inflammatory and pro-resolution downstream responses.

The FPR2 receptor binds multiple ligands to invoke both inflammatory and anti-inflammatory responses. Inflammation mediator release by FPR2 has been reported to be promoted by endogenous protein ligands such as Serum amyloid A (SAA) and Amyloid β (1-42), whereas resolution of inflammation is induced by ligands that include arachidonic acid metabolites, lipoxin A4 (LXA4) and Epi-lipoxin (ATL), and a docosahexenoic acid metabolite, resolvin D1 (RvD1). The pro-resolving fatty acid metabolites mediate inhibition and resolution of inflammation through the FPR2 receptor by stimulating phagocytosis of apototic neutrophils by macrophages. Removal of the apototic neutrophils induce the release of cytokines that activate pro-resolution pathways.

The FPR1 receptor was originally isolated as a high affinity receptor for N-Formylmethionine containing peptides, such as N-Formylmethionine-leucyl-phenylalanine (FMLP). The protein directs mammalian phagocytic and blood leukocyte cells to sites of invading pathogens or inflamed tissues and activates these cells to kill pathogens or to remove cellular debris.

FPR2 and FPR1 Cyclic Adenosine Monophosphate (cAMP) Assays. A mixture of forskolin (5 μM final for FPR2 or 10 μM final for FPR1) and IBMX (200 μM final) were added to 384-well Proxiplates (Perkin-Elmer) pre-dotted with test compounds in DMSO (1% final) at final concentrations in the range of 0.020 nM to 100 µM. Chinese Hamster Ovary cells (CHO) overexpressing human FPR1 or human FPR2 receptors were cultured in F-12 (Ham's) medium supplemented with 10% qualified FBS, 250 µg/ml zeocin and 300 µg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 µM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. A range of $IC_{50}$ values of ≤1 µM (1000 nM) in one of the assays was observed. Table 1 below lists $EC_{50}$ values in the FPR2 and FPR1 cAMP assays measured for the following examples.

TABLE 1

| Example | hFPR2 cAMP2 EC50 (uM) | hFPR1 cAMP EC50 (uM) |
|---|---|---|
| 15 | 0.0084 | 0.20 |
| 16 | 0.0093 | 0.39 |
| 17 | 0.010 | 0.17 |
| 26 | 0.38 | 0.21 |
| 27 | 0.40 | 0.95 |
| 28 | 0.56 | 1.2 |
| 36 | 0.0097 | 0.28 |
| 47 | 0.33 | 1.6 |
| 48 | 0.56 | 0.93 |
| 49 | 0.85 | 2.1 |
| 58 | 0.0092 | 0.28 |
| 66 | 0.00032 | 0.10 |
| 76 | 0.00081 | 0.010 |
| 77 | 0.00068 | 0.0088 |
| 78 | 0.00089 | 0.042 |
| 82 | 0.011 | 0.014 |
| 86 | 0.00014 | 0.032 |
| 125 | 0.0090 | 0.33 |
| 129 | 0.0094 | 0.17 |
| 139 | 0.010 | 0.15 |
| 145 | 0.00036 | 0.015 |
| 166 | 0.0080 | 0.33 |
| 174 | 0.45 | 0.90 |
| 175 | 0.52 | 2.6 |
| 176 | 0.78 | 1.2 |
| 177 | 0.84 | 1.7 |
| 183 | 0.00046 | 0.00056 |
| 184 | 0.0081 | 1.5 |
| 188 | 0.00013 | 0.025 |
| 197 | 0.00076 | 0.22 |
| 199 | 0.00028 | 0.14 |

The following Examples were tested in the hFPR2 Assay described above and found having hFPR2 agonist activity with $EC_{50}$ values of ≤0.005 µM (5 nM): 1, 4, 5, 6, 7, 8, 9, 10, 11, 12, 29, 30, 31, 33, 51, 54, 56, 57, 61, 67, 68, 69, 70, 72, 79, 80, 81, 88, 91, 93, 98, 105, 106, 107, 108, 109, 111, 112, 113, 115, 116, 118, 121, 122, 133, 136, 137, 138, 141, 143, 146, 150, 151, 152, 154, 155, 163, 164, 165, 168, 171, 172, 173, 182, 186, 187, 190, 191, 194, 196, 202, 206, 207, and 210.

The following Examples were tested in the hFPR2 Assay described above and found having hFPR2 agonist activity with $EC_{50}$ values between 0.005 µM and 0.040 µM: 2, 13, 14, 18, 19, 20, 32, 34, 35, 37, 38, 39, 52, 55, 59, 63, 64, 71, 73, 74, 83, 84, 85, 89, 92, 96, 97, 102, 103, 104, 110, 114, 119, 120, 123, 124, 128, 131, 132, 135, 140, 142, 149, 156, 158, 167, 169, 178, 185, 192, 193, 195, 198, 200, 201, 203, 204, 205, 208, and 209.

The following Examples were tested in the hFPR2 Assay described above and found having hFPR2 agonist activity with $EC_{50}$ values between 0.04 µM and 1 µM: 3, 21, 22, 23, 24, 25, 40, 41, 42, 43, 44, 45, 46, 50, 53, 60, 62, 65, 75, 87, 90, 94, 95, 99, 100, 101, 117, 126, 127, 130, 134, 144, 147, 148, 157, 159, 160, 161, 162, 170, 179, 180, 181, and 189.

Pharmaceutical Compositions and Methods of Use

The compounds of the present invention may be administered to mammals, preferably humans, for the treatment of a variety of conditions and disorders including atherosclerosis, heart failure, lung diseases including asthma, COPD, and cystic fibrosis; neuroinflammatory diseases including multiple sclerosis, Alzheimer's disease, and stroke; and chronic inflammatory diseases such as inflammatory bowel disease, rheumatoid arthritis, psoriasis, sepsis, and kidney fibrosis.

Unless otherwise specified, the following terms have the stated meanings. The term "subject" refers to any human or other mammalian species that could potentially benefit from treatment with a FPR2 and/or FPR1 agonist as understood by practioners in this field. Some subjects include human beings of any age with risk factors for cardiovascular disease. Common risk factors include age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). The term "patient" means a person suitable for therapy as determined by practitioners in the field. "Treating" or "treatment" cover the treatment of a patient or subject as understood by practitioners in this field. "Preventing" or "prevention" cover the preventive treatment (i.e., prophylaxis and/or risk reduction) of a subclinical disease-state in a patient or subject aimed at reducing the probability of the occurrence of a clinical disease-state as understood by practitioners in this field. Patients are selected for preventative therapy based on factors that are known to increase risk of suffering a clinical disease state compared to the general population. "Therapeutically effective amount" means an amount of a compound that is effective as understood by practitioners in this field.

Another aspect of the invention are pharmaceutical compositions comprising a therapeutically effective amount of a compound of formula I in combination with a pharmaceutical carrier.

Another aspect of the invention are pharmaceutical compositions comprising a therapeutically effective amount of a compound of formula I in combination with at least one other therapeutic agent and a pharmaceutical carrier.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Another aspect of the invention is a method for treating heart disease comprising administering a therapeutically effective amount of a compound of formula I to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

Another aspect of the invention is a method for treating heart disease wherein the treatment is post myocardial infarction.

Another aspect of the invention is a method for treating heart disease comprising administering a therapeutically effective amount of a compound of formula I to a patient in conjuction with other therapeutic agents.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freezedrying and sealing. For use, the contents of the vial are mixed with 2 mL of physiological saline, to produce an injectable preparation.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with at least one of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention may be employed in combination with at least one of the following therapeutic agents in treating atherosclerosis: anti-hyperlipidemic agents, plasma HDL-raising agents, anti-hyperchol esterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination at least one of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The compounds of the invention may be used in combination with at least one of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with at least one of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries. The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product. The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached. The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemistry Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| Ac | Acetic |
|---|---|
| AcOH | acetic acid |
| ACN (or MeCN) | acetonitrile |
| APF | aminophenyl fluorescein |
| BINAP | 2,2'-bis(diphenylphosphino)-1,1'-binaphthyl |
| BISPIN | Bis(pinacolato)diboron |
| Bn | benzyl |

-continued

| Boc | tert-butyl carbonyl |
|---|---|
| Boc$_2$O | Di-tert-butyl dicarbonate |
| Bu | butyl |
| dba (Pd$_2$(dba)$_3$) | dibenzylideneacetone |
| CMBP | cyanomethylenetributylphosphorane |
| DCM | dichloromethane |
| DEAD | diethyl azodicarboxylate |
| DIAD | diisopropyl azodicarboxylate |
| Diamide | N,N,N',N'-Tetramethylazodicarbonamide (1,1'-Azobis(N,N-dimethylformamide)) |
| DIEA | diisopropylethylamine |
| DMAP | 4-dimethylaminopyridine |
| DME | Dimethoxyethane |
| DMF | dimethylformamide |
| DMSO | dimethyl sulfoxide |
| dppf | 1,1'-bis(diphenylphosphino)ferrocene |
| (DtBPF)PdCl$_2$ | 1.1'-bis(di-tert-butylphosphino)ferrocene palladium dichloride |
| Et | ethyl |
| EtOH | ethanol |
| EtOAc | ethyl acetate |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| i-Bu | isobutyl |
| i-Pr | isopropyl |
| LAH | lithium aluminum hydride |
| Me | methyl |
| MeOH | methanol |
| NMM | N-methylmorpholine |
| NMP | N-Methylpyrrolidone |
| PCC | pyridinium chlorochromate |
| Ph | phenyl |
| Pr | propyl |
| RT or rt | Room temperature |
| t-Bu | tert-butyl |
| TBDMS-Cl | t-butyldimethylchlorosilane |
| TBDMS | t-butyldimethylsilyl |
| TBDPS | t-butyldiphenylsilyl |
| TBDPS-Cl | t-butyldiphenylchlorosilane |
| TEA | Triethylamine |
| TFA | Trifluoroacetic acid |
| THF | tetrahydrofuran |
| TMAD | N,N,N',N'-Tetramethylazodicarbonamide (1,1'-Azobis(N,N-dimethylformamide)) |
| Ts | tosyl |

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)).

Compounds having the general Formula (I): wherein A, B and C are defined above as Ar$^1$, Ar$^2$ and Ar$^3$, respectively, can be prepared by the following one or more of the synthetic Schemes.

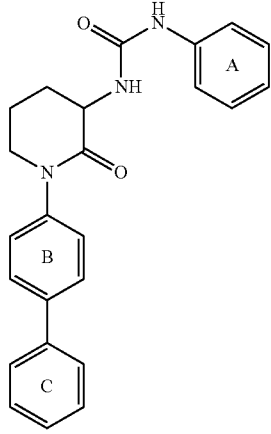

(I)

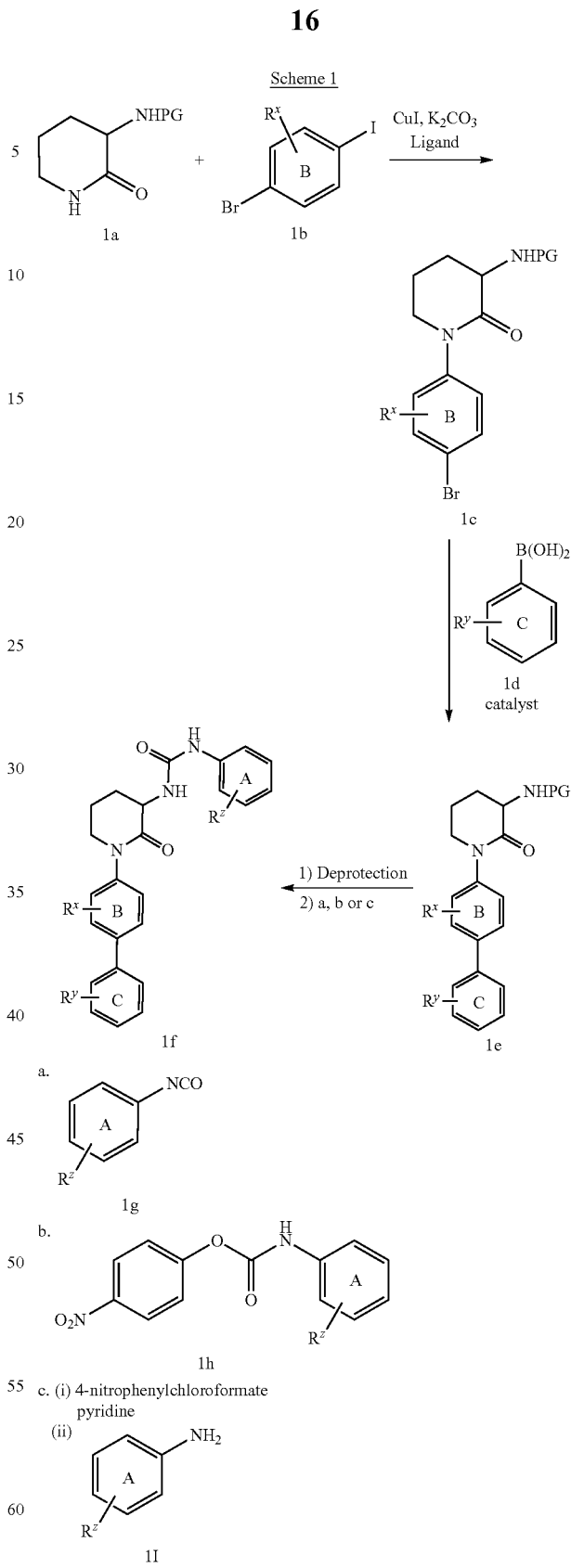

1-Arylpiperidinone compounds of this invention wherein rings A, B and C are substituted phenyl rings can be prepared by the general route shown in Scheme 1, starting from a suitably protected 3-aminopiperidin-2-one 1a, where PG is a protecting group such as Boc or Cbz. Copper-catalyzed coupling of 1a to a substituted iodobenzene 1b or other suitable halo aryl or heteroaryl compound in a suitable solvent such as butanol or dioxane, in the presence of a base such as potassium carbonate and a suitable ligand such as N,N'-dimethylethylenediamine, can afford 1-phenylpiperidinones 1c. Additional methods for this transformation include other variations of Ullmann, Goldberg, and Buchwald copper-catalyzed amidation or Buchwald Pd-catalyzed amidation depending on the nature of ring B, using methods known to one skilled in the art for these types of couplings (see for example Yin & Buchwald *Organic Lett.* 2000, 2, 1101; Klapers et al. *JACS,* 2001, 123, 7727; Klapars et al. *JACS,* 2002, 124, 7421; Yin & Buchwald *JACS.* 2002, 124, 6043; Kiyomor, Madoux & Buchwald, *Tet. Lett.,* 1999, 40, 2657). Subsequent palladium-catalyzed coupling of 1c to a suitably substituted phenyl boronic acid 1d, or analogous boronate or trifluoroborate reagent, can provide the biaryl compound 1e. Removal of the Boc or Cbz protecting group from 1e, followed by condensation of the resulting free amine with a suitably substituted phenyl isocyanate, 1g or 4-nitrophenyl phenylcarbamate 1h can provide ureas 1f. Suitable isocyanates or 4-nitrophenylcarbamates are either commercially available or can be readily obtained from the corresponding aniline by methods known to one skilled in the art. Alternately, the ureas 1f can be obtained by treatment of the deprotected 3-aminopiperidinone intermediate with 4-nitrophenylchloroformate to form the carbamate, followed by condensation with a appropriately substituted aniline 1j. It will also be recognized by one skilled in the art that additional compounds of this invention wherein rings A, B or C are heteroaryl rings, such as pyridine, pyrimidine, thiazole, etc., can also be prepared using the methods outlined in Scheme 1 by substituting the appropriate heteroaryl iodide or bromine for 1b, heteroarylboronic acid or boronate for 1d and heteroaryl amine, isocyanate or p-nitrophenylcarbamate for 1e.

Alternatively as described in Scheme 2, compounds of this invention can be prepared from intermediate 1c by first deprotecting the amine and forming the urea linkage to ring A using the conditions described above for the conversion of 1e to 1f to provide compounds 2a. Compound 2a can then be coupled with an appropriate boronic acid or boronate under Pd-catalysis conditions as shown in Scheme 1 for the transformation of 1c to 1e.

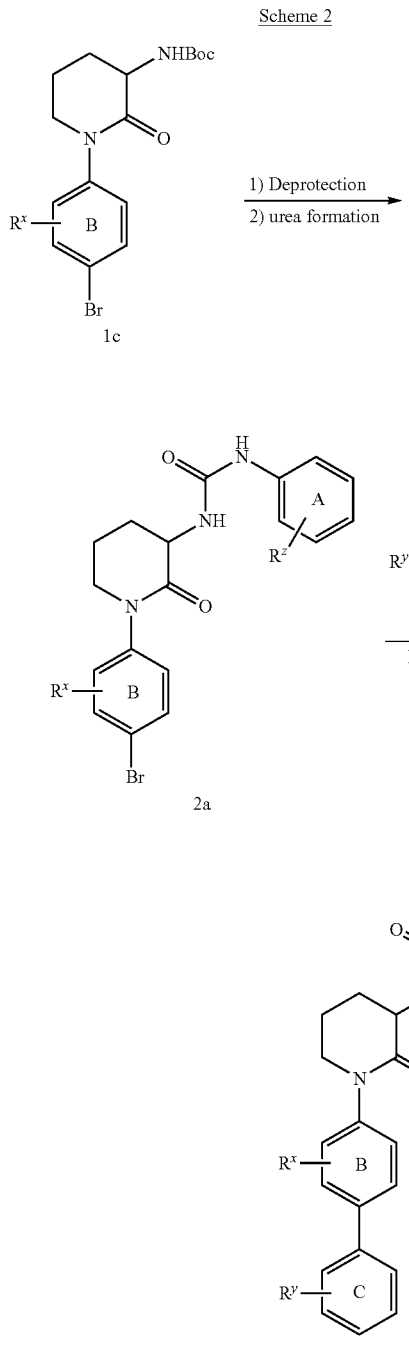

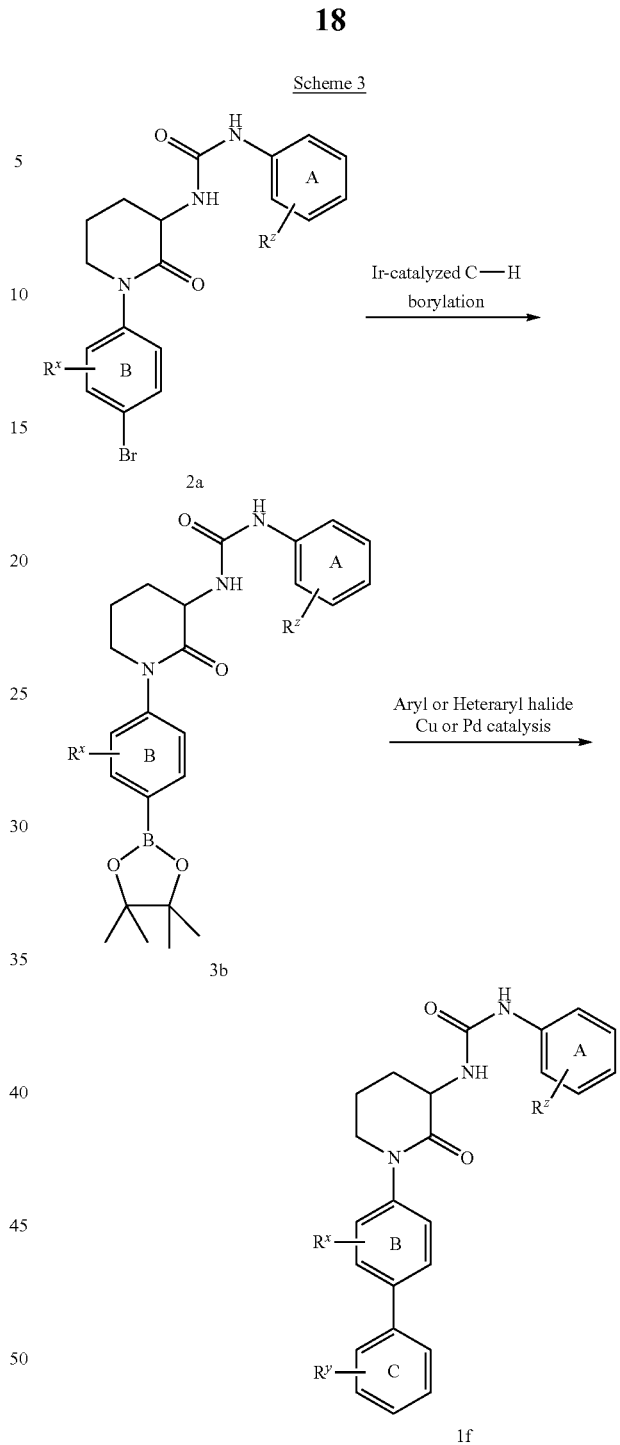

Additionally, compounds of this invention can be prepared from intermediate 2a by conversion to boronate 3b using iridium-catalyzed C—H borylation according to the method of Suzuki and Miyaura followed by coupling of the resulting pinacolatoboron species with aryl or heteroaryl halides using palladium or copper catalyzed processes to provide compounds 1f.

Other features of the invention will become apparent in the course of the following descriptions of exemplary embodiments that are given for illustration of the invention and are not intended to be limiting thereof.

The following methods were used in the exemplified Examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% ACN, 0.1% TFA) and Solvent B (5% water, 95% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$).

LC/MS Methods Employed in Characterization of Examples. Reverse phase analytical HPLC/MS was performed on a Waters Acquity system coupled with a Waters MICROMASS® ZQ Mass Spectrometer.

Method A: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 0.1% TFA, 95% water, 5% acetonitrile
Solvent B: 0.1% TFA, 5% water, 95% acetonitrile Method B: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 10 mM ammonium acetate, 95% water, 5% acetonitrile
Solvent B: 10 mM ammonium acetate, 5% water, 95% acetonitrile Analytical HPLC: Methods Employed in Characterization of Examples Products were analyzed by reverse phase analytical HPLC: carried out on a Shimadzu Analytical HPLC: system running Discovery VP software. RT=retention time.

Method A: SunFire C18 column (3.5 m C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method B: XBridge Phenyl column (3.5 m C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.

Method E: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-μminute hold at 100% B; Flow: 1.1 mL/min.

Method F: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method G: SunFire C18 column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method H: XBridge Phenyl column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method I: SunFire C18 column (3.5 m, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: XBridge Phenyl column (3.5 m, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K: SunFire C18 column (3.5 m, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: XBridge Phenyl column (3.5 am, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm Method M: SunFire C18 column (3.5 am, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method N: XBridge Phenyl column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

SFC and Chiral Purity Methods

Method I: Chiralpak AD-H, 250×4.6 mm, 5.0-μm particles; % CO2: 60%, % Co solvent: 40% {0.2% DEA IN IPA:A CN(1:1)}, Total Flow: 4.0 g/min, Back Pressure: 100 bars, Temperature: 25° C., UV: 218 nm.

Method II: Chiralpak OD-H, 250×4.6 mm, 5.0-μm particles; % CO2: 60%, % Co solvent: 40% {0.2% DEA IN IPA:A CN(1:1)}, Total Flow: 4.0 g/min, Back Pressure: 104 bars, Temperature: 24.9° C., UV: 287 nm.

Method III: Chiralpak OJ-H, 250×4.6 mm, 5.0-μm particles; % CO2: 60%, % Co-solvent: 30%(0.3% DEA in Methanol), Total Flow: 4.0 g/min, Back Pressure: 101 bars, Temperature: 23.6° C., UV: 272 nm.

Method IV: Chiralpak AS-H, 250×4.6 mm, 5.0-μm particles; % CO2: 60%, % Co-solvent: 40%(0.3% DEA in Methanol), Total Flow: 4.0 g/min, Back Pressure: 102 bars, Temperature: 25.4° C., UV: 272 nm.

Method V: Chiralcel OJ-H, 250×4.6 mm, 5.0-μm particles; % CO2: 60%, % Co-solvent: 40%(0.2% DEA in Methanol), Total Flow: 4.0 g/min, Back Pressure: 102 bars, Temperature: 24.6° C., UV: 272 nm.

Method VI: Luxcellulose-2, 250×4.6 mm, 5.0-μm particles; % CO2: 60%, % Co-solvent: 35%(0.2% DEA in Methanol), Total Flow: 3.0 g/min, Back Pressure: 101 bars, Temperature: 23.6° C., UV: 260 nm.

Method VII: Chiralcel AS-H, 250×4.6 mm, 5.0-μm particles; % CO2: 60%, % Co-solvent: 40%(0.2% DEA in Methanol), Total Flow: 4.0 g/min, Back Pressure: 101 bars, Temperature: 24.4° C., UV: 270 nm.

Method VIII: Chiralpak IC, 250×4.6 mm, 5.0-μm particles; % CO2: 60%, % Co-solvent: 40%(0.2% DEA in Methanol), Total Flow: 4.0 g/min, Back Pressure: 101 bars, Temperature: 24.4° C., UV: 270 nm.

Method IX: COLUMN: chiralpakF (250×4.6 mm), 5 micron, MOBILE PHASE: −0.2% DEA in ETHANOL, FLOW: 1.0 ml\min.

Method X: COLUMN: LUX AMYLOSE 2 (250×4.6 mm), 5 micron, MOBILE PHASE: 0.2% DEA in n-HEXANE:ETHANOL:5:95, FLOW:1.0 ml\min.

Method XI: COLUMN: CHIRALCEL OD-H (250×4.6 mm), 5 micron, MOBILE PHASE: −0.2% DEA in n-HEXANE:ETHANOL:70:30, FLOW:1.0 ml\min.

Method XII: COLUMN: CHIRAL PAK ID 250×4.6 mm), 5 micron, MOBILE PHASE: −0.1% DEA in METHANOL, FLOW: 1.0 ml\min.

NMR Employed in Characterization of Examples. $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Intermediate 1: (R)-1-(1-(4-bromophenyl)-2-oxopiperidin-3-yl)-3-(4-(trifluoromethyl)phenyl)urea

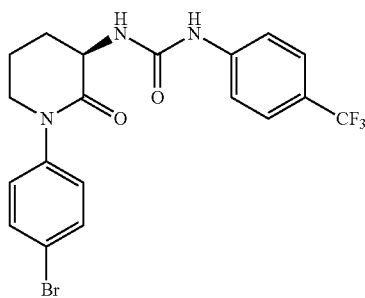 [SMILES: O=C(Nc1ccc(C(F)(F)F)cc1)N[C@@H]1CCCN(c2ccc(Br)cc2)C1=O]

Intermediate 1a: tert-butyl (R)-(1-(4-bromophenyl)-2-oxopiperidin-3-yl)carbamate

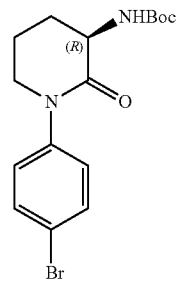

In a 1 L sealed tube, to a solution of (R)-tert-butyl (2-oxopiperidin-3-yl)carbamate (23 g, 110 mmol) in 1,4-dioxane (300 mL) was added 1,4-dibromobenzene (28 g, 120 mmol), potassium phosphate tribasic (34 g, 160 mmol), cuprous iodide (8.2 g, 43 mmol), N,N'-dimethylethylenediamine (4.7 ml, 43 mmol). The reaction mixture was purged with Argon for 10-15 minutes and then heated to 60° C. for overnight. The reaction mixture was diluted with ethyl acetate (250 mL) and washed with brine solution (200 mL). The organic layer was dried over $Na_2SO_4$ and concentrated to produce the crude product. The crude compound was purified through 330 gm Silica column and was eluted with ethylacetate:pet-ether (40:60) to achieve off white solids of tert-butyl (1-(4-bromophenyl)-2-oxopiperidin-3-yl)carbamate (20 gm). Chiral SFC analysis of the purified product showed ~10% epimerization. The compound was then purified via SFC to afford Intermediate 1a (15 gm, 40 mmol, 38% yield) as a white solid. MS(ESI) m/z: 369.0/371.0 (M+H). $^1$H NMR (400 MHz, $CDCl_3$): δ ppm 7.48 (d, J=4.8 Hz, 2H), 7.11 (d, J=4.8 Hz, 2H), 5.48 (br-s, 1H), 4.25-4.18 (m, 1H), 3.70-3.62 (m, 2H), 2.60-2.52 (m, 1H), 2.08-1.95 (m, 2H), 1.74-1.64 (m, 1H), 1.43 (s, 9H). $[\alpha]_D^{25}$ (c=0.1, MeOH): +30.0. Chiral Purity (SFC): 99.9%, retention time=4.15 min (time of Peak-01 (0.105%)=3.03 min & Retention time of Peak-02 (99.9%)=4.15 min; Co-Solvent: 0.2% DEA in Methanol; Column: Whelk-01 (R,R)(250×4.6) mm 5 u; Column Temperature: 24.5; Total Flow: 3; CO2 Flow Rate: 1.8; Co-Solvent Flow Rate: 1.2; Co-Solvent % 40; Back Pressure 100.)

Preparative SFC Conditions: Column/dimensions: Whelk (R,R) (250×30) mm, 5 u; $CO_2$%: 70%; Co-solvent %: 30% of (0.2% DEA in methanol); Total Flow: 120 g/min; Back Pressure: 100 bar; Temperature: 30° C.; UV: 240 nm. Retention time of Peak-01=3.20 min & Retention time of Peak-02=4.60 min;

Intermediate 1b: (R)-3-amino-1-(4-bromophenyl)piperidin-2-one hydrochloride

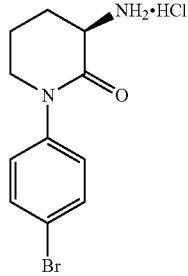

To a cooled solution of Intermediate 1a (400 mg, 1.1 mmol) in 1,4-dioxane (10 mL) was added 4N HCl in 1,4-dioxane (5.2 mL) and stirred at rt for two hours. The solvent was evaporated and the residue was dried under reduced pressure to obtain a gummy solid.

The solid was further triturated with diethyl ether (2×20 mL) and dried to afford Intermediate 1b (300 mg, 0.98 mmol, 91% yield) as a off white solid. MS(ESI) m/z: 271.0 (M+H). $^1$H NMR (400 MHz, DMSO-$d_6$): δ 8.36 (br. s., 3H), 7.65-7.60 (m, 2H), 7.32-7.26 (m, 2H), 4.06-3.99 (m, 1H), 3.77-3.68 (m, 1H), 3.64-3.58 (m, 1H), 2.28-2.24 (m, 1H), 2.06-1.96 (m, 2H), 1.96-1.85 (m, 1H).

Intermediate 1

To a cooled solution of Intermediate 1b (R)-3-amino-1-(4-bromophenyl)piperidin-2-one (300 mg, 1.1 mmol) in THF (10 mL) were added TEA (0.47 mL, 3.3 mmol) and 1-isocyanato-4-(trifluoromethyl)benzene (210 mg, 1.1 mmol) and the reaction mixture was stirred at rt for 15 hours. The mixture was concentrated under reduced pressure to get the crude compound which was triturated with diethyl ether to afford Intermediate 1 (450 mg, 0.99 mmol, 88% yield) as a light brown solid. MS(ESI) m/z: 458.0 (M+H). $^1$H NMR (400 MHz, DMSO-$d_6$): δ 9.28 (s, 1H), 7.62-7.55 (m, 6H), 7.31-7.26 (m, 2H), 6.71 (d, J=6.5 Hz, 1H), 4.37-4.23 (m, 1H), 3.75-3.59 (m, 2H), 2.29-2.25 (m, 1H), 2.03-1.93 (m, 2H), 1.87-1.75 (m, 1H).

Intermediate 2: (S)-1-(1-(4-bromophenyl)-2-oxopiperidin-3-yl)-3-(4-(trifluoromethyl)phenyl)urea

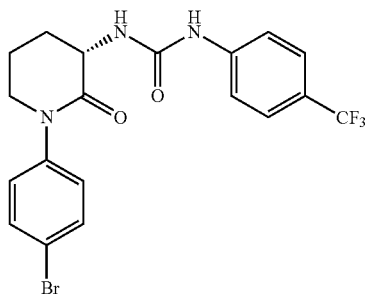 [SMILES: O=C(Nc1ccc(C(F)(F)F)cc1)N[C@H]1CCCN(c2ccc(Br)cc2)C1=O]

(S)-3-amino-1-(4-bromophenyl)piperidin-2-one was synthesized in an analogous way to Intermediate 1b. To a cooled solution of (S)-3-amino-1-(4-bromophenyl)piperidin-2-one hydrochloride (300 mg, 1.1 mmol) in THF (10 mL) were added TEA (0.39 mL, 2.8 mmol) and 1-isocyanato-4-(trifluoromethyl)benzene (210 mg, 1.1 mmol) and the reaction mixture was stirred at rt for 15 hours. The mixture was concentrated under reduced pressure to yield the crude compound which was triturated with diethyl ether to afford Intermediate 2 (300 mg, 0.66 mmol, 59% yield) as a off white solid. MS(ESI) m/z: 459.0 (M+H). $^1$H NMR (400 MHz, DMSO-$d_6$): δ 9.21 (s, 1H), 7.64-7.54 (m, 6H), 7.29 (d, J=9.0 Hz, 2H), 6.67 (d, J=7.0 Hz, 1H), 4.38-4.28 (m, 1H), 3.75-3.60 (m, 2H), 2.36-2.22 (m, 1H), 2.05-1.91 (m, 2H), 1.87-1.73 (m, 1H).

Intermediate 3: (R)-1-(1-(4-bromophenyl)-2-oxopiperidin-3-yl)-3-(4-chlorophenyl)urea

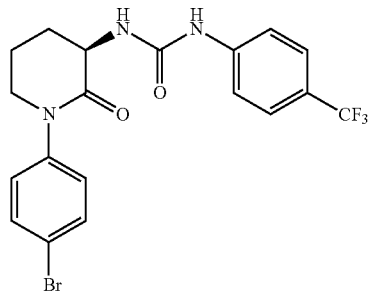 [SMILES: O=C(Nc1ccc(C(F)(F)F)cc1)N[C@@H]1CCCN(c2ccc(Br)cc2)C1=O]

To a cooled solution of (R)-3-amino-1-(4-bromophenyl)piperidin-2-one (350 mg, 1.3 mmol) in THF (10 mL) were added TEA (0.45 mL, 2.6 mmol) and 1-chloro-4-isocyanatobenzene (200 mg, 1.3 mmol) and the reaction mixture was stirred at RT for 15 hours. The mixture was concentrated under reduced pressure to give the crude product which was triturated with diethyl ether to afford Intermediate 3 (400 mg, 0.95 mmol, 72% yield) as a light brown solid. MS(ESI) m/z: 423.0 (M+H). $^1$H NMR (400 MHz, DMSO-$d_6$) δ 8.90 (s, 1H), 7.58 (d, J=9.0 Hz, 2H), 7.42 (d, J=8.5 Hz, 2H), 7.27 (dd, J=8.5, 6.0 Hz, 4H), 6.54 (d, J=6.5 Hz, 1H), 4.37-4.24 (m, 1H), 3.75-3.58 (m, 2H), 2.31-2.22 (m, 1H), 2.04-1.93 (m, 2H), 1.85-1.72 (m, 1H).

Intermediate 4: ((R)-1-(2-oxo-1-(4-(4,4,5,5-tetramethyl-1,3,2-dioxaborolan-2-yl)phenyl)piperidin-3-yl)-3-(4-(trifluoromethyl)phenyl)urea

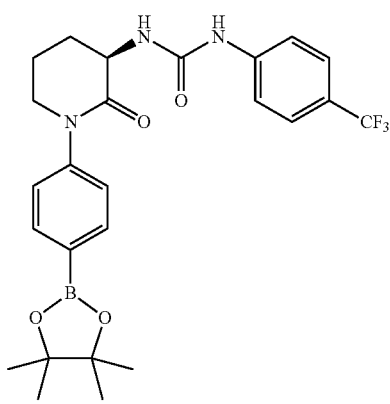 [SMILES: CC1(C)OB(c2ccc(N3CCC[C@@H](NC(=O)Nc4ccc(C(F)(F)F)cc4)C3=O)cc2)OC1(C)C]

To a solution of Intermediate 1 (1.0 g, 2.2 mmol) in 1,4-dioxane (10 mL) were added BISPIN (0.84 g, 3.3 mmol) and potassium acetate (0.43 g, 4.4 mmol). The reaction mixture was purged with nitrogen for 5 min and charged with Pd(dppf)Cl$_2$.DCM adduct (0.18 g, 0.22 mmol). The reaction mixture was again purged with nitrogen for 3 min and heated at 60° C. for 16 h. The reaction mixture was cooled, filtered through a celite pad, and washed with ethyl acetate (50 mL). The filtrate was concentrated under reduced pressure and the crude compound was purified by column chromatography to afford Intermediate 4 (0.70 g, 1.4 mmol, 64% yield) as a pale brown solid. MS(ESI) m/z: 504 (M+H); $^1$H NMR (400 MHz, DMSO-d$_6$) δ 9.2 (s, 1H), 7.73-7.65 (m, 2H), 7.63-7.53 (m, 4H), 7.36-7.28 (m, 2H), 6.71-6.63 (m, 1H), 4.40-4.30 (m, 1H), 3.78-3.61 (m, 2H), 2.36-2.24 (m, 1H), 2.04-1.93 (m, 2H), 1.86-1.73 (m, 1H), 1.29 (s, 12H).

Intermediate 5: (R)-1-(4-chlorophenyl)-3-(2-oxo-1-(4-(4,4,5,5-tetramethyl-1,3,2-dioxaborolan-2-yl)phenyl)piperidin-3-yl)urea

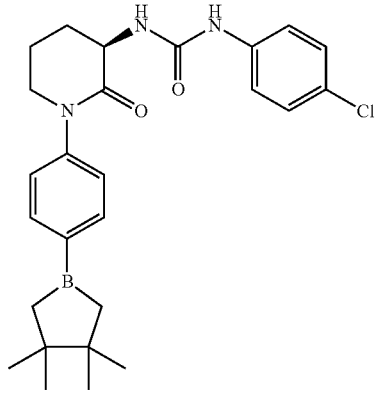 [SMILES: CC1(C)CB(c2ccc(N3CCC[C@@H](NC(=O)Nc4ccc(Cl)cc4)C3=O)cc2)CC1(C)C]

To a solution of Intermediate 3 (0.50 g, 1.2 mmol) in 1,4-dioxane (10 mL) were added BISPIN (0.45 g, 1.8 mmol) and potassium acetate (0.23 g, 2.4 mmol). The reaction mixture was purged with nitrogen for 5 min and charged with Pd(dppf)Cl$_2$.DCM adduct (0.097 g, 0.12 mmol). The reaction mixture was again purged with nitrogen for 3 min and heated at 60° C. for 16 h. The reaction mixture was cooled, filtered through a celite pad, and washed with ethyl acetate (50 mL×2). The filtrate was concentrated under reduced pressure and the crude compound was purified by column chromatography to afford Intermediate 5 (0.50 g, 1.1 mmol, 90% yield) as a pale brown solid. MS(ESI) m/z: 470.2 (M+H); $^1$H NMR (400 MHz, DMSO-d$_6$): δ 8.90 (s, 1H), 7.91 (s, 2H), 7.68 (d, J=8.5 Hz, 2H), 7.33 (d, J=8.5 Hz, 2H), 7.26 (d, J=9.0 Hz, 2H), 6.57-6.51 (m, 1H), 4.36-4.27 (m, 1H), 3.77-3.62 (m, 2H), 2.35-2.24 (m, 1H), 2.04-1.93 (m, 2H), 1.83-1.71 (m, 1H), 1.29 (s, 12H).

Intermediate 6: tert-butyl (R)-(1-(5-bromopyridin-2-yl)-2-oxopiperidin-3-yl)carbamate Intermediate 7: tert-butyl (S)-(1-(5-bromopyridin-2-yl)-2-oxopiperidin-3-yl)carbamate Intermediate 8: tert-butyl (R)-(1-(6-iodopyridin-3-yl)-2-oxopiperidin-3-yl)carbamate Intermediate 9: tert-butyl (S)-(1-(6-iodopyridin-3-yl)-2-oxopiperidin-3-yl)carbamate

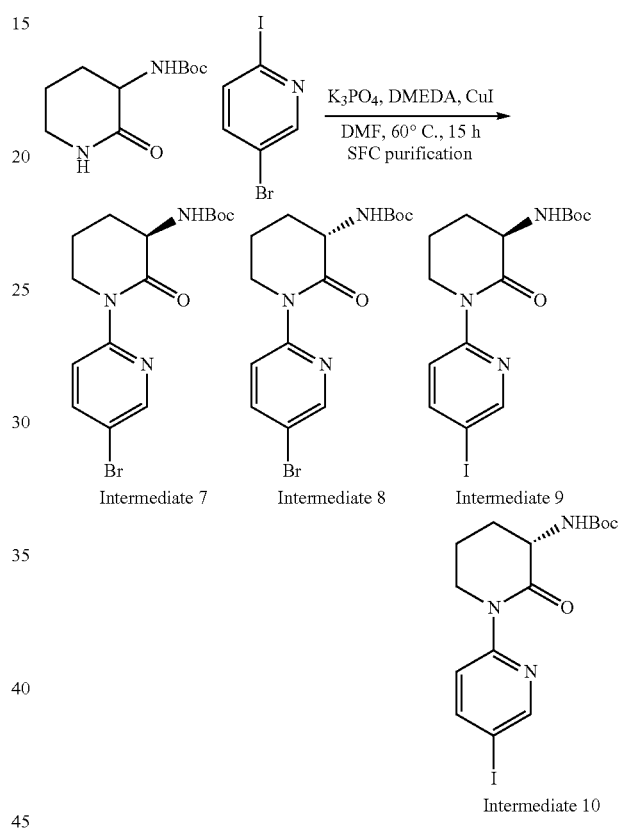

To a solution containing tert-butyl (2-oxopiperidin-3-yl)carbamate (4.0 g, 19 mmol) in dry DMF (10 mL) were added 5-bromo-2-iodopyridine (5.3 g, 19 mmol) and potassium phosphate, tribasic (7.9 g, 37 mmol). The reaction mixture was purged with nitrogen for 30 min and charged with copper(I) iodide (0.36 g, 1.9 mmol) and N,N'-dimethylethylenediamine (0.33 g, 3.7 mmol). The reaction mixture was again purged with nitrogen for 10 min and heated at 60° C. for 15 h. The reaction mixture was cooled, filtered through a celite pad, washed with ethyl acetate (50 mL) and the filtrate was concentrated under reduced pressure. The crude compound was purified by column chromatography to afford 2.3 g of a racemic mixture which was further subjected to enantiomeric separation using Supercritical fluid chromatography (SFC) (method I) to provide the Intermediates 7-10, as single enantiomers.

Intermediate 7 (1.5 g, 4.1 mmol, 22% yield). MS(ESI) m/z: 372 (M+H); $^1$H NMR (400 MHz, CDCl$_3$): δ 8.44 (dd, J=2.3, 0.8 Hz, 1H), 7.85-7.81 (m, 1H), 7.81-7.76 (m, 1H), 5.48 (br. s., 1H), 4.47-4.33 (m, 2H), 3.75-3.66 (m, 1H), 2.61-2.56 (m, 1H), 2.07-1.98 (m, 2H), 1.70-1.62 (m, 1H), 1.48 (s, 9H); The absolute stereochemistry of Intermediate 7 was confirmed by single molecule crystal structure.

Intermediate 8 (0.90 g, 2.4 mmol, 13% yield). MS(ESI) m/z: 372 (M+H); δ 8.44 (dd, J=2.3, 0.8 Hz, 1H), 7.85-7.81 (m, 1H), 7.81-7.76 (m, 1H), 5.48 (br. s., 1H), 4.47-4.33 (m, 2H), 3.75-3.66 (m, 1H), 2.61-2.56 (m, 1H), 2.07-1.98 (m, 2H), 1.70-1.62 (m, 1H), 1.48 (s, 9H).

Intermediate 9 (1.9 g, 4.6 mmol, 24% yield). MS(ESI) m/z: 418 (M+H); $^1$H NMR (400 MHz, CDCl$_3$): δ 8.59 (dd, J=2.3, 0.8 Hz, 1H), 7.95 (dd, J=8.8, 2.3 Hz, 1H), 7.75 (dd, J=8.8, 0.8 Hz, 1H), 5.49 (br. s., 1H), 4.47-4.33 (m, 2H), 3.73-3.66 (m, 1H), 2.63-2.53 (m, 1H), 2.07-1.98 (m, 2H), 1.70-1.60 (m, 1H), 1.48 (s, 9H).

Intermediate 10 (2.2 g, 5.3 mmol, 28% yield) MS(ESI) m/z: 418 (M+H); $^1$H NMR (400 MHz, CDCl$_3$): δ 8.59 (dd, J=2.3, 0.8 Hz, 1H), 7.95 (dd, J=8.8, 2.3 Hz, 1H), 7.75 (dd, J=8.8, 0.8 Hz, 1H), 5.49 (br. s., 1H), 4.47-4.33 (m, 2H), 3.73-3.66 (m, 1H), 2.63-2.53 (m, 1H), 2.07-1.98 (m, 2H), 1.70-1.60 (m, 1H), 1.48 (s, 9H).

Example 1. 1-(4-chlorophenyl)-3-(1-(3-fluoro-2'-(methylsulfonyl)-[1,1'-biphenyl]-4-yl)-2-oxopiperidin-3-yl)urea

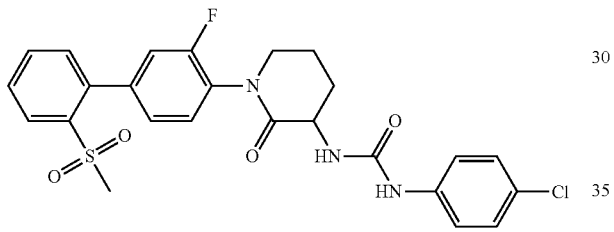

Example 1A. tert-butyl (1-(4-chloro-2-fluorophenyl)-2-oxopiperidin-3-yl)carbamate

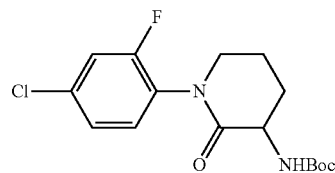 [SMILES: CC(C)(C)OC(=O)NC1CCCN(c2ccc(Cl)cc2F)C1=O]

A mixture of 4-chloro-2-fluoro-1-iodobenzene (5.3 g, 21 mmol), tert-butyl (2-oxopiperidin-3-yl)carbamate (2.0 g, 9.3 mmol), N,N'-dimethyl-1,2-ethanediamine (0.25 g, 2.8 mmol), CuI (0.89 g, 4.7 mmol) and K$_2$CO$_3$ (6.5 g, 47 mmol) in n-BuOH (20 mL) was degassed with nitrogen and heated to 100° C. overnight. The cooled reaction mixture was filtered through a pad of celite and washed with EtOAc. The reaction solution was concentrated and the residue was diluted with EtOAc, washed with saturated aqueous NH$_4$Cl solution, followed by brine. The organics were dried over MgSO$_4$ and concentrated to give the crude product. The crude product was purified by column chromatography to give the title compound, (1.2 g, 37% yield). Partial racemization of the stereocenter was observed. MS (ESI) m/z 343.1 (M+H).

Example 1B. tert-butyl (1-(3-fluoro-2'-(methylsulfonyl)-[1,1'-biphenyl]-4-yl)-2-oxopiperidin-3-yl)carbamate

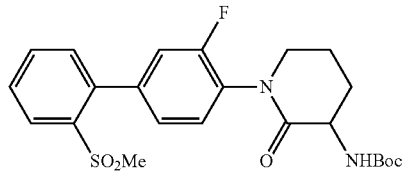 [SMILES: CC(C)(C)OC(=O)NC1CCCN(c2ccc(-c3ccccc3S(C)(=O)=O)cc2F)C1=O]

A mixture of Example 1A (150 mg, 0.44 mmol), (2-(methylsulfonyl)phenyl)boronic acid (260 mg, 1.3 mmol), Na$_2$CO$_3$ (230 mg, 2.2 mmol) and chloro(2-dicyclohexylphosphino-2',6'-dimethoxy-1,1'-biphenyl)[2-(2'-amino-1,1'-biphenyl)]palladium(II) (47 mg, 0.066 mmol) in toluene (2.0 mL), EtOH (2.0 mL) and H$_2$O (0.20 mL) was purged with argon and heated by microwave irradiation for 1 hr at 150° C. in a sealed vial. The reaction mixture was concentrated and purified by column chromatography to give Example 1B (160 mg, 79% yield. MS (ESI) m/z 463.2 (M+H).

Example 1C. 3-amino-1-(3-fluoro-2'-(methylsulfonyl)-[1,1'-biphenyl]-4-yl)piperidin-2-one

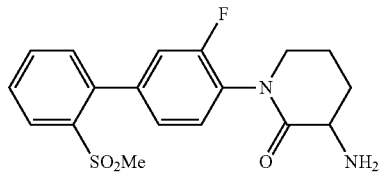 [SMILES: CS(=O)(=O)c1ccccc1-c1ccc(N2CCCC(N)C2=O)c(F)c1]

To a solution of Example 1B (160 mg, 0.35 mmol) in CH$_2$Cl$_2$ (5.0 mL) was added HCl in dioxane (0.87 mL, 3.5 mmol). After stirring for 6 h at rt, the reaction mixture was concentrated to give the crude product (125 mg, 99%.) MS (ESI) m/z 363.1 (M+H).

Example 1

To a solution of Example 1C (30 mg, 0.075 mmol)) in DMF (1.0 mL) was added 1-chloro-4-isocyanatobenzene (12 mg, 0.075 mmol) and Et$_3$N (0.11 mL, 0.75 mmol). After stirring for 1 h at rt, the reaction mixture was filtered, and the product was purified by reverse phase preparative HPLC to give the title compound, (55 mg, 60% yield). MS (ESI) m/z 516.1 (M+H). $^1$H NMR (500 MHz, DMSO-d6) δ 12.50 (s, 1H), 8.25 (d, J=7.8 Hz, 1H), 8.05-7.63 (m, 9H), 7.16-6.97 (m, 3H), 6.72 (d, J=7.4 Hz, 1H), 4.33-4.10 (m, 1H), 4.04-3.84 (m, 2H), 2.35 (t, J=9.0 Hz, 1H), 2.18 (d, J=9.8 Hz, 2H), 2.04-1.86 (m, 1H). Analytical HPLC: RT=1.74 min (Method B).

Example 2. 1-(5-chloropyridin-2-yl)-3-(1-(3-fluoro-2'-(methylsulfonyl)-[1,1'-biphenyl]-4-yl)-2-oxopiperidin-3-yl)urea

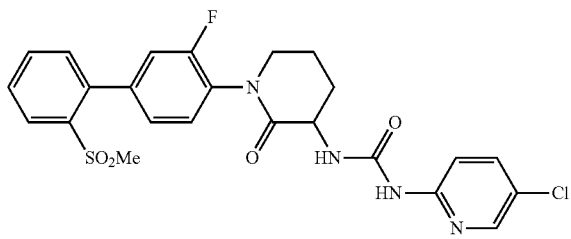 [SMILES: CS(=O)(=O)c1ccccc1-c1ccc(N2CCCC(NC(=O)Nc3ccc(Cl)cn3)C2=O)c(F)c1]

To a solution of 5-chloropyridin-2-amine (10 mg, 0.078 mmol) in DCM (0.50 mL) was added pyridine (0.025 ml, 0.31 mmol). After stirring for 5 min, 4-nitrophenyl chloroformate (17 mg, 0.086 mmol) was added, and the mixture was stirred at rt overnight. To the reaction mixture was added 1C (28 mg, 0.078 mmol), followed by TEA (0.050 mL), and the reaction mixture was stirred overnight. The reaction mixture was concentrated to give the crude product, which was purified by reverse phase preparative HPLC to provide the title compound (19 mg, 46% yield. MS(ESI) m/z 517.0 (M+H). $^1$H NMR (500 MHz, DMSO-$d_6$) δ 9.47 (s, 1H), 8.22 (d, J=2.3 Hz, 1H), 8.10 (d, J=7.8 Hz, 1H), 8.01 (br. s., 1H), 7.84-7.75 (m, 2H), 7.75-7.66 (m, 1H), 7.58 (d, J=8.8 Hz, 1H), 7.51-7.42 (m, 2H), 7.36 (d, J=11.0 Hz, 1H), 7.28 (d, J=8.0 Hz, 1H), 4.51-4.35 (m, 1H), 3.80-3.56 (m, 2H), 2.90 (s, 3H), 2.33 (dd, J=11.6, 5.8 Hz, 1H), 2.03 (d, J=5.5 Hz, 2H), 1.89-1.83 (m, 1H). Analytical HPLC: RT=1.60 min (Method A).

Example 3. 4'-(2-oxo-3-(3-(4-(trifluoromethyl)phenyl)ureido)piperidin-1-yl)-[1,1'-biphenyl]-2-carboxamide

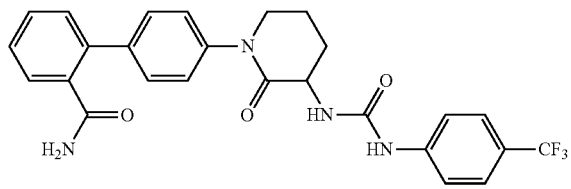 [SMILES: NC(=O)c1ccccc1-c1ccc(N2CCCC(NC(=O)Nc3ccc(C(F)(F)F)cc3)C2=O)cc1]

Example 3A. 1-(1-(4-chlorophenyl)-2-oxopiperidin-3-yl)-3-(4-(trifluoromethyl)phenyl)urea

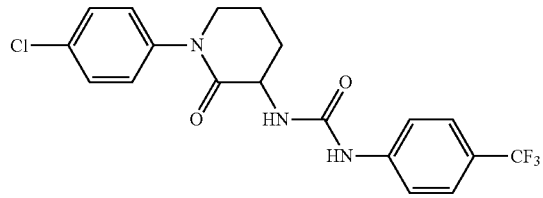 [SMILES: O=C(Nc1ccc(C(F)(F)F)cc1)NC1CCCN(c2ccc(Cl)cc2)C1=O]

Example 3A was synthesized from 1-chloro-4-iodobenzene using the procedures described in Examples 1A and 1C.1. MS (ESI) m/z 412.3 (M+H).

Example 3

To a solution of Example 3A (25 mg, 0.061 mmol), (2-carbamoylphenyl)boronic acid (30 mg, 0.18 mmol) and CsF (46 mg, 0.30 mmol) in CH$_3$CN (1.3 mL) and H$_2$O (0.20 mL) was added dichlorobis(tricyclohexylphosphine) palladium(II) (9.0 mg, 0.012 mmol). The reaction mixture was purged with nitrogen and heated by microwave irradiation for 0.5 hr at 150° C. in a sealed vial. The reaction mixture was filtered, and the product was purified via preparative reverse phase HPLC to give the title compound, (2.1 mg, 6.7% yield.) MS (ESI) m/z 497.3 (M+H). $^1$H NMR (500 MHz, DMSO-d6) δ 9.26 (s, 1H), 7.71 (br. s., 1H), 7.61-7.53 (m, 3H), 7.49-7.23 (m, 9H), 6.74 (d, J=6.7 Hz, 1H), 4.42-4.30 (m, 1H), 3.72 (d, J=14.4 Hz, 1H), 3.52 (br. s., 1H), 2.28 (br. s., 1H), 2.00 (br. s., 2H), 1.82 (br. s., 1H). Analytical HPLC: RT=1.649 min (Method B).

The following are additional Examples, prepared using the methods described above or modifications thereof known to one skilled in the art, of the compounds of Formula (I) of the present invention.

Examples 4-30 below were similarly prepared using the general procedures described for Example 1.

Example 4. 4'-(3-(3-(4-chlorophenyl)ureido)-2-oxopiperidin-1-yl)-[1,1'-biphenyl]-2-carboxamide

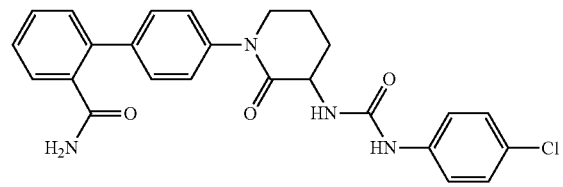 [SMILES: NC(=O)c1ccccc1-c1ccc(N2CCCC(NC(=O)Nc3ccc(Cl)cc3)C2=O)cc1]

MS(ESI) m/z 462.9 (M+H). $^1$H NMR (500 MHz, DMSO-$d_6$) δ 8.94 (s, 1H), 7.71 (s, 1H), 7.54-7.23 (m, 13H), 6.58 (d, J=6.6 Hz, 1H), 4.42-4.25 (m, 1H), 3.83-3.60 (m, 2H), 2.34-2.20 (m, 1H), 2.05-1.92 (m, 2H), 1.90-1.69 (m, 1H). Analytical HPLC: RT=1.48 min (Method B).

Example 5. 1-(1-(3-fluoro-2'-(methylsulfonyl)-[1,1'-biphenyl]-4-yl)-2-oxopiperidin-3-yl)-3-(p-tolyl)urea

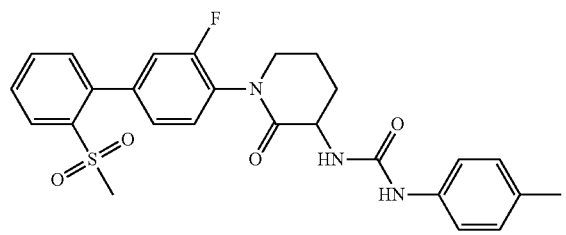 [SMILES: Cc1ccc(NC(=O)NC2CCCN(c3ccc(-c4ccccc4S(C)(=O)=O)cc3F)C2=O)cc1]

MS(ESI) m/z 495.9 (M+H). $^1$H NMR (500 MHz, DMSO-$d_6$) δ 8.60 (s, 1H), 8.08 (m, 1H), 7.77 (m, 1H), 7.69 (m, 1H), 7.50-7.39 (m, 2H), 7.33 (d, J=11.0 Hz, 1H), 7.29-7.20 (m, 3H), 7.03 (d, J=8.1 Hz, 2H), 6.46 (d, J=7.2 Hz, 1H), 4.39-4.27 (m, 1H), 3.66 (m, 2H), 2.88 (s, 3H), 2.25 (d, J=6.9 Hz, 1H), 2.20 (s, 3H), 2.05-1.95 (m, 2H), 1.83 (m, 1H). Analytical HPLC: RT=1.61 min (Method B).

Example 6. 4'-(3-(3-(4-chlorophenyl)ureido)-2-oxopiperidin-1-yl)-3'-fluoro-[1,1'-biphenyl]-2-carboxamide

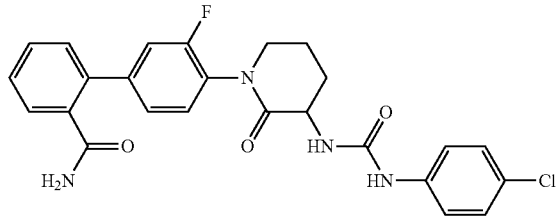 [SMILES: NC(=O)c1ccccc1-c1ccc(N2CCCC(NC(=O)Nc3ccc(Cl)cc3)C2=O)c(F)c1]

MS(ESI) m/z 481.1 (M+H). $^1$H NMR (500 MHz, DMSO-$d_6$) δ 8.91 (s, 1H), 7.83 (s, 1H), 7.56-7.38 (m, 8H), 7.34-7.19 (m, 4H), 6.59 (d, J=7.0 Hz, 1H), 4.40-4.28 (m, 1H), 3.69-3.49 (m, 2H), 2.27 (d, J=6.3 Hz, 1H), 2.06-1.96 (m, 2H), 1.83 (m, 1H). Analytical HPLC: RT=1.59 min (Method B).

Example 7. 4'-(2-oxo-3-(3-(p-tolyl)ureido)piperidin-1-yl)-[1,1'-biphenyl]-2-Carboxamide

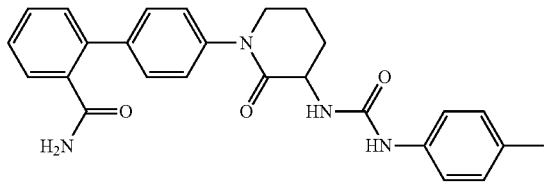 [SMILES: Cc1ccc(NC(=O)NC2CCCN(c3ccc(-c4ccccc4C(N)=O)cc3)C2=O)cc1]

MS(ESI) m/z 443 (M+H). $^1$H NMR (500 MHz, DMSO-$d_6$) δ 8.67 (s, 1H), 7.74 (br. s., 1H), 7.54-7.23 (m, 11H), 7.04 (d, J=8.2 Hz, 2H), 6.48 (d, J=6.8 Hz, 1H), 4.36-4.22 (m, 1H), 3.78-3.63 (m, 1H), 2.27 (m, 5H), 1.98 (m, 2H), 1.85-1.66 (m, 1H). Analytical HPLC: RT=1.39 min (Method B).

Example 8. 1-(1-(3-fluoro-2'-(methylsulfonyl)-[1,1'-biphenyl]-4-yl)-2-oxopiperidin-3-yl)-3-(4-(methylthio)phenyl)urea

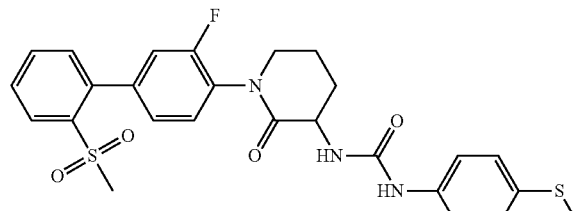

MS(ESI) m/z 528.1 (M+H). $^1$H NMR (500 MHz, DMSO-$d_6$) δ 8.74 (s, 1H), 8.09 (d, J=7.7 Hz, 1H), 7.77 (t, J=7.4 Hz, 1H), 7.69 (t, J=7.7 Hz, 1H), 7.50-7.39 (m, 2H), 7.35 (m, 3H), 7.26 (d, J=8.1 Hz, 1H), 7.17 (d, J=8.5 Hz, 2H), 6.52 (d, J=7.0 Hz, 1H), 4.39-4.27 (m, 1H), 3.65-3.55 (m, 2H), 2.88 (s, 3H), 2.39 (s, 3H), 2.26 (m, 1H), 2.08-1.96 (m, 2H), 1.84 (m, 1H). Analytical HPLC: RT=1.65 min (Method B).

Example 9. 1-(1-(3-fluoro-[1,1'-biphenyl]-4-yl)-2-oxopiperidin-3-yl)-3-(p-tolyl)urea

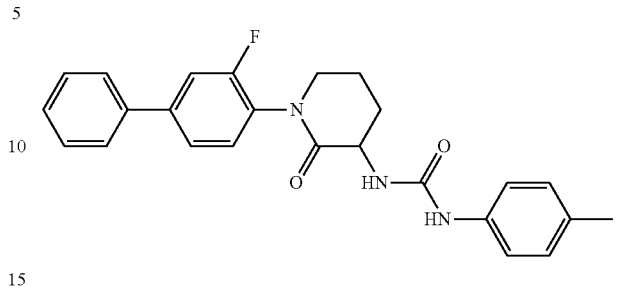

MS(ESI) m/z 418.2 (M+H). $^1$H NMR (500 MHz, DMSO-$d_6$) δ 8.63 (s, 1H), 7.84-7.35 (m, 8H), 7.27 (d, J=8.2 Hz, 2H), 7.04 (d, J=8.1 Hz, 2H), 6.49 (d, J=6.9 Hz, 1H), 4.42-4.27 (m, 1H), 3.74-3.60 (m, 1H), 3.57-3.45 (m, 1H), 2.29 (m, 1H), 2.21 (s, 3H), 2.01 (m, 2H), 1.82 (m, 1H). Analytical HPLC: RT=2.06 min (Method B).

Example 10. 3-{1-[2-fluoro-4-(2-oxo-1,2-dihydropyridin-1-yl)phenyl]-2-oxopiperidin-3-yl}-1-[4-(trifluoromethyl)phenyl]urea

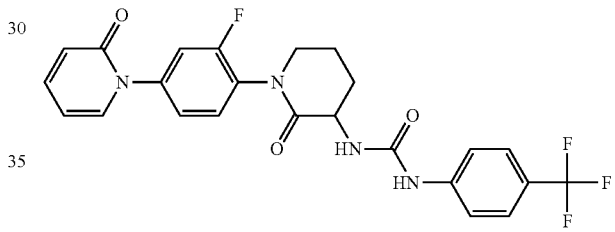

MS(ESI) m/z 488.8 (M+H). $^1$H NMR (500 MHz, DMSO-$d_6$) δ 9.18 (s, 1H), 7.76-7.44 (m, 8H), 7.30 (d, J=8.2 Hz, 1H), 6.72 (d, J=7.2 Hz, 1H), 6.51 (d, J=9.2 Hz, 1H), 6.37 (t, J=6.6 Hz, 1H), 4.45-4.28 (m, 1H), 3.80-3.64 (m, 2H), 2.26 (d, J=5.3 Hz, 1H), 2.02 (m, 2H), 1.87 (m, 1H). Analytical HPLC: RT=1.55 min (Method B).

Example 11. 1-(1-(3-fluoro-2'-(methylsulfonyl)-[1,1'-biphenyl]-4-yl)-2-oxopiperidin-3-yl)-3-(4-(trifluoromethyl)phenyl)urea

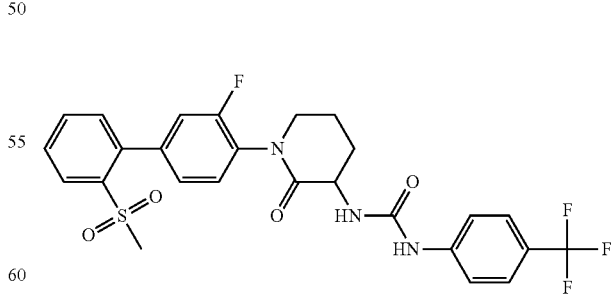

MS(ESI) m/z 550.1 (M+H). $^1$H NMR (500 MHz, DMSO-$d_6$) δ 9.19 (s, 1H), 8.11 (d, J=7.7 Hz, 1H), 7.78 (t, J=7.3 Hz, 1H), 7.71 (t, J=7.6 Hz, 1H), 7.64-7.55 (m, 4H), 7.51-7.44 (m, 2H), 7.37 (d, J=11.0 Hz, 1H), 7.29 (d, J=7.9 Hz, 1H), 6.73 (d, J=6.9 Hz, 1H), 4.44-4.32 (m, 1H), 3.78-3.62 (m,

2H), 2.90 (s, 3H), 2.31 (m, 1H), 2.04 (m, 2H), 1.93-1.79 (m, 1H). Analytical HPLC: RT=1.86 min (Method A).

Example 12. 1-(4-chlorophenyl)-3-{1-[2-fluoro-4-(2-oxo-1,2-dihydropyridin-1-yl)phenyl]-2-oxopiperidin-3-yl}urea

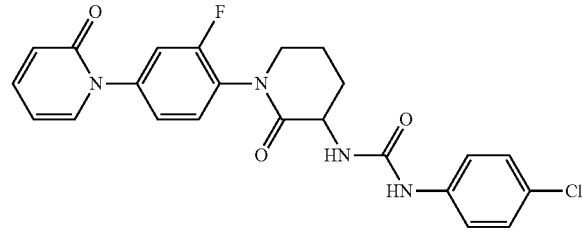 [SMILES: O=C(Nc1ccc(Cl)cc1)NC1CCCN(c2ccc(-n3ccccc3=O)cc2F)C1=O]

MS(ESI) m/z 455.2 (M+H). $^1$H NMR (500 MHz, DMSO-d$_6$) δ 8.87 (s, 1H), 7.65 (d, J=5.5 Hz, 1H), 7.57-7.37 (m, 5H), 7.32-7.17 (m, 3H), 6.59 (d, J=7.0 Hz, 1H), 6.50 (s, 1H), 6.37 (t, J=6.4 Hz, 1H), 4.56-4.29 (m, 1H), 3.85-3.62 (m, 2H), 2.26 (m, 5.6 Hz, 1H), 2.02 (m, 2H), 1.85 (m, 1H). Analytical HPLC: RT=1.47 min (Method A).

Example 13. 1-(4-chlorophenyl)-3-(1-(3-fluoro-[1,1'-biphenyl]-4-yl)-2-oxopiperidin-3-yl)urea

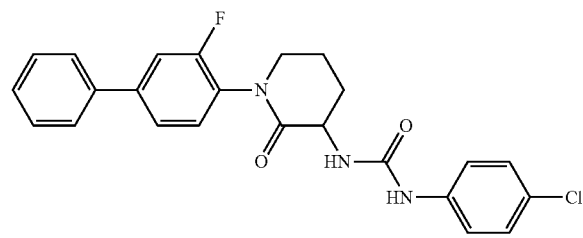 [SMILES: O=C(Nc1ccc(Cl)cc1)NC1CCCN(c2ccc(-c3ccccc3)cc2F)C1=O]

MS(ESI) m/z 438.2 (M+H). $^1$H NMR (500 MHz, DMSO-d$_6$) δ 8.90 (s, 1H), 7.81-7.38 (m, 10H), 7.32-7.21 (m, 2H), 6.59 (d, J=6.9 Hz, 1H), 4.40-4.27 (m, 1H), 3.67-3.41 (m, 2H), 2.28 (d, J=6.2 Hz, 1H), 2.07-1.96 (m, 2H), 1.84 (m, 1H). Analytical HPLC: RT=2.02 min (Method A).

Example 14. 1-(4-ethylphenyl)-3-(1-(3-fluoro-2'-(methylsulfonyl)-[1,1'-biphenyl]-4-yl)-2-oxopiperidin-3-yl)urea

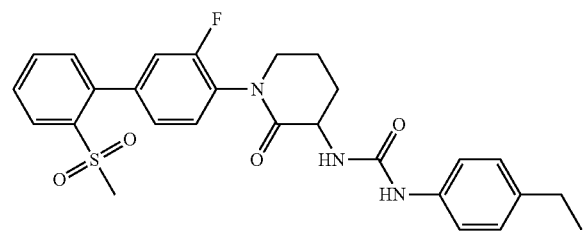

MS(ESI) m/z 510.3 (M+H). $^1$H NMR (500 MHz, DMSO-d$_6$) δ 8.63 (s, 1H), 8.10 (m, 1H), 7.78 (m, 1H), 7.70 (m, 1H), 7.51-7.41 (m, 2H), 7.37 (d, J=10.9 Hz, 1H), 7.29 (d, J=7.9 Hz, 3H), 7.06 (d, J=8.2 Hz, 2H), 6.48 (m, 1H), 4.42-4.28 (m, 1H), 3.76-3.60 (m, 2H), 2.90 (s, 3H), 2.60 (m, 2H), 2.29 (m, 1H), 2.02 (m, 2H), 1.82 (m, 1H), 1.14 (t, J=7.5 Hz, 3H). Analytical HPLC: RT=1.79 min (Method B).

Example 15. 1-(4-ethylphenyl)-3-(1-(3-fluoro-2'-(methylsulfonyl)-[1,1'-biphenyl]-4-yl)-2-oxopiperidin-3-yl)urea

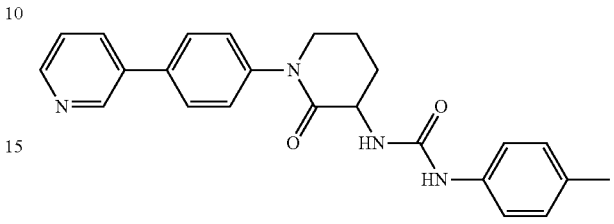

MS(ESI) m/z 400.9 (M+H). $^1$H NMR (500 MHz, DMSO-d$_6$) δ 8.92 (s, 1H), 8.68 (s, 1H), 8.58 (d, J=4.1 Hz, 1H), 8.11 (d, J=7.9 Hz, 1H), 7.76 (d, J=8.3 Hz, 2H), 7.60-7.41 (m, 3H), 7.29 (d, J=8.2 Hz, 2H), 7.04 (d, J=8.0 Hz, 2H), 6.49 (d, J=6.6 Hz, 1H), 4.56-4.17 (m, 1H), 3.89-3.64 (m, 2H), 2.30 (dd, J=11.9, 5.8 Hz, 1H), 2.22 (s, 3H), 2.06-1.96 (m, 2H), 1.86-1.68 (m, 1H). Analytical HPLC: RT=1.47 min (Method B).

Example 16. 1-(4-chlorophenyl)-3-(2-oxo-1-(4-(pyridin-3-yl)phenyl)piperidin-3-yl)urea

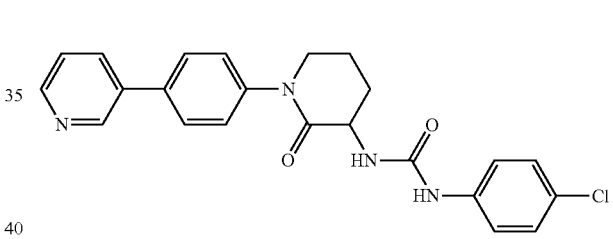

MS(ESI) m/z 421.1 (M+H). $^1$H NMR (500 MHz, DMSO-d$_6$) δ 8.93 (s, 2H), 8.59 (s, 1H), 8.11 (d, J=7.8 Hz, 1H), 7.76 (d, J=8.3 Hz, 2H), 7.55-7.39 (m, 5H), 7.27 (d, J=8.7 Hz, 2H), 6.58 (d, J=6.8 Hz, 1H), 4.39-4.20 (m, 1H), 3.82-3.62 (m, 2H), 2.29 (m, 5.8 Hz, 1H), 2.04-1.96 (m, 2H), 1.85-1.67 (m, 1H). Analytical HPLC: RT=1.56 min (Method B).

Example 17. 1-(1-(3-fluoro-2'-(methylsulfonyl)-[1,1'-biphenyl]-4-yl)-2-oxopiperidin-3-yl)-3-(4-methoxyphenyl)urea

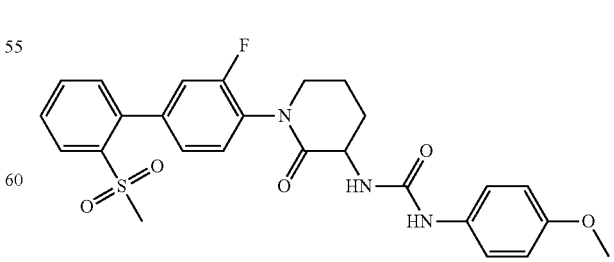

MS(ESI) m/z 511.8 (M+H). $^1$H NMR (500 MHz, DMSO-d$_6$) δ 8.53 (s, 1H), 8.10 (d, J=7.8 Hz, 1H), 7.78 (t, J=7.4 Hz, 1H), 7.70 (t, J=7.6 Hz, 1H), 7.50-7.41 (m, 2H), 7.36 (d,

J=10.9 Hz, 1H), 7.29 (d, J=8.7 Hz, 3H), 6.82 (d, J=8.8 Hz, 2H), 6.42 (d, J=6.9 Hz, 1H), 4.42-4.28 (m, 1H), 3.75-3.60 (m, 4H), 3.48-3.34 (m, 2H), 2.90 (s, 3H), 2.28 (m, 1H), 2.02 (m, 2H), 1.83 (m, 1H). Analytical HPLC: RT=1.46 min (Method B).

Example 18. 3'-fluoro-4'-(2-oxo-3-(3-(4-(trifluoromethyl)phenyl)ureido)piperidin-1-yl)-[1,1'-biphenyl]-2-carboxamide

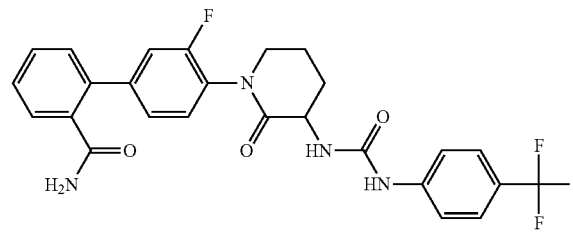

MS(ESI) m/z 515.2 (M+H). $^1$H NMR (500 MHz, DMSO-$d_6$) δ 9.20 (s, 1H), 7.83 (s, 1H), 7.59 (s, 4H), 7.51-7.38 (m, 6H), 7.34-7.21 (m, 2H), 6.71 (d, J=6.8 Hz, 1H), 4.42-4.24 (m, 1H), 3.76-3.48 (m, 2H), 2.30 (m, 1H), 2.02 (m, 2H), 1.85 (m, 1H). Analytical HPLC: RT=1.73 min (Method B).

Example 19. 1-(4-chloro-3-fluorophenyl)-3-(1-(3-fluoro-2'-(methylsulfonyl)-[1,1'-biphenyl]-4-yl)-2-oxopiperidin-3-yl)urea

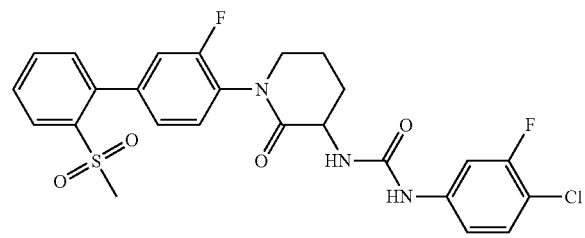 [SMILES: CS(=O)(=O)c1ccccc1-c1ccc(N2CCCC(NC(=O)Nc3ccc(Cl)c(F)c3)C2=O)c(F)c1]

MS(ESI) m/z 534.2 (M+H). $^1$H NMR (500 MHz, DMSO-$d_6$) δ 9.12 (s, 1H), 8.09 (d, J=7.8 Hz, 1H), 7.85-7.59 (m, 3H), 7.51-7.24 (m, 5H), 7.08 (d, J=8.1 Hz, 1H), 6.68 (d, J=7.1 Hz, 1H), 4.42-4.28 (m, 1H), 3.63 (m., 2H), 2.89 (s, 3H), 2.26 (m, 1H), 2.02 (m, 2H), 1.91-1.54 (m, 1H). Analytical HPLC: RT=1.93 min (Method B).

Example 20. 4'-(2-oxo-3-(3-(4-(trifluoromethyl)phenyl)ureido)piperidin-1-yl)-[1,1'-biphenyl]-3-carboxamide

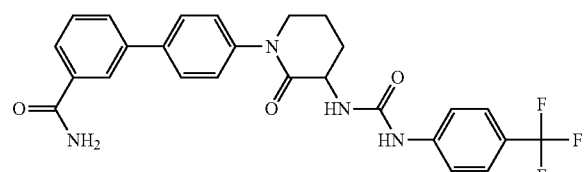

MS(ESI) m/z 497.3 (M+H). $^1$H NMR (500 MHz, DMSO-$d_6$) δ 9.24 (s, 1H), 8.21-8.11 (m, 2H), 7.83 (d, J=7.5 Hz, 2H), 7.74 (d, J=8.2 Hz, 2H), 7.65-7.52 (m, 5H), 7.41 (d, J=7.7 Hz, 3H), 6.75 (d, J=6.6 Hz, 1H), 4.40-4.21 (m, 1H), 3.71 (br. s., 2H), 2.26 (m, 1H), 2.00 (m, 2H), 1.84 (m, 1H). Analytical HPLC: RT=1.68 min (Method B).

Example 21. 1-(6-chloropyridin-3-yl)-3-(1-(3-fluoro-2'-(methylsulfonyl)-[1,1'-biphenyl]-4-yl)-2-oxopiperidin-3-yl)urea

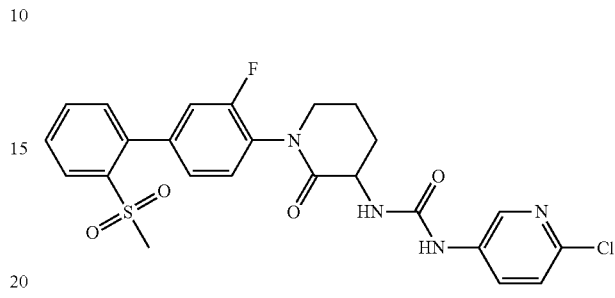

MS(ESI) m/z 517.2 (M+H). $^1$H NMR (500 MHz, DMSO-$d_6$) δ 9.12 (s, 1H), 8.41 (d, J=2.4 Hz, 1H), 8.11 (d, J=7.9 Hz, 1H), 7.95 (dd, J=8.7, 2.6 Hz, 1H), 7.83-7.67 (m, 2H), 7.51-7.24 (m, 5H), 6.77 (d, J=7.0 Hz, 1H), 4.45-4.23 (m, 1H), 3.75-3.56 (m, 2H), 2.91 (s, 3H), 2.40-2.26 (m, 1H), 2.03 (m, 2H), 1.91-1.79 (m, 1H). Analytical HPLC: RT=1.64 min (Method A).

Example 22. 1-(1-(3-fluoro-[1,1'-biphenyl]-4-yl)-2-oxopiperidin-3-yl)-3-(4-(trifluoromethyl)phenyl)urea

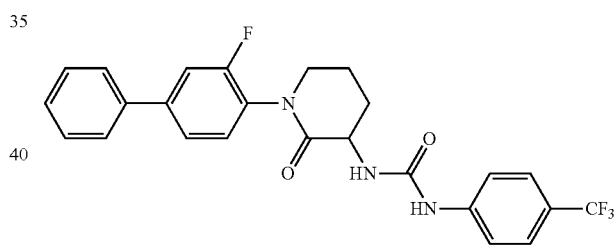

MS(ESI) m/z 472.2 (M+H). $^1$H NMR (500 MHz, DMSO-$d_6$) δ 9.22 (s, 1H), 7.72 (d, J=7.5 Hz, 2H), 7.65-7.54 (m, 6H), 7.51-7.28 (m, 3H), 6.74 (d, J=6.8 Hz, 1H), 4.44-4.30 (m, 1H), 3.73-3.58 (m, 2H), 2.31 (m, 1H), 2.03 (m, 2H), 1.86 (m, 1H). Analytical HPLC: RT=2.18 min (Method B).

Example 23. 1-(1-(3-fluoro-2'-(methylsulfonyl)-[1,1'-biphenyl]-4-yl)-2-oxopiperidin-3-yl)-3-(4-(methylsulfonyl)phenyl)urea

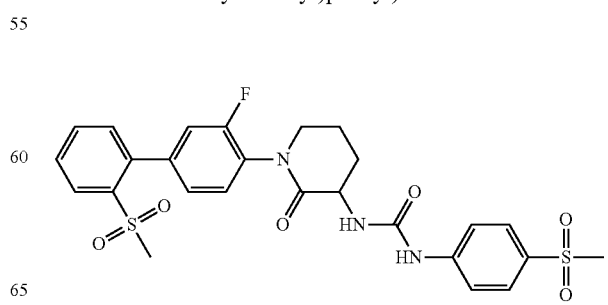

MS(ESI) m/z 560.2 (M+H). $^1$H NMR (500 MHz, DMSO-$d_6$) δ 9.34 (s, 1H), 8.10 (d, J=7.8 Hz, 1H), 7.85-7.58 (m, 6H), 7.52-7.42 (m, 2H), 7.38-7.22 (m, 2H), 6.79 (d, J=7.1 Hz, 1H), 4.46-4.29 (m, 1H), 3.82-3.46 (m, 2H), 3.12 (s, 3H), 2.95-2.85 (m, 3H), 2.29 (d, J=6.1 Hz, 1H), 2.04 (br. s., 2H), 1.89 (s, 1H). Analytical HPLC: RT=1.46 min (Method B).

Example 24. 1-(4-cyanophenyl)-3-(1-(3-fluoro-2'-(methylsulfonyl)-[1,1'-biphenyl]-4-yl)-2-oxopiperidin-3-yl)urea

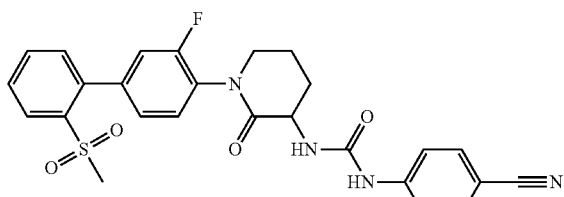

MS(ESI) m/z 507.2 (M+H). $^1$H NMR (500 MHz, DMSO-$d_6$) δ 8.53 (s, 1H), 8.10 (d, J=7.8 Hz, 1H), 7.78 (t, J=7.4 Hz, 1H), 7.70 (t, J=7.6 Hz, 1H), 7.50-7.41 (m, 2H), 7.36 (d, J=10.9 Hz, 1H), 7.29 (d, J=8.7 Hz, 3H), 6.82 (d, J=8.8 Hz, 2H), 6.42 (d, J=6.9 Hz, 1H), 4.42-4.28 (m, 1H), 3.75-3.60 (m, 2H), 2.90 (s, 3H), 2.28 (m, 1H), 2.02 (m, 2H), 1.83 (m, 1H). Analytical HPLC: RT=1.57 min (Method B).

Example 25. 1-(1-(3-fluoro-2'-(methylsulfonyl)-[1,1'-biphenyl]-4-yl)-2-oxopiperidin-3-yl)-3-(4-(trifluoromethoxy)phenyl)urea

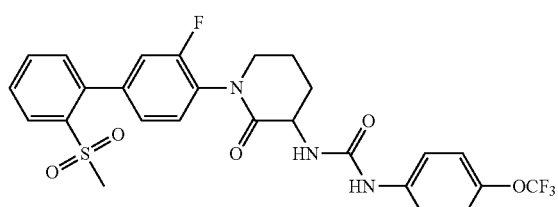

MS(ESI) m/z 566.3 (M+H). $^1$H NMR (500 MHz, DMSO-$d_6$) δ 8.96 (s, 1H), 8.10 (d, J=7.8 Hz, 1H), 7.78 (t, J=7.4 Hz, 1H), 7.70 (t, J=7.7 Hz, 1H), 7.54-7.42 (m, 4H), 7.37 (d, J=10.9 Hz, 1H), 7.28 (d, J=7.4 Hz, 1H), 7.23 (d, J=8.7 Hz, 2H), 6.60 (d, J=6.9 Hz, 1H), 4.42-4.31 (m, 1H), 3.76-3.59 (m, 2H), 2.90 (s, 3H), 2.30 (m, 1H), 2.02 (m, 2H), 1.92-1.76 (m, 1H). Analytical HPLC: RT=1.88 min (Method A).

Example 26. 1-(1-(3-fluoro-2'-(methylsulfonyl)-[1,1'-biphenyl]-4-yl)-2-oxopiperidin-3-yl)-3-(5-methylthiazol-2-yl)urea

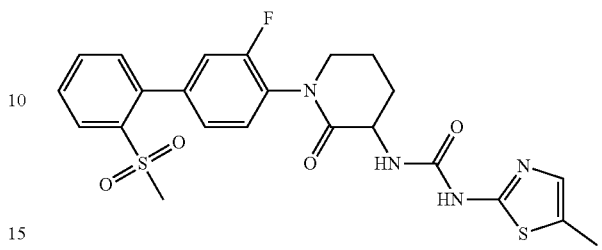

MS(ESI) m/z 502.8 (M+H). $^1$H NMR (500 MHz, DMSO-$d_6$) δ 8.11 (d, J=7.9 Hz, 1H), 7.83-7.69 (m, 2H), 7.51-7.42 (m, 2H), 7.39-7.25 (m, 2H), 7.08-6.93 (m, 2H), 4.47-4.23 (m, 1H), 3.69 (m, 2H), 2.90 (s, 3H), 2.29 (s, 4H), 2.04 (m, 2H), 1.89-1.78 (m, 2H). Analytical HPLC: RT=1.32 min (Method A).

Example 27. 1-(6-chloropyridazin-3-yl)-3-(1-(3-fluoro-2'-(methylsulfonyl)-[1,1'-biphenyl]-4-yl)-2-oxopiperidin-3-yl)urea

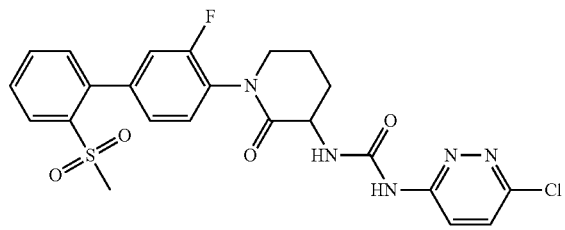 [SMILES: CS(=O)(=O)c1ccccc1-c1ccc(N2CCCC(NC(=O)Nc3ccc(Cl)nc3)C2=O)c(F)c1]

MS(ESI) m/z 518.2 (M+H). $^1$H NMR (500 MHz, DMSO-$d_6$) δ 9.96 (s, 1H), 8.22-7.98 (m, 2H), 7.88-7.63 (m, 4H), 7.51-7.39 (m, 2H), 7.32-7.18 (m, 2H), 4.67-4.32 (m, 1H), 3.69 (br. s., 2H), 2.89 (s, 3H), 2.31 (m, 1H), 2.04 (m, 2H), 1.89 (m, 1H). Analytical HPLC: RT=1.46 min (Method A).

Example 28. 1-(1-(3-fluoro-2'-(methylsulfonyl)-[1,1'-biphenyl]-4-yl)-2-oxopiperidin-3-yl)-3-(4-fluorophenyl)urea

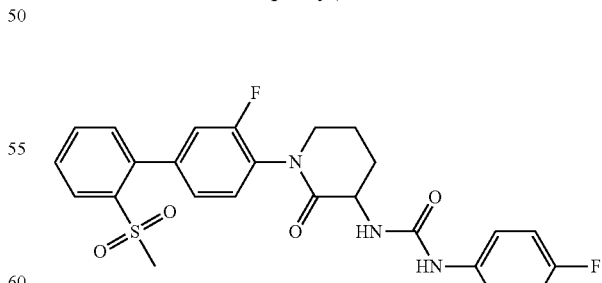

MS(ESI) m/z 500 (M+H). $^1$H NMR (500 MHz, DMSO-$d_6$) δ 8.76 (s, 1H), 8.09 (d, J=7.7 Hz, 1H), 7.77 (m, 1H), 7.69 (m, 1H), 7.50-7.41 (m, 2H), 7.41-7.30 (m, 3H), 7.26 (d, J=8.0 Hz, 1H), 7.06 (m, 2H), 6.51 (d, J=7.1 Hz, 1H), 4.40-4.28 (m, 1H), 3.67-3.52 (m, 2H), 2.89 (s, 3H), 2.31-

2.20 (m, 1H), 2.07-1.96 (m, 2H), 1.84 (m, 1H). Analytical HPLC: RT=1.54 min (Method B).

Example 29. 2'-fluoro-4'-(2-oxo-3-(3-(4-(trifluoromethyl)phenyl)ureido)piperidin-1-yl)-[1,1'-biphenyl]-2-carboxamide

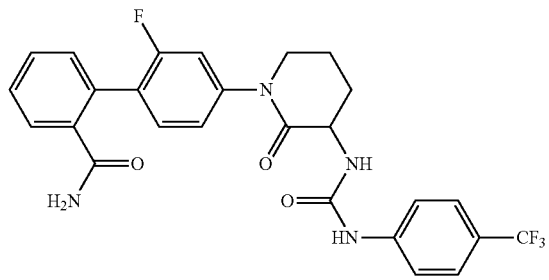 [SMILES: NC(=O)c1ccccc1-c1ccc(N2CCCC(NC(=O)Nc3ccc(C(F)(F)F)cc3)C2=O)cc1F]

MS(ESI) m/z 515 (M+H). $^1$H NMR (500 MHz, DMSO-$d_6$) δ 9.30 (s, 1H), 7.70 (br. s., 1H), 7.63-7.11 (m, 12H), 6.77 (d, J=6.7 Hz, 1H), 4.50-4.30 (m, 1H), 3.75 (d, J=19.2 Hz, 2H), 2.38-2.20 (m, 1H), 2.06-1.94 (m, 2H), 1.88-1.73 (m, 1H). Analytical HPLC: RT=1.64 min (Method A).

Example 30. 4'-(3-(3-(4-chlorophenyl)ureido)-2-oxopiperidin-1-yl)-2'-fluoro-[1,1'-biphenyl]-2-carboxamide

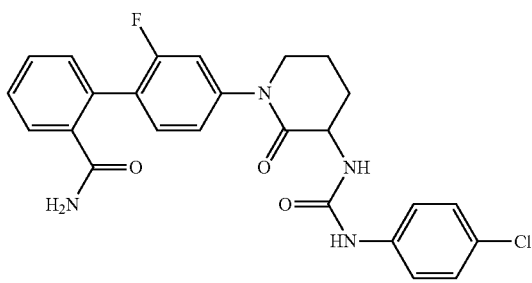 [SMILES: NC(=O)c1ccccc1-c1ccc(N2CCCC(NC(=O)Nc3ccc(Cl)cc3)C2=O)cc1F]

MS(ESI) m/z 481 (M+H). $^1$H NMR (500 MHz, DMSO-$d_6$) δ 8.97 (s, 1H), 7.72 (s, 1H), 7.59-7.10 (m, 12H), 6.59 (d, J=6.8 Hz, 1H), 4.44-4.31 (m, 1H), 3.85-3.67 (m, 2H), 2.27 (m, 1H), 1.99 (m, 2H), 1.80 (m, 1H). Analytical HPLC: RT=1.63 min (Method A).

Examples 31-53 were similarly prepared using the procedures described above for Example 2 or 3.

Example 31. 1-(1-(2'-fluoro-[1,1'-biphenyl]-4-yl)-2-oxopiperidin-3-yl)-3-(4-(trifluoromethyl)phenyl)urea

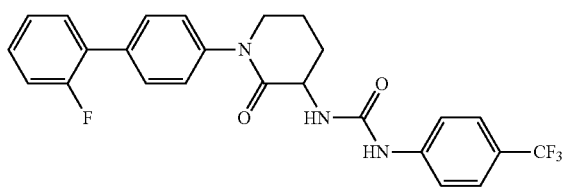 [SMILES: O=C(Nc1ccc(C(F)(F)F)cc1)NC1CCCN(c2ccc(-c3ccccc3F)cc2)C1=O]

MS(ESI) m/z 472.3 (M+H). $^1$H NMR (500 MHz, DMSO-$d_6$) δ 9.19 (s, 1H), 7.73-7.49 (m, 7H), 7.40 (d, J=7.9 Hz, 3H), 7.32-7.19 (m, 2H), 6.70 (d, J=6.8 Hz, 1H), 4.42-4.23 (m, 1H), 3.86-3.72 (m, 2H), 2.33-2.19 (m, 1H), 2.00 (m, 2H), 1.84 (m, 1H). Analytical HPLC: RT=2.14 min (Method B).

Example 32. 1-(1-(4-(2-fluoropyridin-3-yl)phenyl)-2-oxopiperidin-3-yl)-3-(4-(trifluoromethyl)phenyl)urea

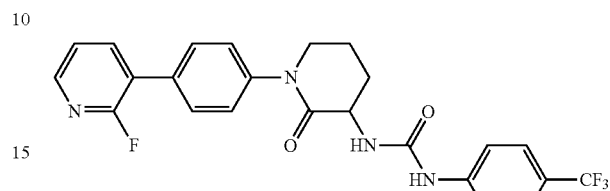

MS(ESI) m/z 473 (M+H). $^1$H NMR (500 MHz, DMSO-$d_6$) δ 9.22 (s, 1H), 8.32-8.04 (m, 2H), 7.75-7.55 (m, 6H), 7.49-7.32 (m, 3H), 6.71 (d, J=6.9 Hz, 1H), 4.48-4.29 (m, 1H), 3.82-3.62 (m, 1H), 3.61-3.48 (m, 1H), 2.29 (m, 1H), 2.07-1.92 (m, 2H), 1.88-1.64 (m, 1H). Analytical HPLC: RT=1.91 min (Method B).

Example 33. 1-(1-(2'-cyano-[1,1'-biphenyl]-4-yl)-2-oxopiperidin-3-yl)-3-(4-(trifluoromethyl)phenyl)urea

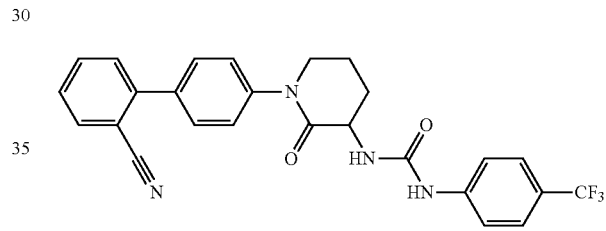

MS(ESI) m/z 479.2 (M+H). $^1$H NMR (500 MHz, DMSO-$d_6$) δ 9.23 (s, 1H), 7.94 (d, J=7.7 Hz, 1H), 7.83-7.74 (m, 1H), 7.68-7.54 (m, 8H), 7.48 (d, J=8.3 Hz, 2H), 6.72 (d, J=6.9 Hz, 1H), 4.45-4.25 (m, 1H), 3.92-3.68 (m, 2H), 2.28 (d, J=6.0 Hz, 1H), 2.10-1.97 (m, 2H), 1.65 (s, 1H). Analytical HPLC: RT=1.89 min (Method A).

Example 34. methyl 4'-(2-oxo-3-(3-(4-(trifluoromethyl)phenyl)ureido)piperidin-1-yl)-[1,1'-biphenyl]-2-carboxylate

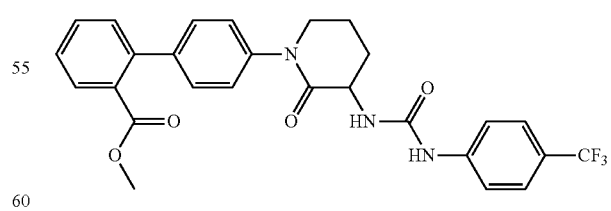

MS(ESI) m/z 512 (M+H). $^1$H NMR (500 MHz, DMSO-$d_6$) δ 9.21 (s, 1H), 7.73 (d, J=7.6 Hz, 1H), 7.63-7.55 (m, 5H), 7.50-7.25 (m, 6H), 6.69 (d, J=6.6 Hz, 1H), 4.42-4.24 (m, 1H), 3.75 (d, J=5.5 Hz, 2H), 3.60 (s, 3H), 2.29 (d, J=5.4 Hz, 1H), 1.79 (m, 2H), 1.44-1.07 (m, 1H). Analytical HPLC: RT=2.09 min (Method A).

Example 35. 1-(2-oxo-1-(4-(pyridin-3-yl)phenyl)piperidin-3-yl)-3-(4-(trifluoromethyl)phenyl)urea

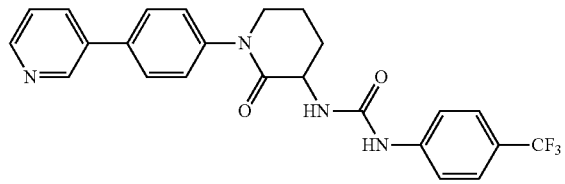 [SMILES: O=C(Nc1ccc(C(F)(F)F)cc1)NC1CCCN(c2ccc(-c3cccnc3)cc2)C1=O]

MS(ESI) m/z 455.1 (M+H). ¹H NMR (500 MHz, DMSO-$d_6$) δ 9.23 (s, 1H), 8.89 (s, 1H), 8.57 (d, J=4.0 Hz, 1H), 8.09 (d, J=7.8 Hz, 1H), 7.76 (d, J=8.2 Hz, 2H), 7.63-7.32 (m, 7H), 6.71 (d, J=6.8 Hz, 1H), 4.44-4.31 (m, 1H), 3.81-3.68 (m, 1H), 3.60-3.42 (m, 1H), 2.30 (m, 1H), 2.00 (m, 2H), 1.90-1.76 (m, 1H). Analytical HPLC: RT=1.37 min (Method A).

Example 36. 1-(1-([1,1'-biphenyl]-4-yl)-2-oxopiperidin-3-yl)-3-(4-(trifluoromethyl)phenyl)urea

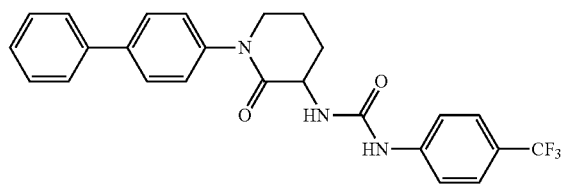

MS(ESI) m/z 454.3 (M+H). ¹H NMR (500 MHz, DMSO-$d_6$) δ 9.21 (s, 1H), 7.74-7.55 (m, 8H), 7.50-7.32 (m, 5H), 6.70 (d, J=6.7 Hz, 1H), 4.44-4.28 (m, 1H), 3.81-3.54 (m, 2H), 2.28 (d, J=6.8 Hz, 1H), 2.09-1.95 (m, 2H), 1.88-1.72 (m, 1H). Analytical HPLC: RT=2.12 min (Method A).

Example 37. 1-(1-(3'-fluoro-[1,1'-biphenyl]-4-yl)-2-oxopiperidin-3-yl)-3-(4-(trifluoromethyl)phenyl)urea

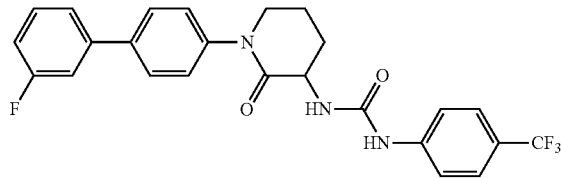 [SMILES: O=C(Nc1ccc(C(F)(F)F)cc1)NC1CCCN(c2ccc(-c3cccc(F)c3)cc2)C1=O]

MS(ESI) m/z 472.2 (M+H). ¹H NMR (500 MHz, DMSO-$d_6$) δ 9.20 (s, 1H), 7.72 (d, J=8.3 Hz, 2H), 7.62-7.36 (m, 9H), 7.18 (t, J=8.0 Hz, 1H), 6.70 (d, J=6.9 Hz, 1H), 4.40-4.20 (m, 1H), 3.78-3.56 (m, 2H), 2.28-2.22 (m, 1H), 2.04-1.94 (m, 2H), 1.84 (m, 1H). Analytical HPLC: RT=2.1 min (Method).

Example 38. 1-(2-oxo-1-(4-(pyridin-4-yl)phenyl)piperidin-3-yl)-3-(4-(trifluoromethyl)phenyl)urea

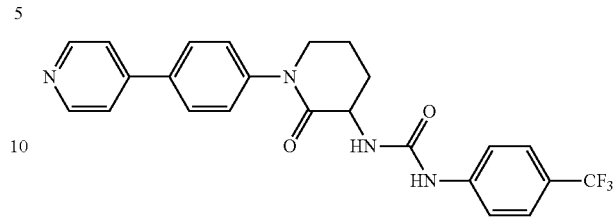

MS(ESI) m/z 454.9 (M+H). ¹H NMR (500 MHz, DMSO-$d_6$) δ 9.19 (s, 1H), 8.61 (d, J=5.0 Hz, 2H), 7.82 (d, J=8.4 Hz, 2H), 7.72 (d, J=5.6 Hz, 2H), 7.58 (s, 4H), 7.45 (d, J=8.4 Hz, 2H), 6.70 (d, J=7.1 Hz, 1H), 4.44-4.30 (m, 1H), 3.83-3.66 (m, 2H), 2.26 (m, 1H), 2.05-1.95 (m, 2H), 1.85 (m, 1H). Analytical HPLC: RT=1.67 min (Method B).

Example 39. 1-(1-(4'-fluoro-[1,1'-biphenyl]-4-yl)-2-oxopiperidin-3-yl)-3-(4-(trifluoromethyl)phenyl)urea

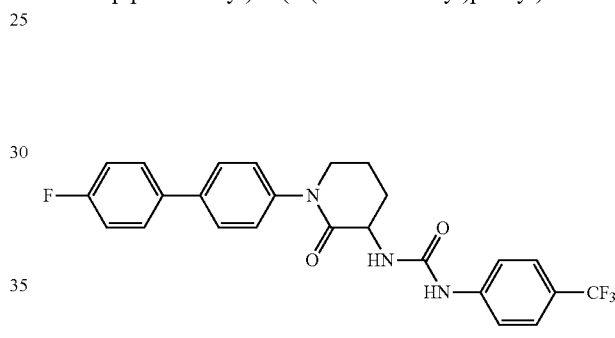

MS(ESI) m/z 472 (M+H). ¹H NMR (500 MHz, DMSO-$d_6$) δ 9.22 (s, 1H), 7.81-7.52 (m, 8H), 7.39 (d, J=8.2 Hz, 2H), 7.29 (t, J=8.7 Hz, 2H), 6.70 (d, J=6.7 Hz, 1H), 4.47-4.28 (m, 1H), 3.82-3.59 (m, 2H), 2.38-2.21 (m, 1H), 2.00 (m, 2H), 1.84 (m, 1H). Analytical HPLC: RT=2.04 min (Method A).

Example 40. methyl 3-fluoro-4'-(2-oxo-3-(3-(4-(trifluoromethyl)phenyl)ureido)piperidin-1-yl)-[1,1'-biphenyl]-2-carboxylate

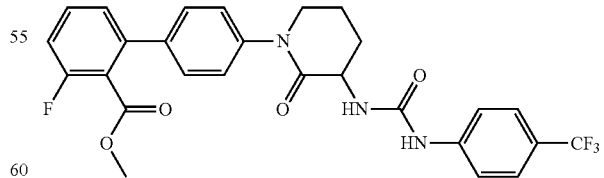

MS(ESI) m/z 530.4 (M+H). ¹H NMR (500 MHz, DMSO-$d_6$) δ 9.38 (s, 1H), 7.70-7.53 (m, 5H), 7.42-7.29 (m, 6H), 6.90 (d, J=6.7 Hz, 1H), 4.45-4.29 (m, 1H), 3.86-3.71 (m, 1H), 3.67-3.37 (m, 4H), 2.11-1.62 (m, 3H), 1.41-1.05 (m, 1H). Analytical HPLC: RT=2.15 min (Method B).

Example 41. 1-(1-(4-(2-ethoxy-5-fluoropyridin-4-yl)phenyl)-2-oxopiperidin-3-yl)-3-(4-(trifluoromethyl)phenyl)urea

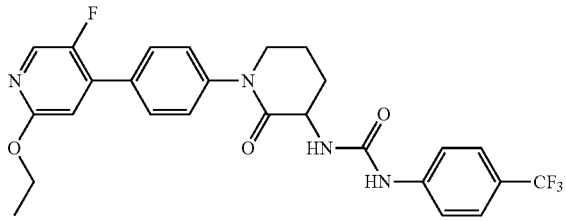 [SMILES: CCOc1cc(-c2ccc(N3CCCC(NC(=O)Nc4ccc(C(F)(F)F)cc4)C3=O)cc2)c(F)cn1]

MS(ESI) m/z 517.3 (M+H). ¹H NMR (500 MHz, DMSO-d₆) δ 9.24 (s, 1H), 8.21 (s, 1H), 7.75-7.55 (m, 6H), 7.46 (d, J=8.4 Hz, 2H), 6.98 (d, J=5.3 Hz, 1H), 6.73 (d, J=6.8 Hz, 1H), 4.45-4.25 (m, 3H), 3.91-3.68 (m, 2H), 3.54-3.41 (m, 3H), 2.38-2.25 (m, 1H), 2.00 (m, 2H), 1.85 (m, 1H). Analytical HPLC: RT=2.17 min (Method B).

Example 42. 4'-(2-oxo-3-(3-(4-(trifluoromethyl)phenyl)ureido)piperidin-1-yl)-[1,1'-biphenyl]-2-carboxylic acid

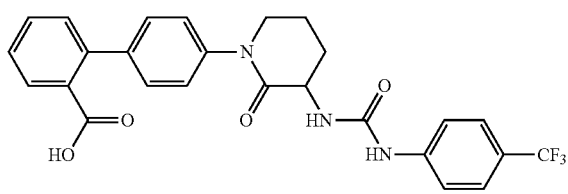

MS(ESI) m/z 498.1 (M+H). ¹H NMR (500 MHz, DMSO-d₆) δ 9.51 (s, 1H), 7.78-7.53 (m, 5H), 7.47-7.17 (m, 7H), 6.99 (d, J=6.1 Hz, 1H), 4.43-4.24 (m, 1H), 3.75-3.57 (m, 2H), 2.29 (d, J=5.8 Hz, 1H), 1.98 (d, J=6.1 Hz, 2H), 1.86-1.63 (m, 1H). Analytical HPLC: RT=1.92 min (Method A).

Example 43. 1-(1-(3'-(methylsulfonyl)-[1,1'-biphenyl]-4-yl)-2-oxopiperidin-3-yl)-3-(4-(trifluoromethyl)phenyl)urea

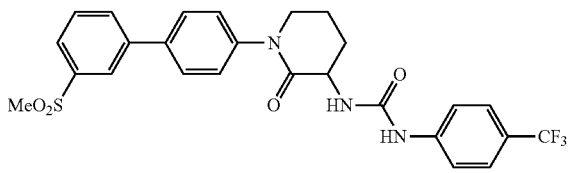 [SMILES: CS(=O)(=O)c1cccc(-c2ccc(N3CCCC(NC(=O)Nc4ccc(C(F)(F)F)cc4)C3=O)cc2)c1]

MS(ESI) m/z 532.1 (M+H). ¹H NMR (500 MHz, DMSO-d₆) δ 9.23 (s, 1H), 8.13 (s, 1H), 8.03 (s, 1H), 7.90 (d, J=7.8 Hz, 1H), 7.77-7.69 (m, 3H), 7.58 (s, 4H), 7.45 (d, J=8.4 Hz, 2H), 6.74 (d, J=7.0 Hz, 1H), 4.33 (d, J=11.6 Hz, 1H), 3.88-3.66 (m, 2H), 3.26 (s, 3H), 2.26 (d, J=5.8 Hz, 1H), 2.09-1.94 (m, 2H), 1.82 (s, 1H). Analytical HPLC: RT=1.78 min (Method B).

Example 44. 1-(1-(4-(2-methylpyridin-3-yl)phenyl)-2-oxopiperidin-3-yl)-3-(4-(trifluoromethyl)phenyl)urea

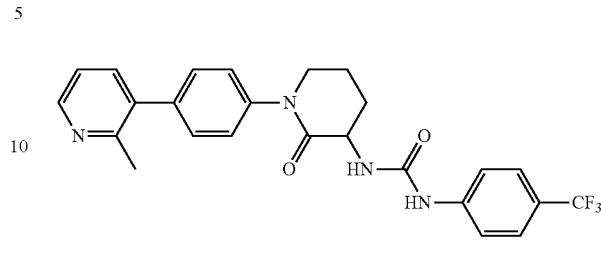

MS(ESI) m/z 468.9 (M+H). ¹H NMR (500 MHz, DMSO-d₆) δ 9.24 (s, 1H), 8.66 (d, J=4.8 Hz, 1H), 8.11 (d, J=7.7 Hz, 1H), 7.69 (t, J=6.4 Hz, 1H), 7.61-7.34 (m, 8H), 6.73 (d, J=6.7 Hz, 1H), 4.48-4.33 (m, 1H), 3.85-3.70 (m, 2H), 2.66-2.54 (s, 3H), 2.29 (m, 1H), 2.01 (m, 2H), 1.87 (m, 1H). Analytical HPLC: RT=1.9 min (Method B).

Example 45. 1-(1-(4-(3-methylpyridin-4-yl)phenyl)-2-oxopiperidin-3-yl)-3-(4-(trifluoromethyl)phenyl)urea

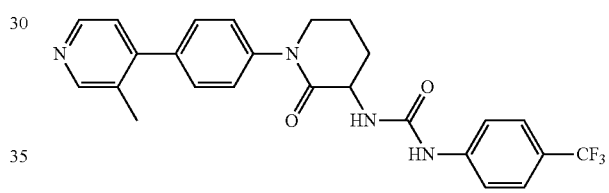

MS(ESI) m/z 469.1 (M+H). ¹H NMR (500 MHz, DMSO-d₆) δ 9.28 (s, 1H), 8.62-8.37 (m, 2H), 7.71-7.52 (m, 4H), 7.45 (d, J=2.3 Hz, 4H), 7.26 (d, J=4.8 Hz, 1H), 6.76 (d, J=6.6 Hz, 1H), 4.42-4.29 (m, 1H), 3.86-3.66 (m, 2H), 2.28 (m, 4H), 2.01 (m, 2H), 1.90-1.77 (m, 1H). Analytical HPLC: RT=1.76 min (Method B).

Example 46. 1-(1-(4'-cyano-[1,1'-biphenyl]-4-yl)-2-oxopiperidin-3-yl)-3-(4-(trifluoromethyl)phenyl)urea

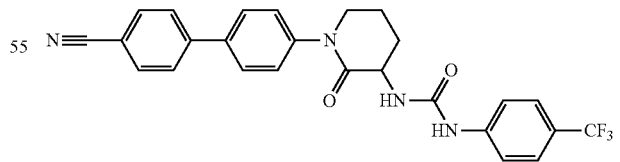

MS(ESI) m/z 479.2 (M+H). ¹H NMR (500 MHz, DMSO-d₆) δ 9.24 (s, 1H), 8.03-7.86 (m, 4H), 7.78 (d, J=8.3 Hz, 2H), 7.65-7.53 (m, 4H), 7.46 (d, J=8.3 Hz, 2H), 6.73 (d, J=6.7 Hz, 1H), 4.47-4.28 (m, 1H), 3.81-3.62 (m, 1H), 3.55-3.32 (m, 1H), 2.32-2.21 (m, 1H), 2.09-1.97 (m, 2H), 1.92-1.64 (m, 1H). Analytical HPLC: RT=2 min (Method A).

Example 47. 1-(1-(4-(4-methylpyridin-3-yl)phenyl)-2-oxopiperidin-3-yl)-3-(4-(trifluoromethyl)phenyl)urea

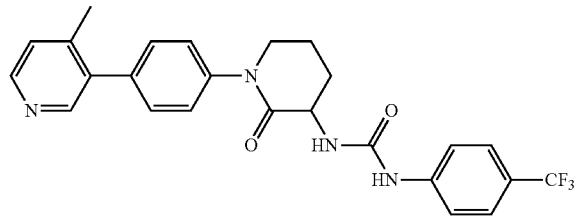 [SMILES: Cc1ccncc1-c1ccc(N2CCCC(NC(=O)Nc3ccc(C(F)(F)F)cc3)C2=O)cc1]

MS(ESI) m/z 468.9 (M+H). ¹H NMR (500 MHz, DMSO-$d_6$) δ 9.26 (s, 1H), 8.55-8.37 (m, 2H), 7.59 (s, 4H), 7.49-7.40 (m, 4H), 7.26 (d, J=4.8 Hz, 1H), 6.74 (d, J=6.5 Hz, 1H), 4.44-4.25 (m, 1H), 3.82-3.71 (m, 1H), 3.71-3.50 (m, 1H), 2.28 (s, 3H), 2.01 (m, 2H), 1.89-1.56 (m, 2H). Analytical HPLC: RT=1.83 min (Method B).

Example 48. 4'-(2-oxo-3-(3-(4-(trifluoromethyl)phenyl)ureido)piperidin-1-yl)-[1,1'-biphenyl]-4-carboxamide

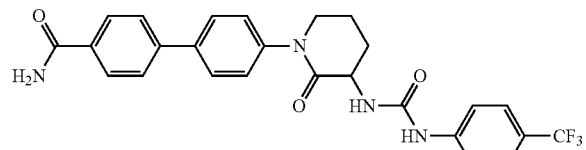

MS(ESI) m/z 497.1 (M+H). ¹H NMR (500 MHz, DMSO-$d_6$) δ 9.24 (s, 1H), 8.05 (br. s., 1H), 7.96 (d, J=8.0 Hz, 2H), 7.83-7.72 (m, 4H), 7.68-7.54 (m, 4H), 7.47-7.35 (m, 3H), 6.72 (d, J=6.6 Hz, 1H), 4.46-4.33 (m, 1H), 3.88-3.65 (m, 2H), 2.30 (m, 1H), 2.01 (m, 2H), 1.84 (m, 1H). Analytical HPLC: RT=1.61 min (Method B).

Example 49. 1-(1-(4'-(methylsulfonyl)-[1,1'-biphenyl]-4-yl)-2-oxopiperidin-3-yl)-3-(4-(trifluoromethyl)phenyl)urea

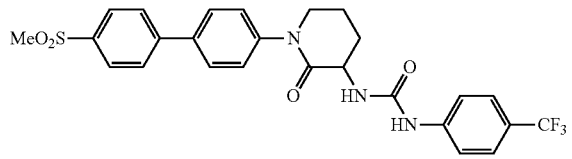 [SMILES: CS(=O)(=O)c1ccc(-c2ccc(N3CCCC(NC(=O)Nc4ccc(C(F)(F)F)cc4)C3=O)cc2)cc1]

MS(ESI) m/z 532 (M+H). ¹H NMR (500 MHz, DMSO-$d_6$) δ 9.59 (br. s., 1H), 8.09-7.94 (m, 4H), 7.80 (d, J=8.3 Hz, 2H), 7.70-7.43 (m, 6H), 7.10 (br. s., 1H), 4.41-4.28 (m, 1H), 3.94-3.63 (m, 2H), 2.63-2.49 (s, 3H), 2.32-2.22 (m, 1H), 2.02 (m, 2H), 1.90-1.77 (m, 1H). Analytical HPLC: RT=1.71 min (Method A).

Example 50. 2'-cyano-5-fluoro-N-methyl-4'-(2-oxo-3-(3-(4-(trifluoromethyl)phenyl)ureido)piperidin-1-yl)-[1,1'-biphenyl]-2-carboxamide

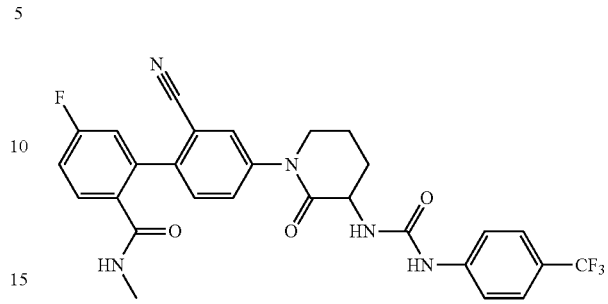

MS(ESI) m/z 554 (M+H). ¹H NMR (500 MHz, DMSO-$d_6$) δ 8.15 (d, J=4.6 Hz, 1H), 7.87 (d, J=8.2 Hz, 2H), 7.66 (d, J=8.2 Hz, 2H), 7.55 (dd, J=8.4, 6.0 Hz, 1H), 7.35-7.23 (m, 1H), 7.20 (dd, J=9.8, 2.1 Hz, 1H), 7.10 (d, J=8.5 Hz, 1H), 6.99-6.79 (m, 2H), 6.32 (s, 2H), 4.32 (d, J=7.3 Hz, 1H), 3.14 (d, J=6.4 Hz, 2H), 2.58 (d, J=4.6 Hz, 3H) 2.03-1.59 (m, 4H). Analytical HPLC: RT=1.74 min (Method A).

Example 51. 5-fluoro-N-methyl-4'-(2-oxo-3-(3-(4-(trifluoromethyl)phenyl)ureido)piperidin-1-yl)-[1,1'-biphenyl]-2-carboxamide

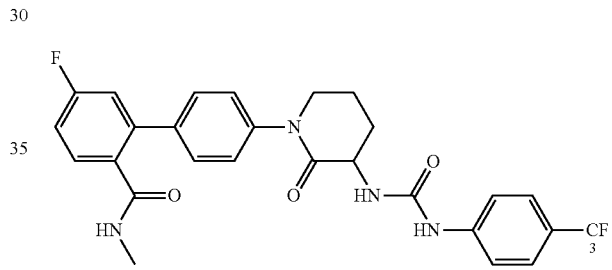

MS(ESI) m/z 528.8 (M+H). ¹H NMR (500 MHz, DMSO-$d_6$) δ 9.22 (s, 1H), 8.15 (d, J=4.6 Hz, 1H), 7.59 (s, 4H), 7.49-7.09 (m, 7H), 6.69 (d, J=6.8 Hz, 1H), 4.44-4.24 (m, 1H), 3.86-3.53 (m, 2H), 2.88 (s, 3H), 2.28 (dd, J=12.1, 5.7 Hz, 1H), 2.07-1.94 (m, 2H), 1.86-1.69 (m, 1H). Analytical HPLC: RT=1.69 min (Method B).

Example 52. 1-(1-(2'-(morpholine-4-carbonyl)-[1,1'-biphenyl]-4-yl)-2-oxopiperidin-3-yl)-3-(4-(trifluoromethyl)phenyl)urea

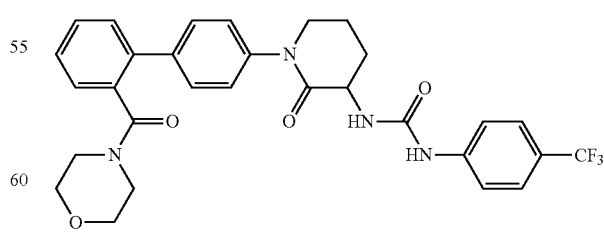

MS(ESI) m/z 567.2 (M+H). ¹H NMR (500 MHz, DMSO-$d_6$) δ 9.22 (s, 1H), 7.68-7.26 (m, 12H), 6.81-6.59 (m, 1H), 4.34 (br. s., 1H), 3.74-3.49 (m, 2H), 3.31-3.05 (m, 2H), 3.00-2.87 (m, 2H), 2.80-2.63 (m, 2H), 2.42 (d, J=11.4 Hz,

1H), 2.28 (d, J=5.8 Hz, 1H), 2.08-1.95 (m, 2H), 1.89-1.72 (m, 2H). Analytical HPLC: RT=1.88 min (Method B).

Example 53. 1-(1-(4-(2-methoxypyridin-3-yl)phenyl)-2-oxopiperidin-3-yl)-3-(4-(trifluoromethyl)phenyl)urea

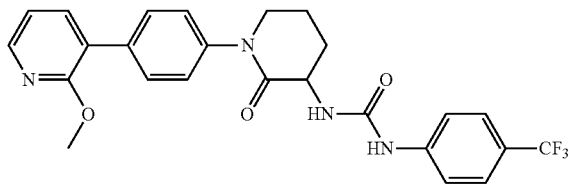 [SMILES: COc1ncccc1-c1ccc(N2CCCC(NC(=O)Nc3ccc(C(F)(F)F)cc3)C2=O)cc1]

MS(ESI) m/z 484.9 (M+H). $^1$H NMR (500 MHz, DMSO-$d_6$) δ 9.21 (s, 1H), 8.26-8.10 (m, 1H), 7.85-7.72 (m, 1H), 7.66-7.52 (m, 6H), 7.35 (d, J=8.4 Hz, 2H), 7.15-6.94 (m, 1H), 6.77-6.63 (m, 1H), 4.40-4.25 (m, 1H), 3.87 (s, 3H), 3.73-3.58 (m, 2H), 2.31-2.21 (m, 1H), 2.10-1.96 (m, 2H), 1.87-1.68 (m, 1H). Analytical HPLC: RT=2.01 min (Method B).

Example 54. N-methyl-4'-(2-oxo-3-(3-(4-(trifluoromethyl)phenyl)ureido)piperidin-1-yl)-[1,1'-biphenyl]-2-carboxamide

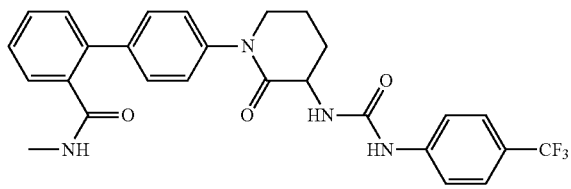

Example 54A. methyl 4'-(2-oxo-3-(3-(4-(trifluoromethyl)phenyl)ureido)piperidin-1-yl)-[1,1'-biphenyl]-2-carboxylate

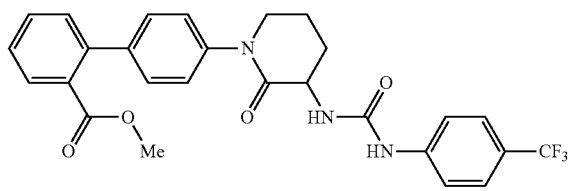 [SMILES: COC(=O)c1ccccc1-c1ccc(N2CCCC(NC(=O)Nc3ccc(C(F)(F)F)cc3)C2=O)cc1]

Example 54A was synthesized from Example 3A and 2-(methoxycarbonyl)phenyl)boronic acid in a route similar to that described in preparing Example 3. MS (ESI) m/z 512.5 (M+H).

Example 54B. 4'-(2-oxo-3-(3-(4-(trifluoromethyl)phenyl)ureido)piperidin-1-yl)-[1,1'-biphenyl]-2-carboxylic acid

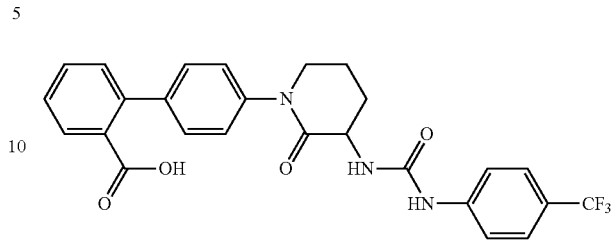

To a solution of Example 54A (100 mg, 0.20 mmol) in THF (1.0 mL), MeOH (1.0 mL) and H$_2$O (0.20 mL) was added LiOH—H$_2$O (41 mg, 0.98 mmol). The reaction mixture was stirred overnight at RT. The reaction solution was diluted with EtOAc and 1N HCl, the layers were separated, and the aqueous layer extracted with EtOAc (2×). The combined extracts were washed with brine, dried over Na$_2$SO$_4$, and concentrated to give the crude product (80 mg, 0.16 mmol). MS (ESI) m/z 498.4 (M+H).

Example 54

A mixture of Example 54B (40 mg, 0.080 mmol), methanamine (0.015 mL, 0.40 mmol), HATU (61 mg, 0.16 mmol) and Et$_3$N (0.11 mL, 0.80 mmol) in DMF (1.0 mL) was stirred at RT for 5 h. The reaction solution was filtered and the product was purified via reverse phase prep HPLC to give the title compound, (2.0 mg, 0.0038 mmol). MS (ESI) m/z 511.0 (M+H). $^1$H NMR (500 MHz, DMSO-d6) δ 9.29 (s, 1H), 8.18-8.07 (m, 1H), 7.61 (m, 5H), 7.36 (m, 7H), 6.86-6.65 (m, 1H), 4.46-4.31 (m, 1H), 3.81-3.63 (m, 2H), 3.16 (m, 1H), 2.59 (s, 3H), 2.37-2.24 (m, 1H), 2.01 (m, 2H). Analytical HPLC: RT=1.649 min (Method A).

Example 55. N,N-dimethyl-4'-(2-oxo-3-(3-(4-(trifluoromethyl)phenyl)ureido)piperidin-1-yl)-[1,1'-biphenyl]-2-carboxamide

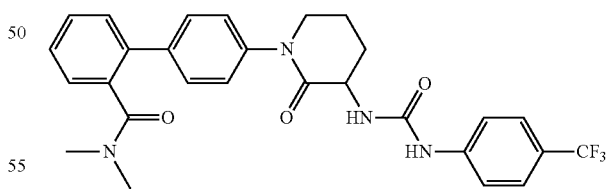

Example 55 was synthesized using the procedures described in Example 54. MS(ESI) m/z 525.2 (M+H). $^1$H NMR (500 MHz, DMSO-d$_6$) δ 9.58 (s, 1H), 7.79-7.29 (m, 12H), 7.10 (d, J=6.4 Hz, 1H), 4.46-4.28 (m, 1H), 3.80-3.57 (m, 2H), 2.79 (s, 3H), 2.47 (s, 3H), 2.27 (d, J=6.1 Hz, 1H), 2.00 (m, 2H), 1.91-1.76 (m, 1H). Analytical HPLC: RT=1.76 min (Method A).

Example 56. 4'-(3-(3-(4-chlorophenyl)ureido)-2-oxopiperidin-1-yl)-N-methyl-[1,1'-biphenyl]-2-carboxamide

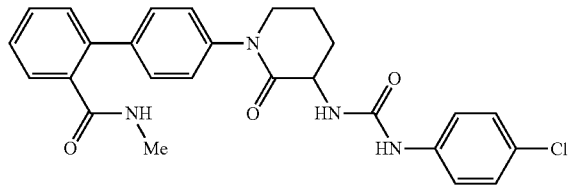 [SMILES: CNC(=O)c1ccccc1-c1ccc(N2CCCC(NC(=O)Nc3ccc(Cl)cc3)C2=O)cc1]

Example 56A. 4'-(3-((tert-butoxycarbonyl)amino)-2-oxopiperidin-1-yl)-[1,1'-biphenyl]-2-carboxylic acid

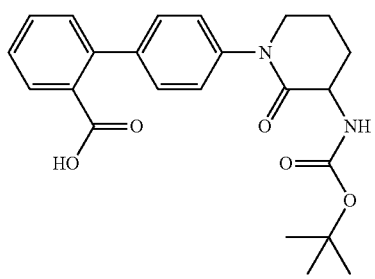 [SMILES: CC(C)(C)OC(=O)NC1CCCN(c2ccc(-c3ccccc3C(=O)O)cc2)C1=O]

Example 56A was prepared from 1-chloro-4-iodobenzene and 2-boronobenzoic acid in a route similar to that described in preparing Example 1A and Example 1B. MS (ESI) m/z 411.3 (M+H).

Example 56B. tert-butyl (1-(2'-(methylcarbamoyl)-[1,1'-biphenyl]-4-yl)-2-oxopiperidin-3-yl)carbamate

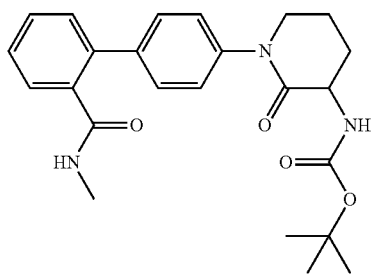 [SMILES: CNC(=O)c1ccccc1-c1ccc(N2CCCC(NC(=O)OC(C)(C)C)C2=O)cc1]

Example 56B was prepared from Example 56A using the amide coupling conditions described in preparing Example 4. MS (ESI) m/z 424.3 (M+H).

Example 56C. 4'-(3-amino-2-oxopiperidin-1-yl)-N-methyl-[1,1'-biphenyl]-2-carboxamide

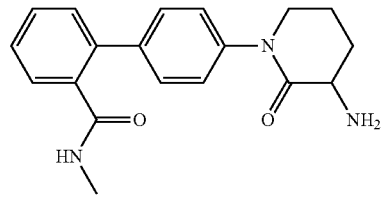 [SMILES: CNC(=O)c1ccccc1-c1ccc(N2CCCC(N)C2=O)cc1]

Example 56C was prepared from Example 56B using deprotection conditions described in preparing Example 1C. MS (ESI) m/z 324.1 (M+H).

Example 56 was prepared from Example 5C and 1-chloro-4-isocyanatobenzene using conditions described in preparing Example 1. MS (ESI) m/z 477.4 (M+H).

Example 57: (R)-1-(1-(4-(2-fluoropyridin-3-yl)phenyl)-2-oxopiperidin-3-yl)-3-(4-(trifluoromethyl)phenyl)urea

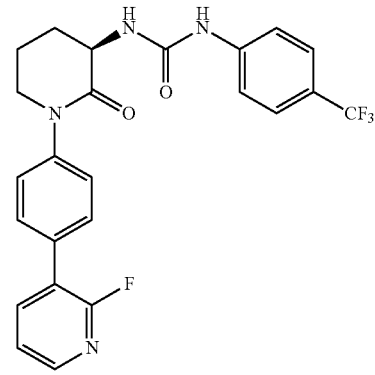 [SMILES: O=C(Nc1ccc(C(F)(F)F)cc1)N[C@@H]1CCCN(c2ccc(-c3cccnc3F)cc2)C1=O]

To a solution of Intermediate 1 in 1,4-dioxane (2 mL) were added potassium phosphate, tribasic (23 mg, 0.13 mmol) and (2-fluoropyridin-3-yl)boronic acid (11 mg, 0.079 mmol). The reaction mixture was purged with nitrogen for 5 min and charged with Pd(dppf)Cl$_2$.DCM adduct (5.4 mg, 6.6 μmol). The reaction mixture was again purged with nitrogen for 3 min and heated at 60° C. for 15 h. The mixture was cooled, filtered through celite pad and the filtrate was concentrated under reduced pressure to yield the crude product which was purified by reverse phase chromatography to afford the title compound (11 mg, 34%, 0.023 mmol) as a off white solid. MS(ESI) m/z: 473.1 (M+H); $^1$H NMR (400 MHz, DMSO-d$_6$): δ 9.22 (s, 1H), 8.25 (d, J=5.14 Hz, 1H), 8.18-8.11 (m, 1H), 7.68-7.56 (m, 6H), 7.51-7.44 (m, 3H), 6.70 (d, J=6.60 Hz, 1H), 4.41-4.34 (m, 1H), 3.82-3.68 (m, 2H), 2.35-2.28 (m, 1H), 2.06-1.98 (m, 2H), 1.89-1.79 (m, 1H). Analytical HPLC: RT=2.08 min, (Method F).

The following examples in Table 2 were made by using analogous procedures to those shown in Example 57 from Intermediates 1-3 using the appropriate boronic acids.

TABLE 2

| Ex | Structure | LCMS (M + H)+ | HPLC Method, RT (min.) & Purity | 1H NMR |
|---|---|---|---|---|
| 58 | [structure: 2'-(hydroxymethyl)biphenyl-4-yl piperidinone urea with 4-trifluoromethylphenyl, (S)] | 484.2 | Method E, RT = 1.80 min, 97.6% | 1H NMR (400 MHz, DMSO-d6): δ 9.23 (s, 1H), 7.64-7.54 (m, 5H), 7.44-7.29 (m, 6H), 7.24 (dd, J = 7.5, 1.5 Hz, 1H), 6.69 (d, J = 6.5 Hz, 1H), 5.14 (t, J = 5.3 Hz, 1H), 4.45-4.30 (m, 3H), 3.83-3.68 (m, 2H), 2.37-2.27 (m, 1H), 2.09-1.96 (m, 2H), 1.89-1.75 (m, 1H) |
| 59 | [structure: 2'-methoxybiphenyl-4-yl piperidinone urea with 4-trifluoromethylphenyl, (S)] | 484.2 | Method E, RT = 2.12 min, 96.3% | 1H NMR (400 MHz, DMSO-d6): δ 9.22 (s, 1H), 7.64-7.54 (m, 4H), 7.52-7.46 (m, 2H), 7.38-7.27 (m, 4H), 7.12 (d, J = 7.5 Hz, 1H), 7.06-6.99 (m, 1H), 6.69 (d, J = 7.0 Hz, 1H), 4.39-4.30 (m, 1H), 3.80-3.66 (m, 5H), 2.36-2.30 (m, 1H), 2.06-1.95 (m, 2H), 1.89-1.72 (m, 1H) |
| 60 | [structure: 2'-carboxybiphenyl-4-yl piperidinone urea with 4-trifluoromethylphenyl, (S)] | 498.2 | Method E, RT = 1.79 min, 98% | 1H NMR (400 MHz, DMSO-d6): δ 9.50 (br. s., 1H), 7.65-7.50 (m, 5H), 7.46-7.27 (m, 6H), 6.99 (d, J = 6.0 Hz, 1H), 6.72 (br. s., 1H), 6.31-6.30 (m, 1H), 4.41-4.28 (m, 1H), 3.75-3.64 (m, 2H), 2.29 (m, 1H), 2.05-1.94 (m, 2H), 1.88-1.73 (m, 1H) |
| 61 | [structure: 2'-carbamoylbiphenyl-4-yl piperidinone urea with 4-trifluoromethylphenyl, (R)] | 497.1 | Method F, RT = 1.811 min, 99.2% | 1H NMR (400 MHz, DMSO-d6): δ 9.23 (s, 1H), 7.69 (s, 1H), 7.63-7.55 (m, 4H), 7.51-7.29 (m, 9H), 6.69 (d, J = 6.60 Hz, 1H), 4.39-4.33 (s, 1H), 3.79-3.69 (m, 2H), 2.36-2.28 (m, 1H), 2.05-1.97 (m, 2H), 1.87-1.75 (m, 1H). |
| 62 | [structure: 4-(pyridin-4-yl)phenyl piperidinone urea with 4-trifluoromethylphenyl, (R)] | 455.2 | Method F, RT = 1.664 min, 99.8% | 1H NMR (400 MHz, DMSO-d6): δ 9.26 (s, 1H), 8.83 (d, J = 6.40 Hz, 2H), 8.15 (d, J = 6.40 Hz, 2H), 8.00 (d, J = 8.40 Hz, 2H), 7.63-7.59 (m, 4H), 7.55 (d, J = 8.80 Hz, 2H), 6.74 (d, J = 6.80 Hz, 1H), 4.42-4.36 (m, 1H), 3.84-3.71 (m, 2H), 2.33-2.27 (m, 1H), 2.06-1.99 (m, 2H), 1.90-1.82 (m, 1H). |

TABLE 2-continued

| Ex | Structure | LCMS (M + H)+ | HPLC Method, RT (min.) & Purity | 1H NMR |
|---|---|---|---|---|
| 63 | 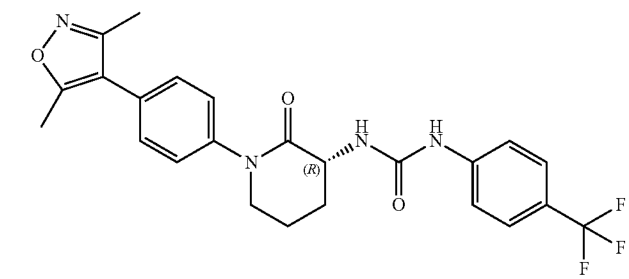 | 473.1 | Method F, RT = 2.072 min, 95.2% | ¹H NMR (400 MHz, DMSO-d₆): δ 9.21 (s, 1H), 7.65-7.55 (m, 4 H), 7.42 (s, 4 H), 6.68 (d, J = 6.85 Hz, 1H), 4.40-4.30 (m, 1H), 3.80-3.67 (m, 2H), 2.42 (s, 3H), 2.34-2.29 (m, 1H), 2.24 (s, 3H), 1.95-2.05 (m, 2H), 1.90-1.76 (m, 1H). |
| 64 | 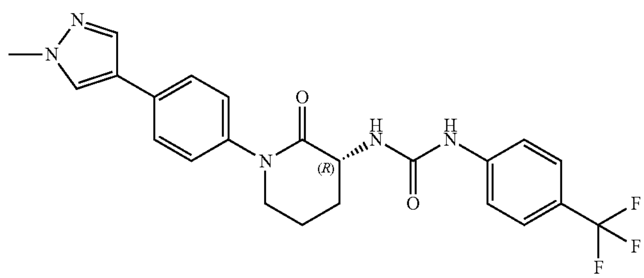 | 458.1 | Method F, RT = 1.858 min, 99.1% | ¹H NMR (400 MHz, DMSO-d₆): δ 9.22 (s, 1H), 8.13 (s, 1H), 7.86 (s, 1H), 7.54-7.64 (m, 6H), 7.28 (d, J = 8.56 Hz, 2H), 6.68 (d, J = 6.60 Hz, 1H), 4.38-4.29 (m, 1H), 3.86 (s, 3H), 3.76-3.61 (m, 2H), 2.31 (m, 1H), 2.03-1.94 (m, 2H), 1.86-1.74 (m, 1H). |
| 65 | 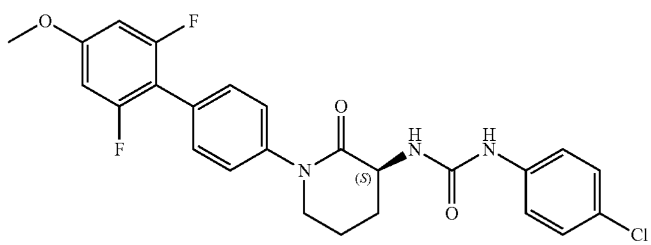 | 486.0 | Method F, RT = 2.284 min, 99.5% | ¹H NMR (400 MHz, DMSO-d₆): δ 8.94-8.91 (m, 1H) 7.46-7.38 (m, 6H) 7.30-7.24 (m, 2H) 6.90-6.83 (m, 2H) 6.59-6.54 (m, 1H) 4.38-4.29 (m, 1H) 4.06-4.03 (s, 3H) 3.80-3.66 (m, 2H) 2.35-2.24 (m, 1H) 2.05-1.96 (m, 2H) 1.88-1.74 (m, 1H) |
| 66 | 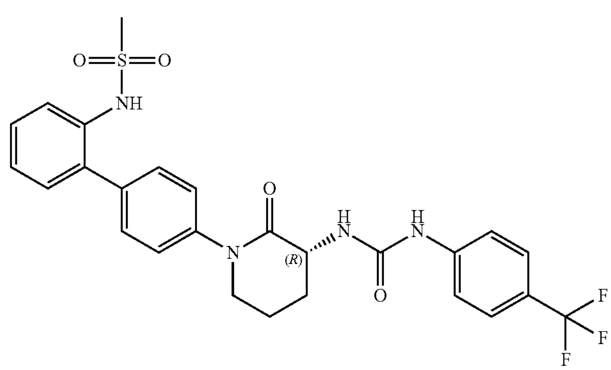 | 547.2 | Method F, RT = 1.83 min, 96.8% | ¹H NMR (400 MHz, DMSO-d₆): δ 9.22 (s, 1H), 7.65-7.56 (m, 3H), 7.53-7.47 (m, 2H), 7.46-7.32 (m, 7H), 6.70 (d, J = 7.0 Hz, 1H), 6.27 (s, 1H), 4.42-4.31 (m, 1H), 3.82-3.67 (m, 2H), 2.73 (s, 3H), 2.33-2.28 (m, 1H), 2.01 (m, 2H), 1.84 (m, 1H). |
| 67 | 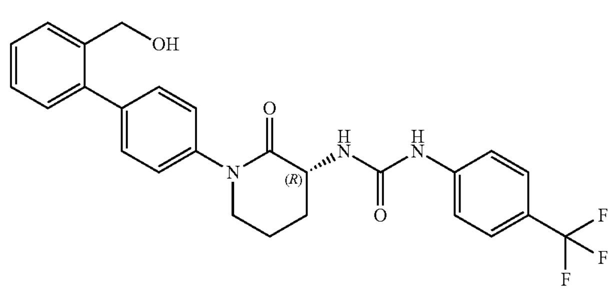 | 484.2 | Method F, RT = 1.804 min, 98.6% | ¹H NMR (400 MHz, DMSO-d₆): δ 9.23 (s, 1H), 7.65-7.54 (m, 5H), 7.45-7.30 (m, 6H), 7.28-7.21 (m, 1H), 6.70 (d, J = 6.5 Hz, 1H), 5.18-5.11 (m, 1H), 4.45-4.31 (m, 3H), 3.83-3.68 (m, 2H), 2.32-2.27 (m, 1H), 2.06-1.97 (m, 2H), 1.89-1.78 (m, 1H) |

TABLE 2-continued

| Ex | Structure | LCMS (M + H)+ | HPLC Method, RT (min.) & Purity | 1H NMR |
|---|---|---|---|---|
| 68 | 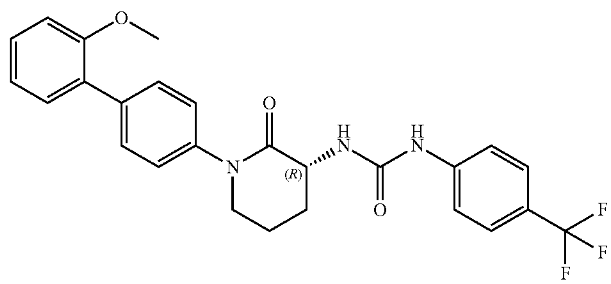 | 484.2 | Method E, RT = 2.132 min, 94.5% | ¹H NMR (400 MHz, DMSO-d₆): δ 9.22 (s, 1H), 7.64-7.55 (m, 4H), 7.52-7.46 (m, 2H), 7.38-7.28 (m, 4H), 7.12 (d, J = 8.5 Hz, 1H), 7.03 (td, J = 7.5, 1.0 Hz, 1H), 6.69 (d, J = 7.0 Hz, 1H), 4.39-4.29 (m, 1H), 3.80-3.67 (m, 5H), 2.32-2.26 (m, 1H), 2.05-1.97 (m, 2H), 1.83 (m, 1H) |
| 69 | 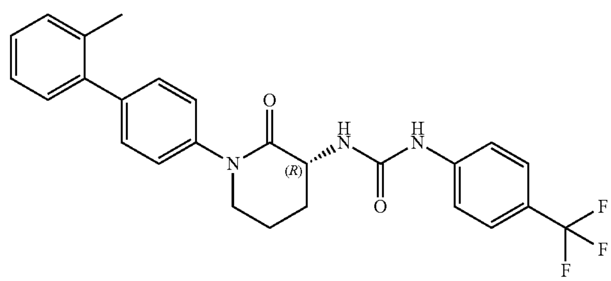 | 468.2 | Method E, RT = 2.227 min, 98.4% | ¹H NMR (400 MHz, DMSO-d₆): δ 9.23 (s, 1H), 7.64-7.54 (m, 4H), 7.41-7.34 (m, 4H), 7.32-7.18 (m, 4H), 6.70 (d, J = 7.0 Hz, 1H), 4.41-4.30 (m, 1H), 3.83-3.66 (m, 2H), 2.32-2.27 (m, 1H), 2.26 (s, 3H), 2.05-1.96 (m, 2H), 1.84 (m, 1H) |
| 70 | 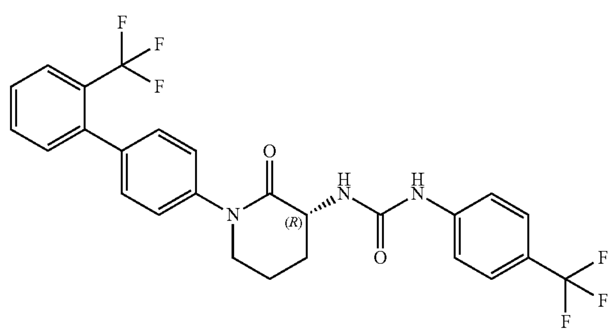 | 522.2 | Method F, RT = 2.25 min, 96.6% | ¹H NMR (400 MHz, METHANOL-d₄): δ 7.78 (d, J = 8.0 Hz, 1H), 7.67-7.62 (m, 1H), 7.60-7.50 (m, 5H), 7.41-7.33 (m, 5H), 4.45 (dd, J = 11.5, 6.0 Hz, 1H), 3.92-3.73 (m, 2H), 2.47-2.37 (m, 1H), 2.19-2.09 (m, 2H), 2.05-1.92 (m, 1H) |
| 71 | 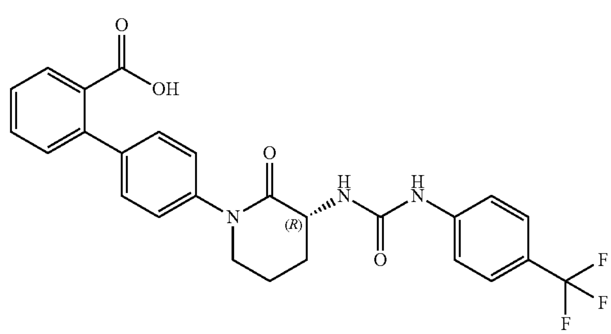 | 498.2 | Method F, RT = 1.286 min, 94.9% | ¹H NMR (400 MHz, METHANOL-d₄): δ 7.67 (d, J = 6.5 Hz, 1H), 7.60-7.51 (m, 4H), 7.51-7.43 (m, 3H), 7.41-7.30 (m, 4H), 4.45 (dd, J = 11.5, 6.0 Hz, 1H), 3.88-3.70 (m, 2H), 2.48-2.37 (m, 1H), 2.17-2.08 (m, 2H), 1.98 (m, 1H) |

TABLE 2-continued

| Ex | Structure | LCMS (M + H)+ | HPLC Method, RT (min.) & Purity | 1H NMR |
|---|---|---|---|---|
| 72 | 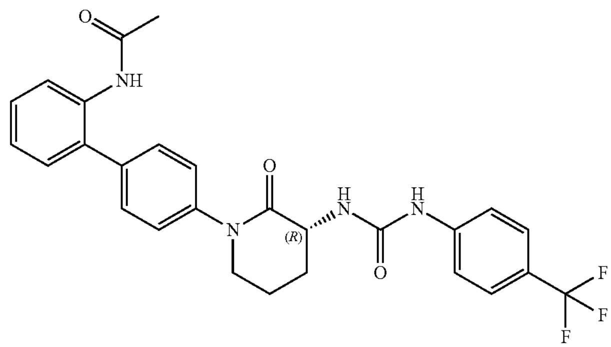 | 511.2 | Method F, RT = 1.712 min, 93.5% | ¹H NMR (400 MHz, DMSO-d₆): δ 9.31 (s, 1H), 7.65-7.53 (m, 5H), 7.47-7.24 (m, 8H), 6.80 (d, J = 7.0 Hz, 1H), 4.42-4.29 (m, 1H), 3.73 (tq, J = 12.1, 6.0 Hz, 2H), 2.33-2.25 (m, 1H), 2.06-1.95 (m, 2H), 1.88-1.76 (m, 4H). |
| 73 | 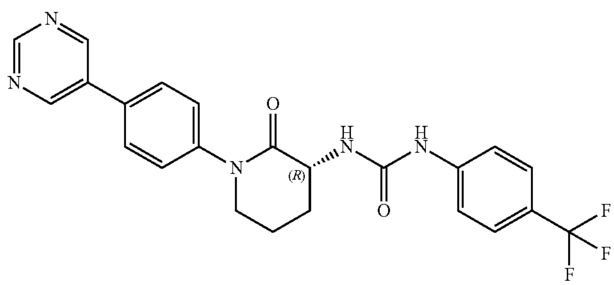 | 456.2 | Method E, RT = 1.532 min, 97.5% | ¹H NMR (400 MHz, DMSO-d₆): δ 9.24-9.14 (m, 3H), 7.88-7.82 (m, 2H), 7.65-7.54 (m, 4H), 7.52-7.45 (m, 2H), 6.70 (d, J = 7.0 Hz, 1H), 6.26 (s, 1H), 4.36 (m, 1H), 3.75 (d, J = 16.6 Hz, 2H), 2.32 (m, 1H), 2.01 (m, 2H), 1.84 (m, 1H) |
| 74 | 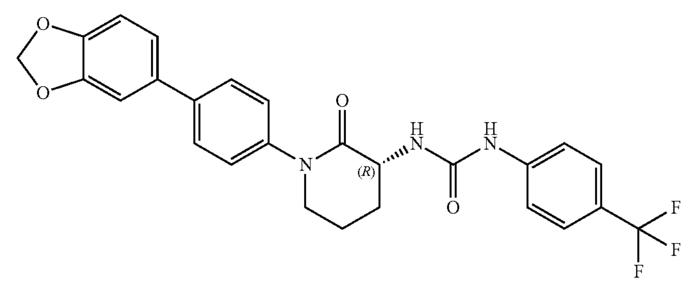 | 498.2 | Method F, RT = 2.064 min, 91.9% | ¹H NMR (400 MHz, DMSO-d₆): δ 9.21 (s, 1H), 7.66-7.54 (m, 6H), 7.39-7.32 (m, 2H), 7.26 (d, J = 1.5 Hz, 1H), 7.16 (dd, J = 8.3, 1.8 Hz, 1H), 7.00 (d, J = 8.5 Hz, 1H), 6.69 (d, J = 6.5 Hz, 1H), 6.06 (s, 2H), 4.40-4.29 (m, 1H), 3.71 (dt, J = 16.6, 6.5 Hz, 2H), 2.29 (m, 1H), 2.07-1.94 (m, 2H), 1.82 (m, 1H) |
| 75 | 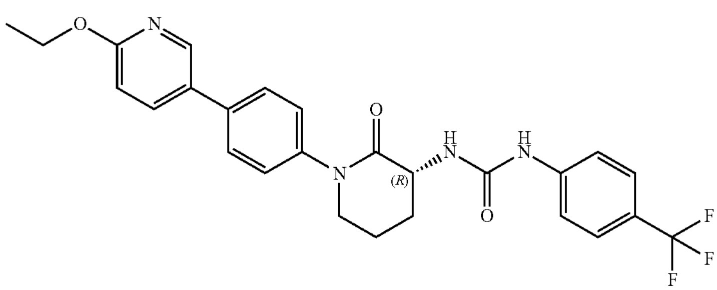 | 499.2 | Method E, RT = 1.975 min, 97.8% | ¹H NMR (400 MHz, DMSO-d₆): δ 9.22 (s, 1H), 8.48 (d, J = 2.5 Hz, 1H), 8.05-7.98 (m, 1H), 7.72-7.64 (m, 2H), 7.63-7.55 (m, 4H), 7.43-7.36 (m, 2H), 6.92-6.85 (m, 1H), 6.69 (d, J = 6.5 Hz, 1H), 4.41-4.29 (m, 3H), 3.81-3.64 (m, 2H), 2.32-2.27 (m, 1H), 2.07-1.96 (m, 2H), 1.88-1.74 (m, 1H), 1.37-1.30 (m, 3H) |
| 76 | 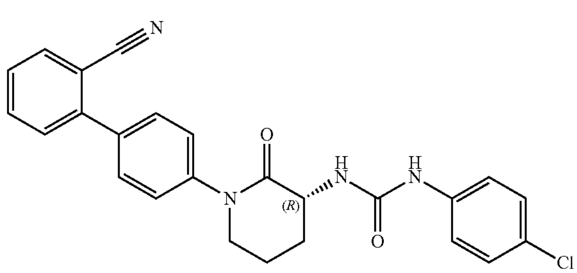 | 445.2 | Method C, RT = 1.85 min, 96.9% | ¹H NMR (400 MHz, DMSO-d₆): δ 8.92 (s, 1H), 7.98-7.92 (m, 1H), 7.84-7.75 (m, 1H), 7.67-7.54 (m, 4H), 7.51-7.39 (m, 4H), 7.29-7.23 (m, 2H), 6.56 (d, J = 6.8 Hz, 1H), 4.41-4.30 (m, 1H), 3.84-3.65 (m, 2H), 2.31-2.24 (m, 1H), 2.05-1.94 (m, 2H), 1.88-1.73 (m, 1H) |

TABLE 2-continued

| Ex | Structure | LCMS (M + H)+ | HPLC Method, RT (min.) & Purity | 1H NMR |
|---|---|---|---|---|
| 77 | 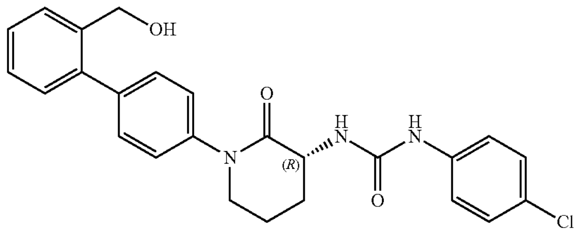 | 450.2 | Method D, RT = 1.67 min, 98.1% | ¹H NMR (400 MHz, DMSO-$d_6$): δ 8.93 (s, 1H), 7.57 (d, J = 7.6 Hz, 1H), 7.47-7.31 (m, 8H), 7.30-7.21 (m, 3H), 6.57 (d, J = 6.6 Hz, 1H), 5.14 (t, J = 5.4 Hz, 1H), 4.42 (d, J = 5.1 Hz, 2H), 4.38-4.27 (m, 1H), 3.82-3.66 (m, 2H), 2.29 (m, 1H), 2.04-1.96 (m, 2H), 1.87-1.75 (m, 1H) |
| 78 | 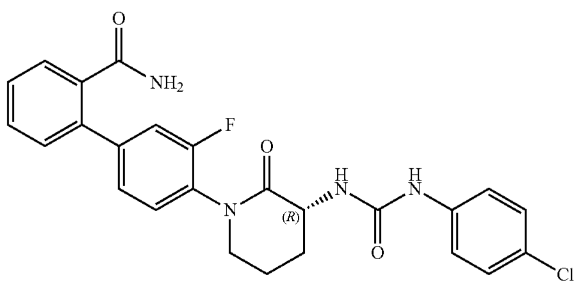 | 481.1 | Method E, RT = 1.708 min, 100.0% | ¹H NMR (400 MHz, DMSO-$d_6$): δ 8.92-8.87 (m, 1H) 7.80-7.76 (m, 1H) 7.53-7.36 (m, 8 H) 7.35-7.24 (m, 4 H) 6.60-6.55 (m, 1H) 4.39-4.31 (m, 1H) 3.68-3.60 (m, 2H) 2.35-2.26 (m, 1H) 2.05-1.97 (m, 2H) 1.88-1.76 (m, 1H) |
| 79 | 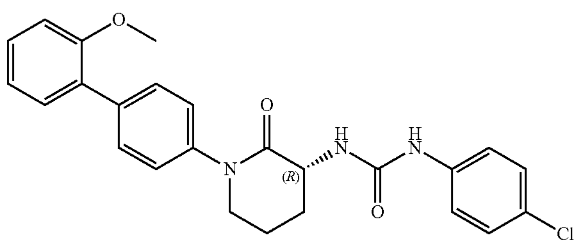 | 450.4 | Method C, RT = 2.007 min, 96.3% | 1H NMR (400 MHz, DMSO-$d_6$): δ 8.93 (s, 1H), 7.52-7.40 (m, 4H), 7.38-7.23 (m, 6H), 7.12 (d, J = 7.3 Hz, 1H), 7.03 (td, J = 7.5, 1.0 Hz, 1H), 6.56 (d, J = 6.4 Hz, 1H), 4.37-4.26 (m, 1H), 3.78 (s, 3H), 3.76-3.66 (m, 2H), 2.29 (m, 1H), 2.05-1.95 (m, 2H), 1.85-1.75 (m, 1H) |
| 80 | 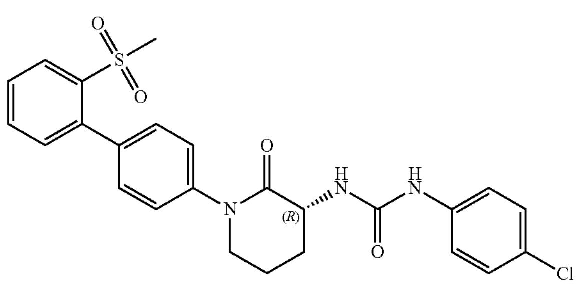 | 498.2 | Method D, RT = 1.673 min, 94.5% | ¹H NMR (400 MHz, DMSO-$d_6$): δ 8.96 (s, 1H), 8.10 (d, J = 9.3 Hz, 1H), 7.81-7.73 (m, 1H), 7.72-7.64 (m, 1H), 7.47-7.37 (m, 7H), 7.27 (d, J = 8.8 Hz, 2H), 6.60 (d, J = 6.8 Hz, 1H), 4.35 (d, J = 11.7 Hz, 1H), 3.84-3.69 (m, 2H), 2.82 (s, 3H), 2.32-2.23 (m, 1H), 2.00 (m, 2H), 1.83 (m, 1H) |
| 81 | 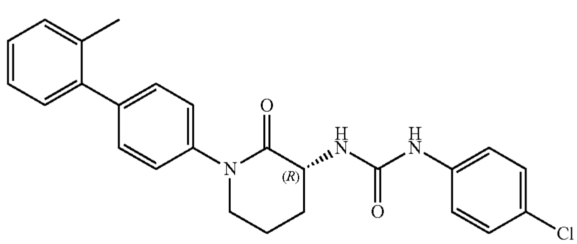 | 434.2 | Method D, RT = 2.12 min, 96.8% | ¹H NMR (400 MHz, DMSO-$d_6$): δ 8.92 (s, 1H), 7.46-7.40 (m, 2H), 7.39-7.32 (m, 4H), 7.31-7.17 (m, 6H), 6.56 (d, J = 6.6 Hz, 1H), 4.38-4.27 (m, 1H), 3.79-3.66 (m, 2H), 2.31-2.26 (m, 1H), 2.25 (s, 3H), 2.03-1.94 (m, 2H), 1.86-1.72 (m, 1H) |

TABLE 2-continued

| Ex | Structure | LCMS (M + H)+ | HPLC Method, RT (min.) & Purity | 1H NMR |
|---|---|---|---|---|
| 82 | 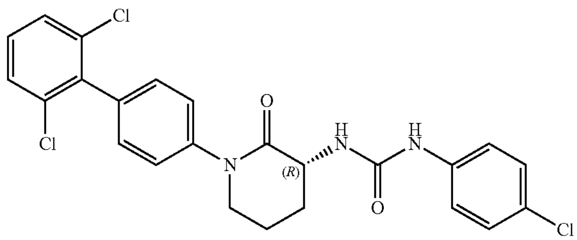 | 489.1 | Method D, RT = 2.173 min, 96.9% | ¹H NMR (400 MHz, DMSO-d₆): δ 8.93 (s, 1H), 7.62-7.56 (m, 2H), 7.48-7.39 (m, 5H), 7.32-7.23 (m, 4H), 6.56 (d, J = 6.8 Hz, 1H), 4.40-4.30 (m, 1H), 3.84-3.69 (m, 2H), 2.32-2.26 (m, 1H), 2.05-1.96 (m, 2H), 1.87-1.74 (m, 1H) |
| 83 | 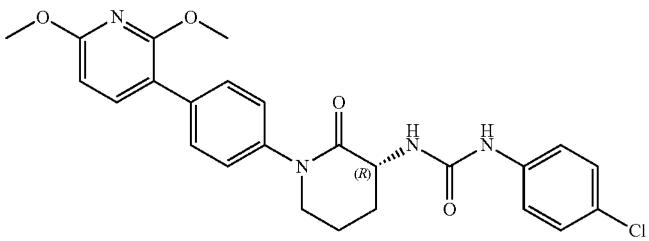 | 481.2 | Method D, RT = 2.097 min, 97.1% | ¹H NMR (400 MHz, DMSO-d₆): δ 8.92 (s, 1H), 7.72 (d, J = 8.1 Hz, 1H), 7.56-7.48 (m, 2H), 7.46-7.38 (m, 2H), 7.35-7.23 (m, 4H), 6.55 (d, J = 6.6 Hz, 1H), 6.48 (d, J = 8.1 Hz, 1H), 4.38-4.26 (m, 1H), 3.90 (d, J = 1 Hz, 6H), 3.77-3.63 (m, 2H), 2.28 (m, 1H), 2.03-1.94 (m, 2H), 1.86-1.72 (m, 1H) |
| 84 | 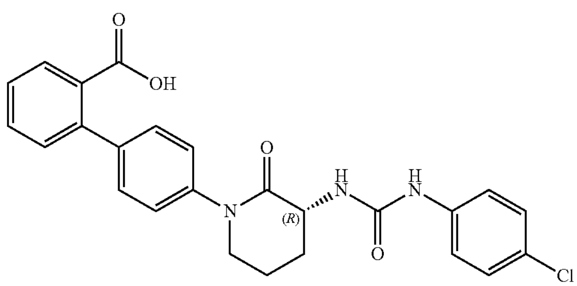 | 464.1 | Method C, RT = 1.658 min, 97.6% | ¹H NMR (400 MHz, DMSO-d₆): δ 9.01 (s, 1H), 7.63 (br. s., 1H), 7.51 (br. s., 1H), 7.47-7.31 (m, 8H), 7.30-7.23 (m, 2H), 6.64 (d, J = 6.6 Hz, 1H), 4.39-4.28 (m, 1H), 3.77-3.66 (m, 2H), 2.33-2.25 (m, 1H), 2.05-1.94 (m, 2H), 1.86-1.71 (m, 1H) |
| 85 | 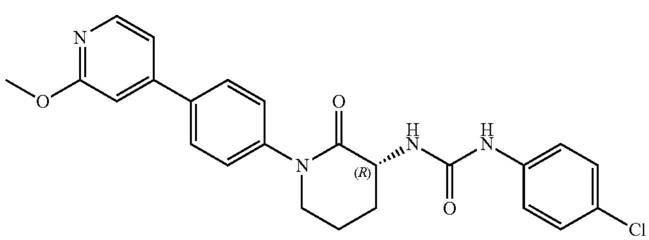 | 451.2 | Method C, RT = 1.537 min, 96.8% | ¹H NMR (400 MHz, DMSO-d₆): δ 8.93 (s, 1H), 8.24 (dd, J = 5.5, 0.6 Hz, 1H), 7.85-7.78 (m, 2H), 7.49-7.41 (m, 4H), 7.34 (dd, J = 5.5, 1.6 Hz, 1H), 7.31-7.24 (m, 2H), 7.13 (dd, J = 1.6, 0.6 Hz, 1H), 6.58 (d, J = 6.6 Hz, 1H), 4.40-4.30 (m, 1H), 3.91 (s, 3H), 3.82-3.66 (m, 2H), 2.32-2.23 (m, 1H), 2.07-1.94 (m, 2H), 1.88-1.75 (m, 1H) |
| 86 | 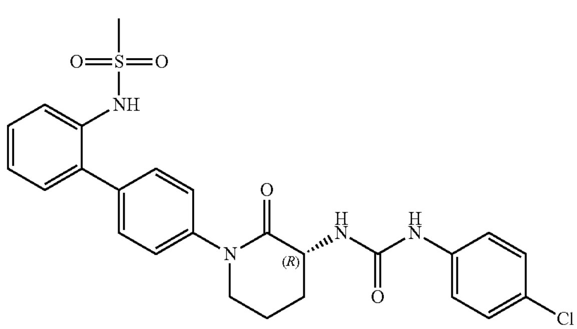 | 513.1 | Method D, RT = 1.705 min, 97.4% | ¹H NMR (400 MHz, DMSO-d₆): δ 9.19 (s, 1H), 7.76 (d, J = 8.6 Hz, 2H), 7.72-7.47 (m, 10H), 6.83 (d, J = 6.8 Hz, 1H), 4.64-4.53 (m, 1H), 4.07-3.92 (m, 2H), 2.96 (s, 3H), 2.58-2.51 (m, 1H), 2.25 (m, 2H), 2.06 (m, 1H) |

TABLE 2-continued

| Ex | Structure | LCMS (M + H)+ | HPLC Method, RT (min.) & Purity | 1H NMR |
|---|---|---|---|---|
| 87 | 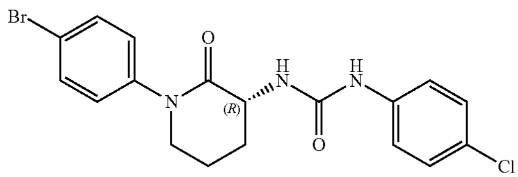 | 423.9 | Method F, RT = 1.975 min, 100.0% | ¹H NMR (400 MHz, DMSO-d₆): δ 8.92-8.88 (m, 1H), 7.61-7.54 (m, 2H), 7.45-7.39 (m, 2H), 7.31-7.24 (m, 4 H), 6.57-6.51 (m, 1H), 4.35-4.26 (m, 1H), 3.75-3.59 (m, 2H), 2.31-2.21 (m, 1H), 2.02-1.92 (m, 2H), 1.85-1.71 (m, 1H). |
| 88 | 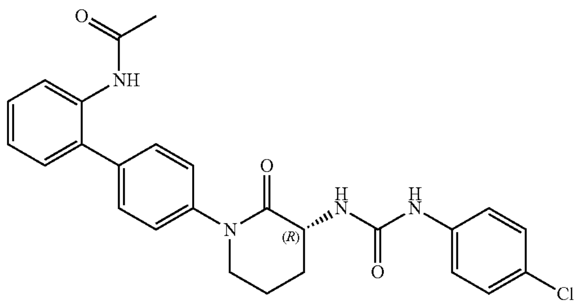 | 477.2 | Method D, RT = 1.565 min, 97.8% | ¹H NMR (400 MHz, DMSO-d₆): δ 9.32 (s, 1H), 8.96 (s, 1H), 7.49-7.22 (m, 12H), 6.64-6.55 (m, 1H), 4.40-4.29 (m, 1H), 3.74 (dq, J = 12.0, 6.1 Hz, 2H), 2.30 (m, 1H), 2.07-1.96 (m, 2H), 1.91 (s, 3H), 1.87-1.73 (m, 1H) |
| 89 | 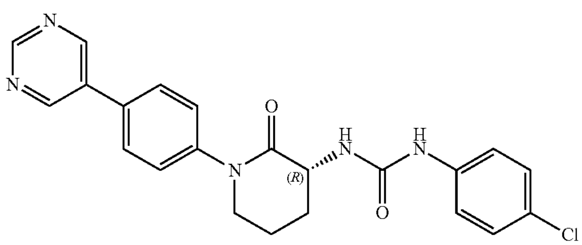 | 422.2 | Method D, RT = 1.369 min, 97.1% | ¹H NMR (400 MHz, DMSO-d₆): δ 9.20-9.12 (m, 3H), 8.92 (s, 1H), 7.87-7.80 (m, 2H), 7.51-7.38 (m, 4H), 7.30-7.21 (m, 2H), 5.56 (d, J = 6.6 Hz, 1H), 4.39-4.28 (m, 1H), 3.82-3.65 (m, 2H), 2.31-2.25 (m, 1H), 2.04-1.94 (m, 2H), 1.87-1.75 (m, 1H) |
| 90 | 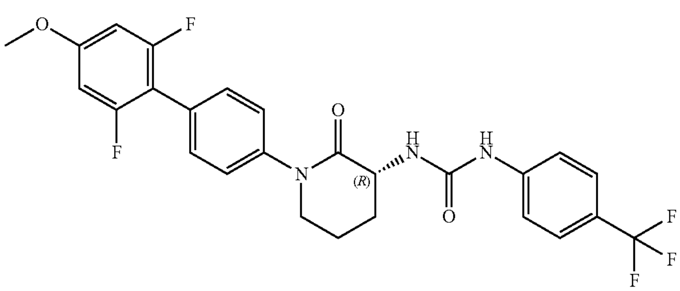 | 520.1 | Method E, RT = 2.413 min, 96.7% | ¹H NMR (400 MHz, DMSO-d₆): δ 9.24 (s, 1H), 7.64-7.54 (m, 4H), 7.46-7.37 (m, 4H), 6.92-6.82 (m, 2H), 6.71 (d, J = 6.8 Hz, 1H), 4.42-4.31 (m, 1H), 3.83 (s, 3H), 3.79-3.67 (m, 2H), 2.36-2.25 (m, 1H), 2.06-1.96 (m, 2H), 1.89-1.76 (m, 1H). |
| 91 | 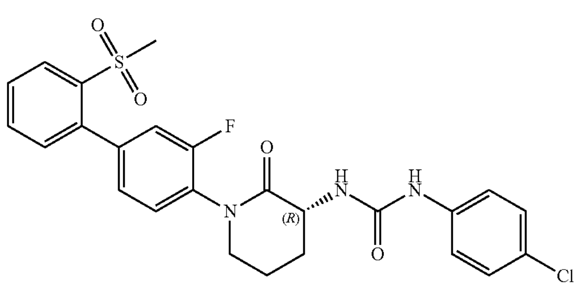 | 516.0 | Method F, RT = 1.939 min, 97.7% | ¹H NMR (400 MHz, DMSO-d₆): δ 8.91-8.86 (m, 1H) 8.14-8.08 (m, 1H) 7.82-7.67 (m, 2H) 7.51-7.34 (m, 5 H) 7.32-7.24 (m, 3H) 6.60-6.55 (m, 1H) 4.41-4.31 (m, 1H) 3.75-3.62 (m, 2H) 2.93 (s, 3H) 2.34-2.24 (m, 1H) 2.08-1.97 (m, 2H) 1.90-1.77 (m, 1H). |

TABLE 2-continued

| Ex | Structure | LCMS (M + H)+ | HPLC Method, RT (min.) & Purity | 1H NMR |
|---|---|---|---|---|
| 92 | 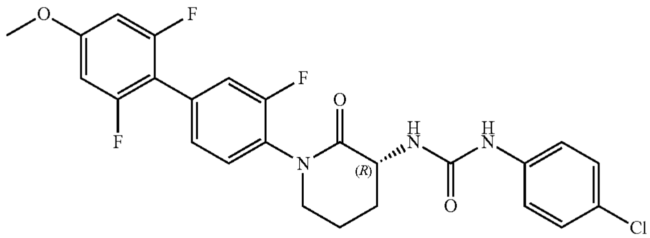 | 504.0 | Method E, RT = 2.374 min, 95.2% | ¹H NMR (400 MHz, DMSO-d₆): δ 8.94 (s, 1H), 7.46-7.38 (m, 5 H), 7.30-7.24 (m, 2H), 6.90-6.83 (m, 2H), 6.59-6.54 (m, 1H), 4.38-4.29 (m, 1H), 4.06 (s, 3H), 3.80-3.66 (m, 2H), 2.35-2.44 (m, 1H), 2.05-1.96 (m, 2H), 1.88-1.74 (m, 1H) |
| 93 | 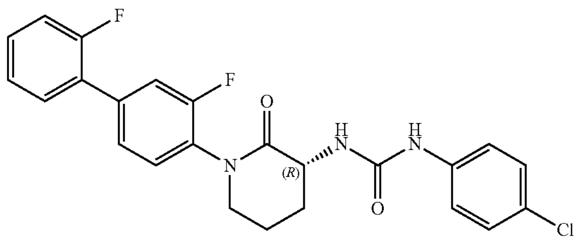 | 456.0 | Method E, RT = 2.277 min, 93.7% | ¹H NMR (400 MHz, DMSO-d₆): δ 8.94 (s, 1H), 7.50-7.48 (m, 1H), 7.46-7.38 (m, 6 H), 7.30-7.24 (m, 2H), 6.90-6.83 (m, 2H), 6.59-6.54 (m, 1H), 4.38-4.29 (m, 1H), 3.80-3.66 (m, 2H), 2.35-2.24 (m, 1H), 2.05-1.96 (m, 2H), 1.88-1.74 (m, 1H) |
| 94 | 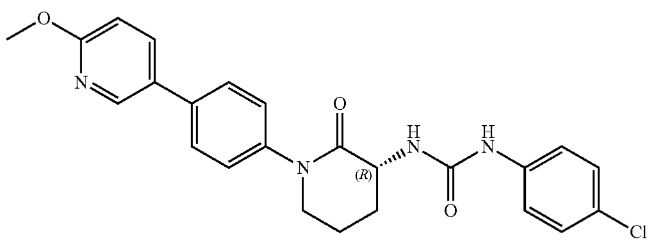 | 451.2 | Method D, RT = 1.817 min, 95.7% | ¹H NMR (400 MHz, DMSO-d₆): δ 8.96 (s, 1H), 8.50 (d, J = 2.5 Hz, 1H), 8.03 (dd, J = 8.5, 2.5 Hz, 1H), 7.72-7.65 (m, 2H), 7.47-7.35 (m, 4H), 7.31-7.22 (m, 2H), 6.94-6.88 (m, 1H), 6.60 (d, J = 7.0 Hz, 1H), 4.39-4.28 (m, 1H), 3.90 (s, 3H), 3.79-3.63 (m, 2H), 2.32-2.24 (m, 1H), 2.06-1.93 (m, 2H), 1.87-1.72 (m, 1H) |
| 95 | 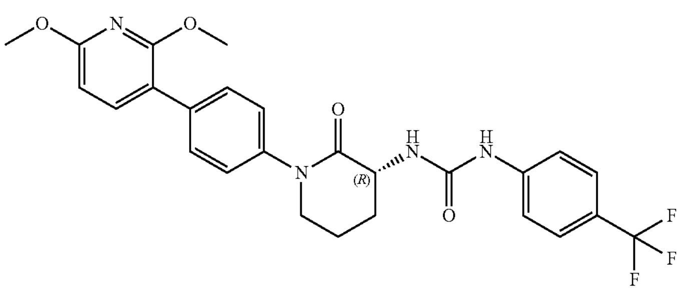 | 515.3 | Method E, RT = 2.185 min, 95.6% | ¹H NMR (400 MHz, METHANOL-d₄) δ 7.64 (d, J = 8.1 Hz, 1H), 7.60-7.50 (m, 6H), 7.32 (d, J = 8.6 Hz, 2H), 6.42 (d, J = 8.1 Hz, 1H), 4.44 (dd, J = 11.2, 6.1 Hz, 1H), 3.95 (d, J = 1.5 Hz, 6H), 3.88-3.69 (m, 2H), 2.41 (m, 1H), 2.18-2.09 (m, 2H), 2.05-1.92 (m, 1H) |
| 96 | 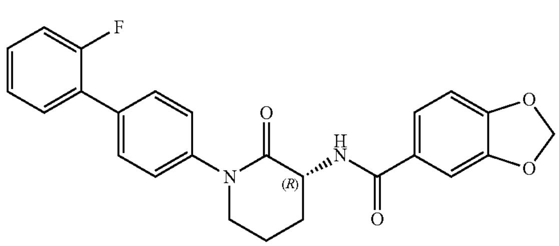 | 433.2 | Method F, RT = 1.784 min, 97.8% | ¹H NMR (400 MHz, DMSO-d₆): δ 8.58 (d, J = 8.1 Hz, 1H), 7.59-7.51 (m, 3H), 7.49-7.37 (m, 5H), 7.34-7.26 (m, 2H), 6.99 (d, J = 8.3 Hz, 1H), 6.09 (s, 2H), 4.63-4.53 (m, 1H), 3.84-3.63 (m, 2H), 2.15-1.97 (m, 4H) |

TABLE 2-continued

| Ex | Structure | LCMS (M + H)+ | HPLC Method, RT (min.) & Purity | 1H NMR |
|---|---|---|---|---|
| 97 | 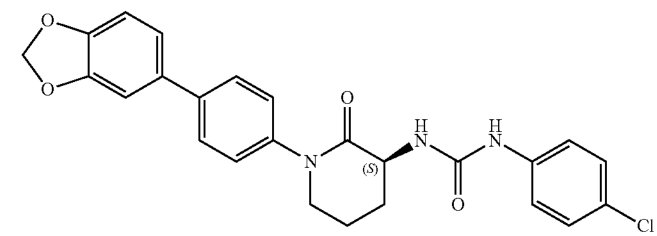 | 464.2 | Method D, RT = 1.938 min, 94.6% | ¹H NMR (400 MHz, DMSO-$d_6$): δ 8.91 (s, 1H), 7.65-7.58 (m, 2H), 7.47-7.39 (m, 2H), 7.38-7.32 (m, 2H), 7.30-7.24 (m, 3H), 7.18-7.13 (m, 1H), 7.00 (d, J = 8.0 Hz, 1H), 6.56 (d, J = 7.0 Hz, 1H), 6.06 (s, 2H), 4.39-4.27 (m, 1H), 3.80-3.64 (m, 2H), 2.29 (m, 1H), 2.05-1.94 (m, 2H), 1.86-1.74 (m, 1H) |
| 98 | 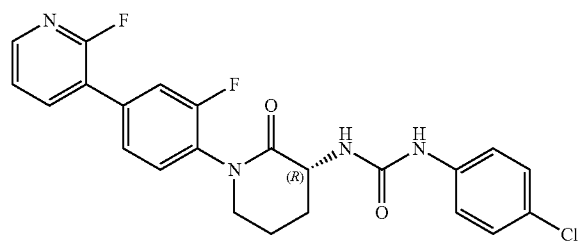 | 457.0 | Method F, RT = 1.981 min, 100% | ¹H NMR (400 MHz, DMSO-$d_6$): δ 8.90 (s, 1H), 8.29-8.25 (m, 1H), 8.23-8.14 (m, 1H), 7.63-7.47 (m, 4H), 7.45-7.39 (m, 2H), 7.31-7.22 (m, 2H), 6.61-6.56 (m, 1H), 4.41-4.30 (m, 1H), 3.73-3.61 (m, 2H), 2.35-2.24 (m, 1H), 2.08-1.97 (m, 2H), 1.88-1.77 (m, 1H) |
| 99 | 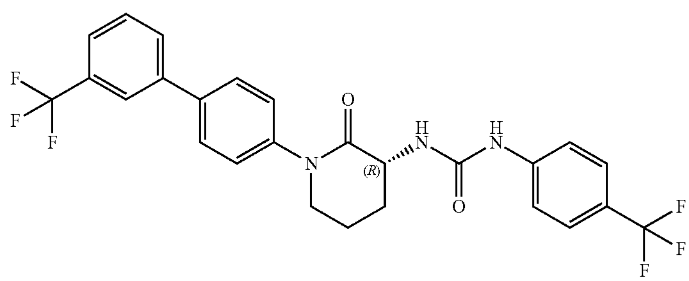 | 522.2 | Method E, RT = 2.29 min, 95.8% | ¹H NMR (400 MHz, DMSO-$d_6$): δ 9.48 (s, 1H), 8.30-8.22 (m, 2H), 8.05 (d, J = 8.8 Hz, 2H), 8.01-7.95 (m, 2H), 7.91-7.80 (m, 4H), 7.71 (d, J = 8.8 Hz, 2H), 6.95 (d, J = 6.6 Hz, 1H), 4.63 (d, J = 12.0 Hz, 1H), 4.12-3.90 (m, 2H), 2.57-2.52 (m, 1H), 2.34-2.22 (m, 2H), 2.11 (m, 1H) |
| 100 | 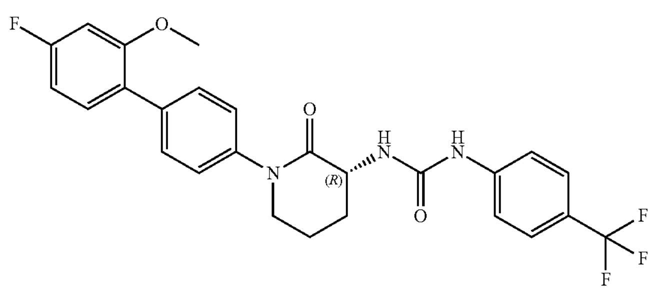 | 502.2 | Method F, RT = 2.15 min, 97.4% | ¹H NMR (400 MHz, DMSO-$d_6$): δ 9.48 (s, 1H), 7.90-7.79 (m, 4H), 7.75-7.67 (m, 2H), 7.62-7.55 (m, 3H), 7.28 (dd, J = 11.5, 2.4 Hz, 1H), 7.11 (td, J = 8.4, 2.4 Hz, 1H), 6.95 (d, J = 6.6 Hz, 1H), 4.61 (dd, J = 11.4, 6.2 Hz, 1H), 4.09-4.02 (m, 3H), 4.02-3.91 (m, 2H), 2.58-2.52 (m, 1H), 2.31-2.21 (m, 2H), 2.08 (m, 1H) |
| 101 | 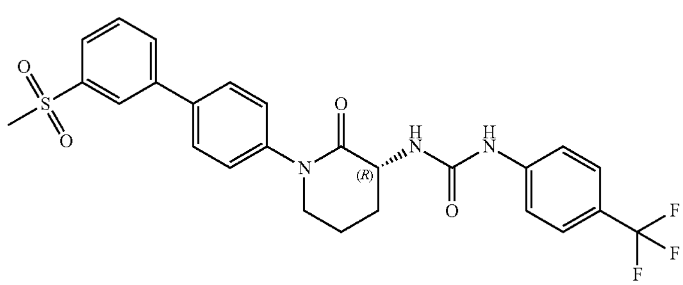 | 532.2 | Method F, RT = 1.79 min, 99.5% | ¹H NMR (400 MHz, DMSO-$d_6$): δ 9.48 (s, 1H), 8.43 (t, J = 1.7 Hz, 1H), 8.31 (dt, J = 8.0, 1.3 Hz, 1H), 8.17 (dt, J = 8.2, 1.2 Hz, 1H), 8.10-7.97 (m, 3H), 7.91-7.79 (m, 4H), 7.77-7.69 (m, 2H), 6.96 (d, J = 6.8 Hz, 1H), 4.69-4.57 (m, 1H), 4.11-3.90 (m, 2H), 3.56 (s, 3H), 2.63-2.52 (m, 1H), 2.33-2.21 (m, 2H), 2.16-2.03 (m, 1H) |

TABLE 2-continued

| Ex | Structure | LCMS (M + H)+ | HPLC Method, RT (min.) & Purity | 1H NMR |
|---|---|---|---|---|
| 102 | 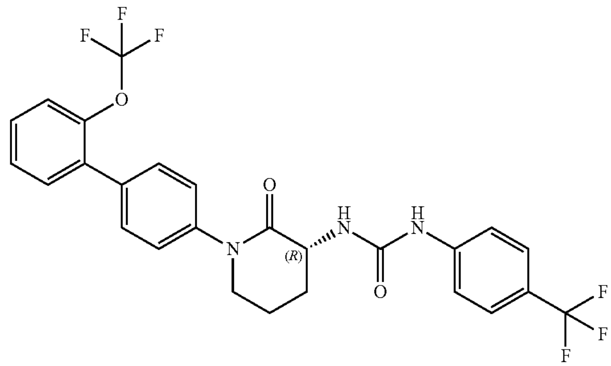 | 538.2 | Method F, RT = 2.29 min, 98.7% | ¹H NMR (400 MHz, DMSO-$d_6$): δ 9.47 (s, 1H), 7.89-7.80 (m, 5H), 7.79-7.72 (m, 5H), 7.71-7.67 (m, 2H), 6.94 (d, J = 7.1 Hz, 1H), 4.66-4.58 (m, 1H), 4.08-3.95 (m, 2H), 2.58-2.53 (m, 1H), 2.31-2.22 (m, 2H), 2.09 (m, 1H) |
| 103 | 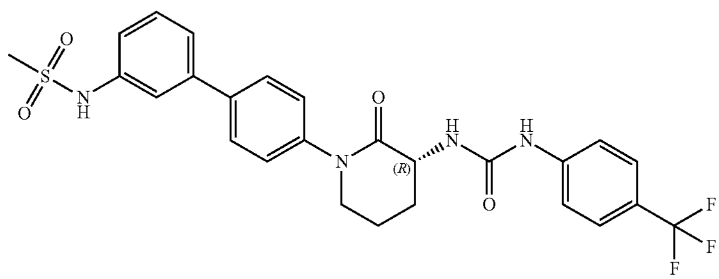 | 547.2 | Method E, RT = 1.8 min, 97.7% | ¹H NMR (400 MHz, DMSO-$d_6$): δ 10.08 (br. s., 1H), 9.47 (s, 1H), 7.94-7.80 (m, 6H), 7.76-7.61 (m, 5H), 7.47 (dt, J = 7.4, 1.9 Hz, 1H), 6.95 (d, J = 6.8 Hz, 1H), 4.69-4.54 (m, 1H), 4.08-3.89 (m, 2H), 3.31-3.25 (m, 3H), 2.58-2.51 (m, 1H), 2.33-2.22 (m, 2H), 2.15-2.01 (m, 1H) |
| 104 | 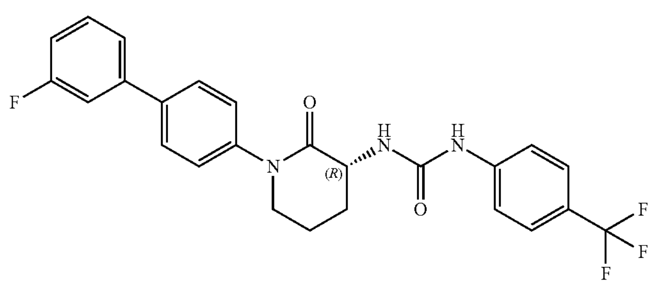 | 472.2 | Method F, RT = 2.14 min, 96.5% | ¹H NMR (400 MHz, DMSO-$d_6$): δ 9.47 (s, 1H), 8.03-7.96 (m, 2H), 7.95-7.71 (m, 7H), 7.70-7.63 (m, 2H), 7.51-7.38 (m, 1H), 6.95 (d, J = 6.8 Hz, 1H), 4.69-4.55 (m, 1H), 4.09-3.89 (m, 2H), 2.58-2.49 (m, 1H), 2.33-2.21 (m, 2H), 2.14-2.02 (m, 1H) |
| 105 | 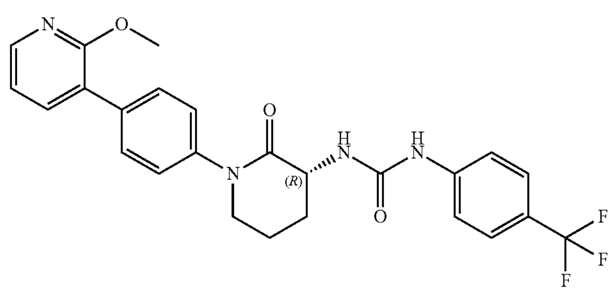 | 485.2 | Method E, RT = 1.94 min, 99.3% | ¹H NMR (400 MHz, DMSO-$d_6$): δ 9.48 (s, 1H), 8.44 (dd, J = 4.9, 2.0 Hz, 1H), 8.03 (dd, J = 7.3, 2.0 Hz, 1H), 7.91-7.80 (m, 6H), 7.67-7.58 (m, 2H), 7.36 (dd, J = 7.3, 4.9 Hz, 1H), 6.95 (d, J = 6.6 Hz, 1H), 4.67-4.55 (m, 1H), 4.15 (s, 3H), 4.07-3.91 (m, 2H), 2.59-2.52 (m, 1H), 2.32-2.21 (m, 2H), 2.17-2.02 (m, 1H) |
| 106 | 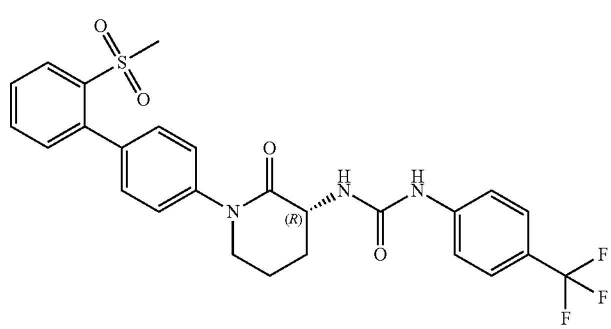 | 532.2 | Method F, RT = 1.8 min, 99.3% | ¹H NMR (400 MHz, DMSO-$d_6$): δ 9.47 (s, 1H), 8.40-8.33 (m, 1H), 8.02 (dd, J = 7.5, 1.3 Hz, 1H), 7.97-7.90 (m, 1H), 7.89-7.80 (m, 4H), 7.74-7.62 (m, 5H), 6.95 (d, J = 6.6 Hz, 1H), 4.63 (d, J = 11.7 Hz, 1H), 4.11-3.92 (m, 2H), 3.08 (s, 3H), 2.58 (m, 1H), 2.28 (m, 2H), 2.16-2.02 (m, 1H) |

TABLE 2-continued

| Ex | Structure | LCMS (M + H)+ | HPLC Method, RT (min.) & Purity | 1H NMR |
|---|---|---|---|---|
| 107 | 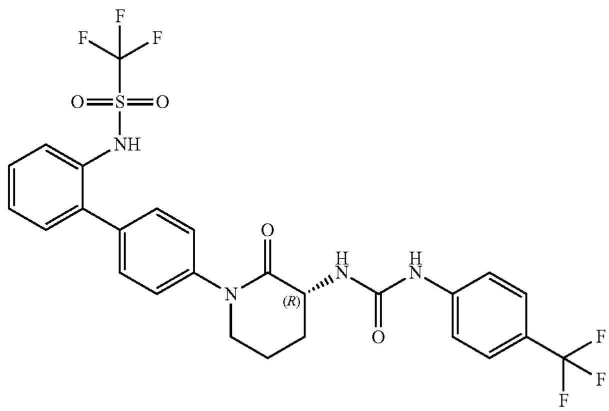 | 601.0 | Method F, RT = 2.215 min, 97.05%, | ¹H NMR (400 MHz, DMSO-d₆): δ 9.24-9.19 (m, 1H) 7.64-7.55 (m, 4 H) 7.49-7.33 (m, 8 H) 6.72-6.66 (m, 1H) 4.42-4.31 (m, 1H) 3.81-3.67 (m, 2H) 2.37-2.26 (m, 1H) 2.06-1.97 (m, 2H) 1.89-1.74 (m, 1H) |
| 108 | 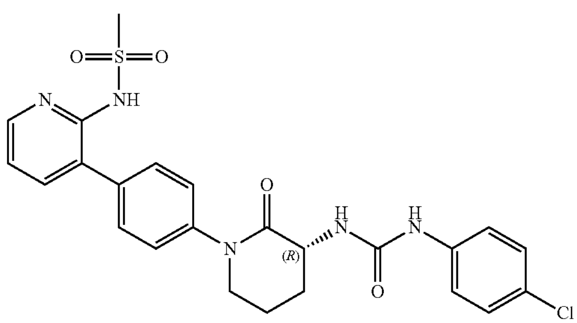 | 514.1 | Method F, RT = 2.022 min, 98.77%, | ¹H NMR (400 MHz, DMSO-d₆): δ 9.6 (bs, 1H) 8.97-8.87 (m, 2H) 7.47-7.39 (m, 4 H) 7.31-7.24 (m, 6 H) 6.61-6.54 (m, 1H) 4.39-4.29 (m, 1H) 4.06-4.03 (m, 2H) 3.0 (s, 3H) 2.35-2.26 (m, 1H) 2.03-1.96 (m, 2H) 1.86-1.75 (m, 1H) |
| 109 | 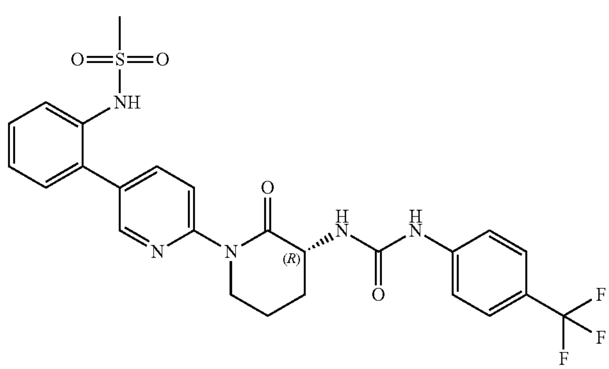 | 548.1 | Method E, RT = 2.25 min, 96.0% | ¹H NMR (400 MHz, DMSO-d₆): δ 9.28 (s, 1H), 9.15 (s, 1H), 8.5 (s, 1H), 7.88-7.87 (m, 2H), 7.63-7.57 (m, 4H), 7.47-7.39 (m, 4H), 6.73 (d, J = 8 Hz, 1H), 4.53-4.42 (m, 1H), 4.31-4.25 (m, 1H) 3.89--3.80 (m, 1H), 3.28 (s, 3H), 2.36-2.31 (m, 1H), 2.02-1.96 (m, 2H), 1.79-1.77 (m, 1H) |
| 110 | 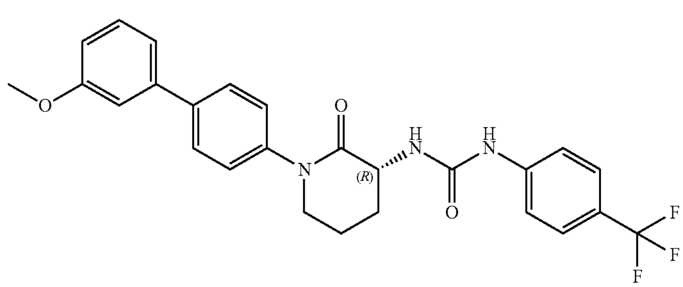 | 484.2 | Method E, RT = 2.11 min, 94.5% | ¹H NMR (400 MHz, DMSO-d₆): δ 9.23 (s, 1H), 7.74-7.66 (m, 2H), 7.65-7.54 (m, 4H), 7.44-7.34 (m, 4H), 7.28-7.16 (m, 1H), 6.94 (dt, J = 8.2, 1.3 Hz, 1H), 6.70 (d, J = 6.7 Hz, 1H), 4.43-4.29 (m, 1H), 3.83 (s, 3H), 3.81-3.66 (m, 2H), 2.33-2.26 (m, 1H), 2.07-1.95 (m, 2H), 1.90-1.76 (m, 1H) |

TABLE 2-continued

| Ex | Structure | LCMS (M + H)+ | HPLC Method, RT (min.) & Purity | 1H NMR |
|---|---|---|---|---|
| 111 | 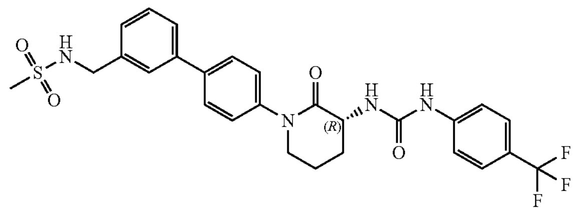 | 561.2 | Method E, RT = 1.812 min, 98.1% | ¹H NMR (400 MHz, DMSO-d₆): δ 9.23 (s, 1H), 7.73-7.64 (m, 3H), 7.63-7.53 (m, 6H), 7.49-7.40 (m, 3H), 7.35 (d, J = 7.5 Hz, 1H), 6.70 (d, J = 6.6 Hz, 1H), 4.41-4.32 (m, 1H), 4.24 (d, J = 6.4 Hz, 2H), 3.83-3.66 (m, 2H), 2.88 (s, 3H), 2.30 (m, 1H), 2.07-1.97 (m, 2H), 1.89-1.76 (m, 1H) |
| 112 | 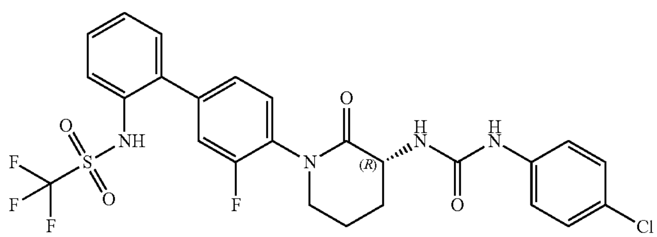 | 585.0 | Method F, RT = 1.891 min, 98.6%, | ¹H NMR (400 MHz, DMSO-d₆): δ 8.89 (s, 1H) 7.49-7.37 (m, 8 H) 7.33-7.24 (m, 4 H) 6.58 (s, 1H) 4.41-4.31 (m, 1H) 3.66 (d, J = 4.22 Hz, 2H) 2.37-2.28 (m, 1H) 2.08-1.98 (m, 2H) 1.88-1.74 (m, 1H) |
| 113 | 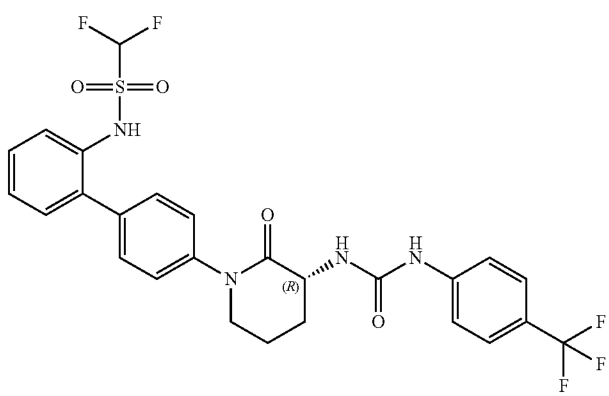 | 583.0 | Method F, RT = 2.022 min, 98.6%, | ¹H NMR (400 MHz, DMSO-d₆): δ 10.45 (s, 1H) 9.22 (s, 1H) 7.60 (d, J = 5.26 Hz, 4 H) 7.51-7.34 (m, 8 H) 6.88-6.56 (m, 2H) 4.45-4.31 (m, 1H) 3.74 (m, 2H) 2.37-2.26 (m, 1H) 2.02 (br. s., 2H) 1.89-1.74 (m, 1H) |
| 114 | 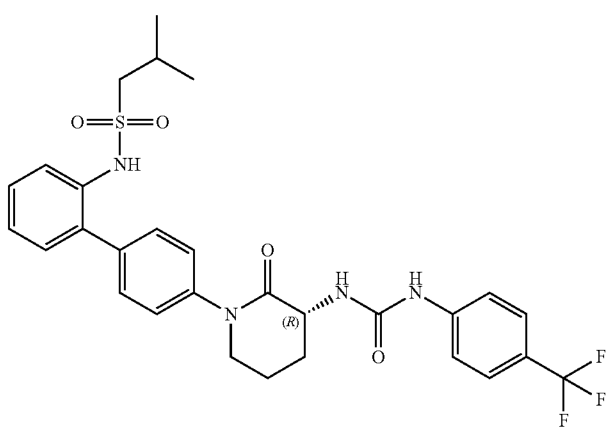 | 589.1 | Method F, RT = 2.365 min, 99.1%, | ¹H NMR (400 MHz, DMSO-d₆): δ 9.24-9.2 (m, 1H) 8.97-8.93 (m, 1H) 7.64-7.55 (m, 4 H) 7.51-7.46 (m, 2H) 7.42-7.31 (m, 6 H) 6.72-6.67 (m, 1H) 4.41-4.30 (m, 1H) 3.79-3.67 (m, 2H) 2.69-2.63 (m, 2H) 2.37-2.24 (m, 1H) 2.05-1.89 (m, 3H) 1.87-1.76 (m, 1H) 0.92-0.84 (m, 6H) |

TABLE 2-continued

| Ex | Structure | LCMS (M + H)+ | HPLC Method, RT (min.) & Purity | 1H NMR |
|---|---|---|---|---|
| 115 | 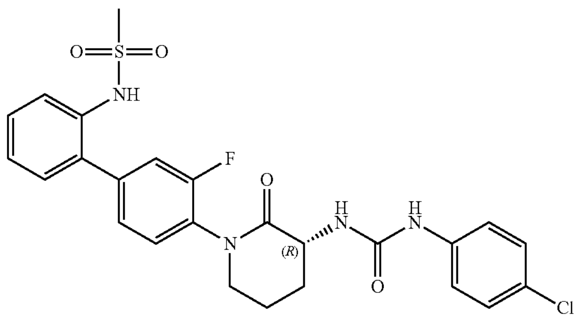 | 531.0 | Method D, RT = 1.993 min, 97.56%, | ¹H NMR (400 MHz, DMSO-d₆): δ 9.18-9.08 (m, 1H) 8.88 (s, 1H) 7.51-7.23 (m, 11H) 6.58 (d, J = 6.91 Hz, 1H) 4.41-4.34 (m, 1H) 3.83-3.72 (m, 2H) 2.79 (s, 3H) 2.36-2.27 (m, 1H) 2.08-1.99 (m, 2H) 1.92-1.75 (m, 1H). |
| 116 | 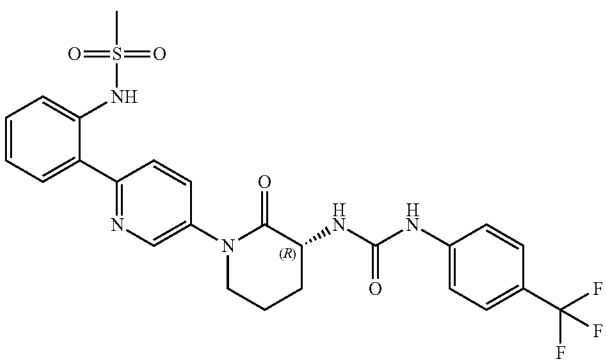 | 548.1 | Method E, RT = 1.91 min, 94.30% | ¹H NMR (400 MHz, DMSO-d₆): δ 9.26 (s, 1H), 8.50 (d, J = 2.2 Hz, 1H), 7.92-7.84 (m, 2H), 7.67-7.56 (m, 4H), 7.50-7.28 (m, 4H), 6.73 (d, J = 6.8 Hz, 1H), 4.55-4.47 (m, 1H), 4.29 (dt, J = 12.9, 6.4 Hz, 1H), 3.87-3.78 (m, 1H), 2.80 (s, 3H), 2.05-1.94 (m, 1H), 1.89-1.87 (m, 2H). 1.78-1.73 (m, 1H). |
| 117 | 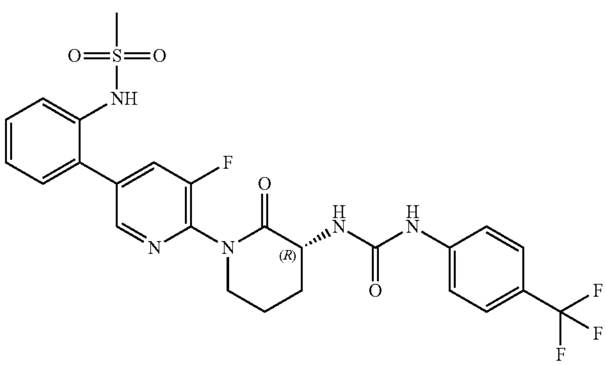 | 566.0 | Method F, RT = 1.94 min, 96.6% | ¹H NMR (400 MHz, DMSO-d₆): δ ppm 9.20 (s, 1H) 8.40 (d, J = 0.98 Hz, 1H) 7.91 (dd, J = 10.88, 1.83 Hz, 1H) 7.55-7.64 (m, 5 H) 7.42-7.51 (m, 3H) 7.31-7.38 (m, 1H) 6.71 (d, J = 7.09 Hz, 1H) 4.42-4.51 (m, 1H) 3.68-3.77 (m, 2H) 2.84 (s, 3H) 2.27-2.36 (m, 1H) 2.01-2.11 (m, 2H) 1.83-1.95 (m, 1H) |
| 118 | 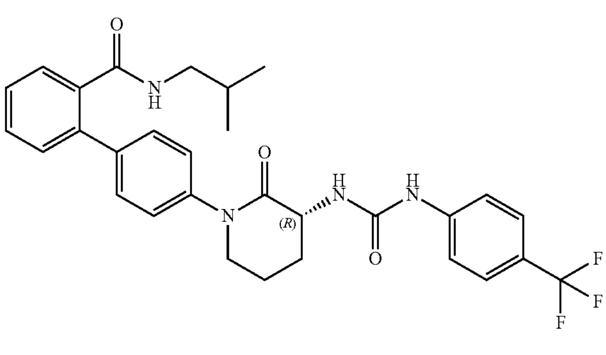 | 553.2 | Method F, RT = 1.934 min, 97.8% | ¹H NMR (400 MHz, DMSO-d₆): δ 9.22 (s, 1H), 8.15 (t, J = 5.8 Hz, 1H), 7.65-7.55 (m, 4H), 7.54-7.37 (m, 6H), 7.32 (d, J = 8.5 Hz, 2H), 6.69 (d, J = 6.5 Hz, 1H), 4.41-4.26 (m, 1H), 3.77-3.62 (m, 2H), 2.88 (t, J = 6.5 Hz, 2H), 2.32-2.25 (m, 1H), 1.99 (m, 2H), 1.87-1.74 (m, 1H), 1.68-1.55 (m, 1H), 0.71 (d, J = 6.5 Hz, 6H) |

TABLE 2-continued

| Ex | Structure | LCMS (M + H)+ | HPLC Method, RT (min.) & Purity | 1H NMR |
|---|---|---|---|---|
| 119 | 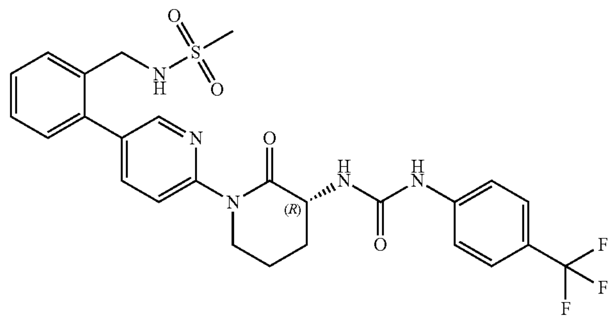 | 562.1 | Method E, RT = 1.94 min, 94.30% | ¹H NMR (400 MHz, DMSO-$d_6$): δ 9.25 (s, 1H), 8.44 (d, J = 2.0 Hz, 1H), 7.91-7.83 (m, 2H), 7.65-7.56 (m, 5H), 7.51-7.38 (m, 3H), 7.29 (d, J = 7.6 Hz, 1H), 6.73 (d, J = 7.1 Hz, 1H), 4.55-4.46 (m, 1H), 4.34-4.25 (m, 2H), 4.11 (d, J = 6.1 Hz, 2H), 2.67 (s, 3H), 2.33 (m, 1H), 2.10-1.90 (m, 2H), 1.81-1.72 (m, 1H). |
| 120 | 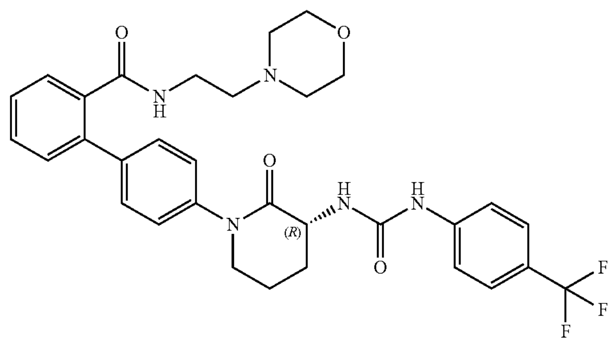 | 610.3 | Method F, RT = 1.649 min, 98.1% | ¹H NMR (400 MHz, DMSO-$d_6$): δ 9.23 (s, 1H), 7.95 (d, J = 6.0 Hz, 1H), 7.64-7.55 (m, 4H), 7.49 (d, J = 4.5 Hz, 1H), 7.44-7.38 (m, 5H), 7.36-7.29 (m, 2H), 6.69 (d, J = 7.0 Hz, 1H), 4.37 (s, 1H), 3.73 (d, J = 5.0 Hz, 2H), 3.55-3.47 (m, 4H), 3.19 (d, J = 5.5 Hz, 4H), 2.31-2.20 (m, 5H), 2.00 (m, 2H), 1.89-1.86 (m, 1H) |
| 121 | 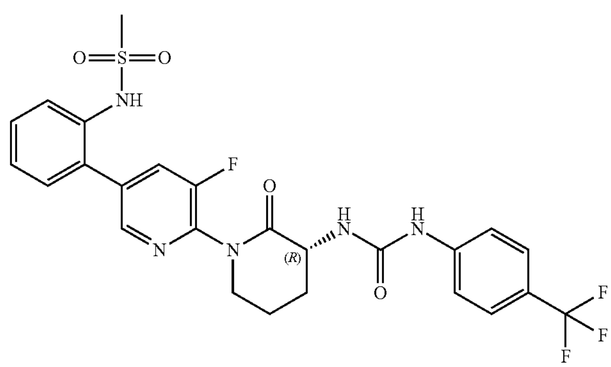 | 566.0 | Method F, RT = 1.95 min, 96.6% | ¹H NMR (400 MHz, DMSO-$d_6$): δ ppm 9.20 (s, 1H) 8.40 (d, J = 0.98 Hz, 1H) 7.91 (dd, J = 10.88, 1.83 Hz, 1H) 7.55-7.64 (m, 5 H) 7.42-7.51 (m, 3H) 7.31-7.38 (m, 1H) 6.71 (d, J = 7.09 Hz, 1H) 4.42-4.51 (m, 2H) 3.68-3.77 (m, 1H) 2.84 (s, 3H) 2.27-2.36 (m, 1H) 2.01-2.11 (m, 2H) 1.83-1.95 (m, 1H) |
| 122 | 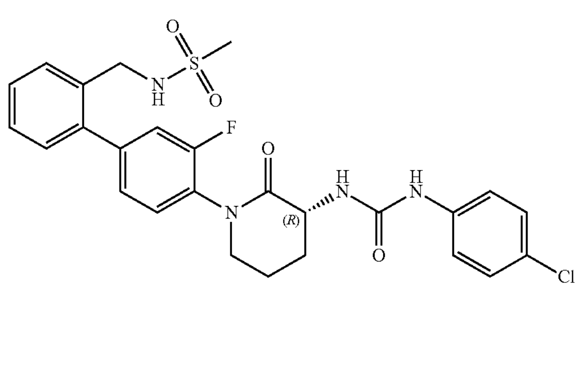 | 545 | Method F, RT = 2.096 min, 94.83%, | ¹H NMR (400 MHz, DMSO-$d_6$): δ 8.90-8.87 (m, 1H), 7.62-7.57 (m, 1H), 7.49-7.41 (m, 5H), 7.40-7.32 (m, 2H), 7.30-7.24 (m, 4H), 6.60-6.55 (m, 1H), 4.14-4.05 (m, 3H), 3.71-3.63 (m, 2H), 3.19-3.13 (m, 3H), 2.85-2.78 (m, 4H) |

TABLE 2-continued

| Ex | Structure | LCMS (M + H)+ | HPLC Method, RT (min.) & Purity | 1H NMR |
|---|---|---|---|---|
| 123 | 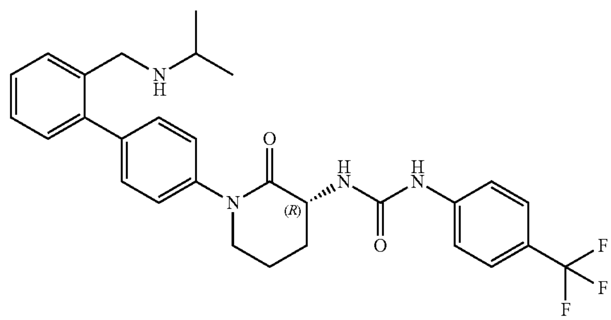 | 525.2 | Method E, RT = 1.697 min, 99.02% | ¹H NMR (400 MHz, DMSO-$d_6$): δ 9.24 (s, 1H), 8.67 (br. s., 1H), 7.71-7.66 (m, 1H), 7.64-7.56 (m, 4H), 7.54-7.48 (m, 2H), 7.47-7.36 (m, 5H), 6.73 (d, J = 6.8 Hz, 1H), 4.40-4.32 (m, 1H), 4.10 (br. s., 2H), 3.83-3.68 (m, 2H), 3.22-3.21 (m, 1H), 2.32-2.28 (m, 1H), 2.08-1.98 (m, 2H), 1.91-1.82 (m, 1H), 1.11 (d, J = 6.4 Hz, 6H). |
| 124 | 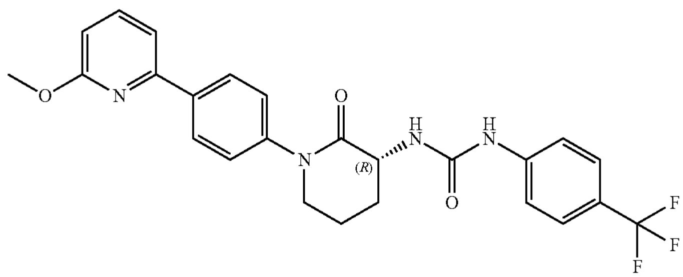 | 485.2 | Method E, RT = 2.073 min, 97.8% | ¹H NMR (400 MHz, DMSO-$d_6$): δ 9.23 (s, 1H), 8.12 (d, J = 8.6 Hz, 2H), 7.83-7.75 (m, 1H), 7.66-7.54 (m, 5H), 7.44 (d, J = 8.6 Hz, 2H), 6.79 (d, J = 8.1 Hz, 1H), 6.71 (d, J = 6.8 Hz, 1H), 4.43-4.33 (m, 1H), 3.97 (d, J = 6.1 Hz, 3H), 3.85-3.66 (m, 2H), 2.31 (m, 1H), 2.07-1.97 (m, 2H), 1.84 (m, 1H) |
| 125 | 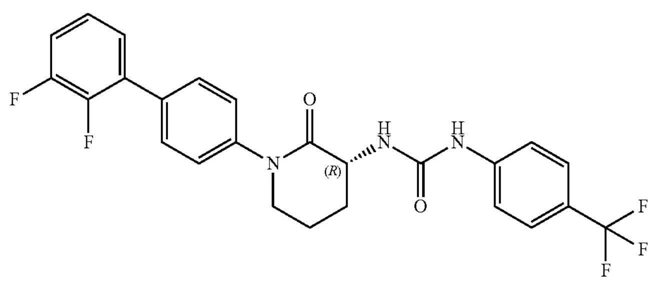 | 490.2 | Method F, RT = 2.167 min, 93.0% | ¹H NMR (400 MHz, DMSO-$d_6$): δ 9.23 (s, 1H), 7.67-7.55 (m, 6H), 7.46 (d, J = 8.6 Hz, 3H), 7.42-7.27 (m, 2H), 6.71 (s, 1H), 4.38 (d, J = 5.1 Hz, 1H), 3.85-3.68 (m, 2H), 2.33-2.26 (m, 1H), 2.02 (m, 2H), 1.84 (m, 1H) |
| 126 | 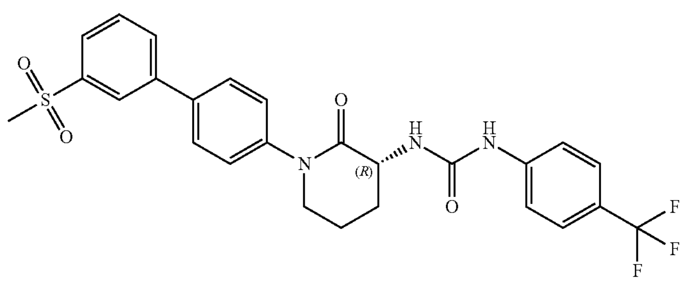 | 532.2 | Method F, RT = 1.8 min, 95.8% | ¹H NMR (400 MHz, DMSO-$d_6$): δ 9.22 (s, 1H), 8.17 (t, J = 1.8 Hz, 1H), 8.08-8.03 (m, 1H), 7.92 (dd, J = 9.5, 1.0 Hz, 1H), 7.84-7.72 (m, 3H), 7.65-7.55 (m, 4H), 7.50-7.43 (m, 2H), 6.70 (d, J = 6.5 Hz, 1H), 4.43-4.32 (m, 1H), 3.84-3.66 (m, 2H), 3.28 (s, 3H), 2.30 (m, 1H), 2.08-1.97 (m, 2H), 1.85 (m, 1H) |
| 127 | 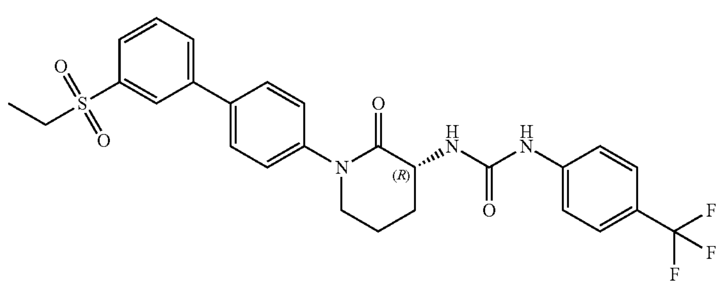 | 546.2 | Method F, RT = 1.89 min, 95.9 % | ¹H NMR (400 MHz, DMSO-$d_6$): δ 9.23 (s, 1H), 8.15-8.05 (m, 2H), 7.89 (br. s., 1H), 7.84-7.74 (m, 3H), 7.60 (d, J = 4.6 Hz, 4H), 7.49 (s, 2H), 6.72 (br. s., 1H), 4.40 (m, 1H), 3.84-3.66 (m, 2H), 3.44-3.37 (m, 2H), 2.33-2.27 (m, 1H), 2.03 (m, 2H), 1.86 (m, 1H), 1.14 (t, J = 7.2 Hz, 3H) |

TABLE 2-continued

| Ex | Structure | LCMS (M + H)+ | HPLC Method, RT (min.) & Purity | 1H NMR |
|---|---|---|---|---|
| 128 | 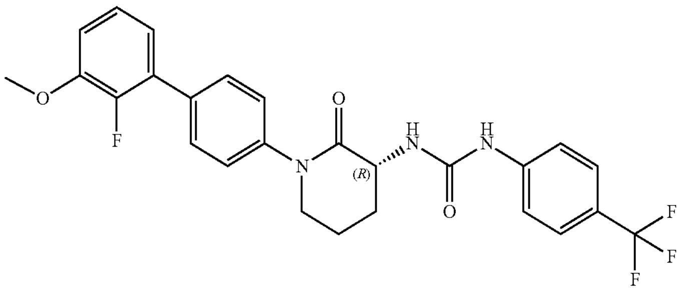 | 502.2 | Method F, RT = 2.103 min, 98.6% | ¹H NMR (400 MHz, DMSO-d₆): δ 9.22 (s, 1H), 7.65-7.52 (m, 6H), 7.45-7.37 (m, 2H), 7.26-7.13 (m, 2H), 7.06 (td, J = 7.2, 2.3 Hz, 1H), 6.69 (d, J = 6.5 Hz, 1H), 4.42-4.29 (m, 1H), 3.88 (s, 3H), 3.82-3.66 (m, 2H), 2.31 (d, J = 6.0 Hz, 1H), 2.07-1.96 (m, 2H), 1.89-1.76 (m, 1H) |
| 129 | 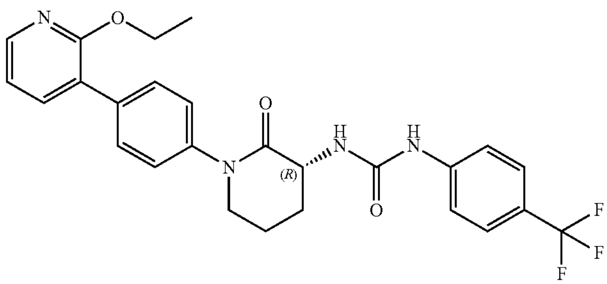 | 499.2 | Method E, RT = 2.073 min, 94.9% | ¹H NMR (400 MHz, DMSO-d₆): δ 9.23 (s, 1H), 8.16 (dd, J = 4.9, 2.0 Hz, 1H), 7.78 (dd, J = 7.2, 1.8 Hz, 1H), 7.65-7.54 (m, 6H), 7.38 (d, J = 8.3 Hz, 2H), 7.09 (dd, J = 7.3, 4.9 Hz, 1H), 6.70 (d, J = 6.8 Hz, 1H), 4.44-4.32 (m, 3H), 3.82-3.66 (m, 2H), 2.32-2.27 (m, 1H), 2.07-1.95 (m, 2H), 1.83 (m, 1H), 1.38-1.27 (m, 3H) |
| 130 | 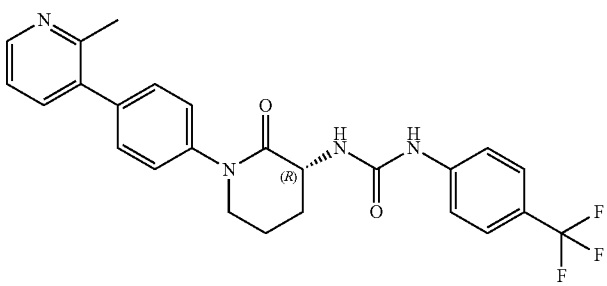 | 469.0 | Method F, RT = 1.96 min, 98.3% | ¹H NMR (400 MHz, DMSO-d₆): δ 9.24 (s, 1H), 8.68-8.61 (m, 1H), 8.07-7.95 (m, 1H), 7.66-7.55 (m, 5H), 7.49 (d, J = 3.4 Hz, 4H), 6.71 (d, J = 6.6 Hz, 1H), 4.43-4.32 (m, 1H), 3.85-3.69 (m, 2H), 2.57 (m, 3H), 2.33-2.27 (m, 1H), 2.03 (m, 2H), 1.92-1.78 (m, 1H) |
| 131 | 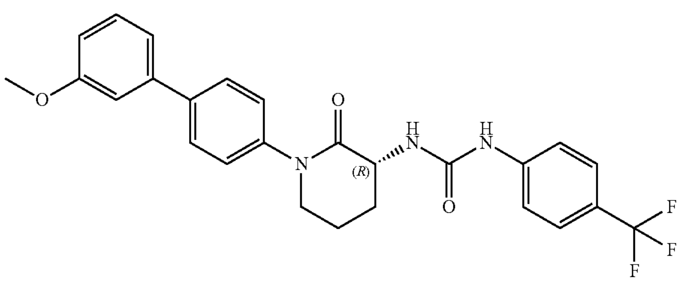 | 498.1 | Method F, RT = 2.48 min, 96.2% | ¹H NMR (400 MHz, DMSO-d₆): δ 9.23 (s, 1H), 7.70 (d, J = 8.3 Hz, 2H), 7.65-7.56 (m, 4H), 7.43-7.34 (m, 3H), 7.26-7.17 (m, 2H), 6.93 (d, J = 8.1 Hz, 1H), 6.70 (d, J = 6.8 Hz, 1H), 4.41-4.31 (m, 1H), 4.11 (m, 2H), 3.79 (s, 3H), 2.32-2.27 (m, 1H), 2.06-1.97 (m, 2H), 1.86-1.75 (m, 1H) |
| 132 | 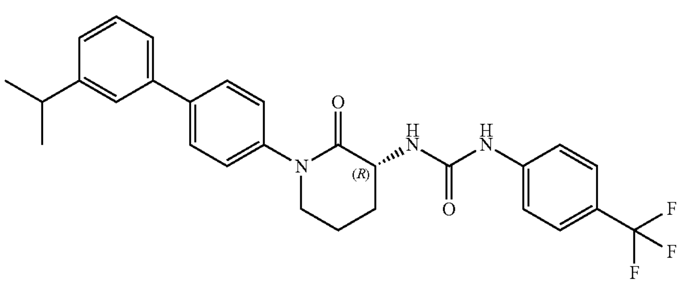 | 496.2 | Method E, RT = 2.715 min, 100% | ¹H NMR (400 MHz, DMSO-d₆): δ 9.23 (s, 1H), 7.68 (d, J = 8.6 Hz, 2H), 7.65-7.56 (m, 4H), 7.52 (s, 1H), 7.48 (d, J = 7.8 Hz, 1H), 7.43-7.35 (m, 3H), 7.26 (d, J = 7.8 Hz, 1H), 6.71 (d, J = 6.8 Hz, 1H), 4.41-4.32 (m, 1H), 3.84-3.65 (m, 2H), 2.98 (dt, J = 13.8, 7.0 Hz, 1H), 2.31 (m, 1H), 2.08-1.97 (m, 2H), 1.89-1.76 (m, 1H), 1.31-1.21 (m, 6H) |

TABLE 2-continued

| Ex | Structure | LCMS (M + H)+ | HPLC Method, RT (min.) & Purity | 1H NMR |
|---|---|---|---|---|
| 133 | 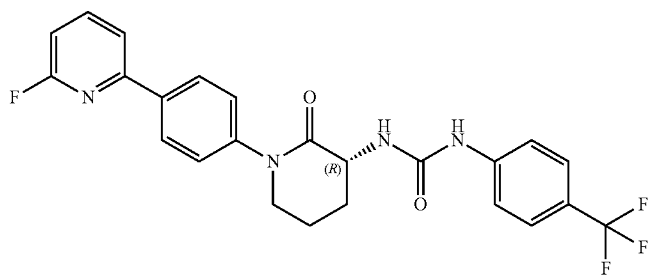 | 473.2 | Method F, RT = 1.95 min, 95.2% | ¹H NMR (400 MHz, DMSO-d₆): δ 9.24 (s, 1H), 8.10 (s, 3H), 7.97 (br. s., 1H), 7.65-7.56 (m, 4H), 7.47 (d, J = 9.0 Hz, 2H), 7.15 (br. s., 1H), 6.72 (br. s., 1H), 4.36 (m, 1H), 3.84-3.64 (m, 2H), 2.31-2.25 (m, 1H), 2.01 (m, 2H), 1.87-1.78 (m, 1H) |
| 134 | 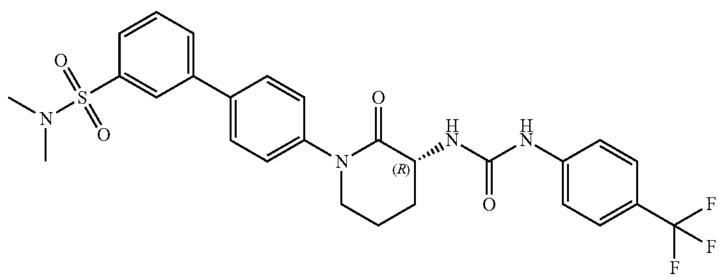 | 561.1 | Method E, RT = 2.21 min, 94.9% | ¹H NMR (400 MHz, DMSO-d₆): δ 9.23 (s, 1H), 8.09-8.01 (m, 1H), 7.93 (s, 1H), 7.83-7.73 (m, 4H), 7.65-7.55 (m, 4H), 7.47 (d, J = 8.6 Hz, 2H), 6.71 (d, J = 6.6 Hz, 1H), 4.42-4.31 (m, 1H), 3.85-3.67 (m, 2H), 2.71-2.64 (m, 6H), 2.32-2.26 (m, 1H), 2.02 (m, 2H), 1.85 (m, 1H) |
| 135 | 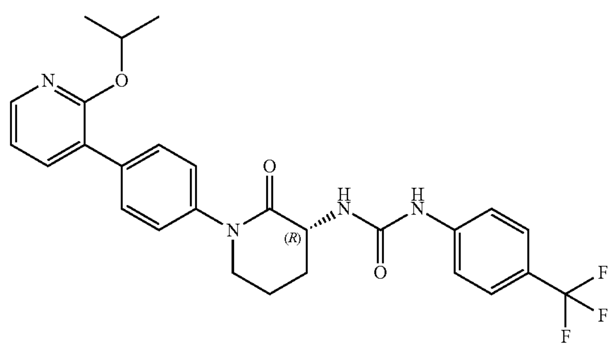 | 513.1 | Method F, RT = 2.47 min, 96.7% | ¹H NMR (400 MHz, DMSO-d₆): δ 9.22 (s, 1H), 8.15 (dd, J = 5.0, 2.0 Hz, 1H), 7.76 (dd, J = 7.3, 1.8 Hz, 1H), 7.65-7.55 (m, 6H), 7.40-7.34 (m, 2H), 7.09-7.02 (m, 1H), 6.69 (d, J = 6.5 Hz, 1H), 5.37 (quin, J = 6.3 Hz, 1H), 4.41-4.30 (m, 1H), 3.82-3.66 (m, 2H), 2.33-2.28 (m, 1H), 2.06-1.96 (m, 2H), 1.89-1.78 (m, 1H), 1.30 (d, J = 6.5 Hz, 6H) |
| 136 | 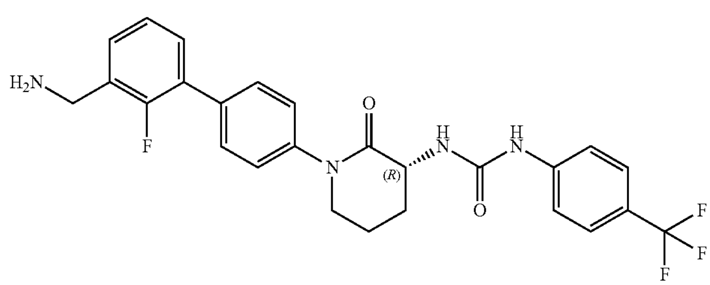 | 501.1 | Method F, RT = 1.67 min, 97.8% | ¹H NMR (400 MHz, DMSO-d₆): δ 9.25 (s, 1H), 7.67-7.47 (m, 7H), 7.46-7.38 (m, 3H), 7.32-7.24 (m, 1H), 6.73 (s, 1H), 4.42-4.30 (m, 1H), 3.87 (s, 2H), 3.76 (ddt, J = 18.7, 12.3, 6.3 Hz, 2H), 2.31 (m, 1H), 2.08-1.97 (m, 2H), 1.88-1.79 (m, 1H) |
| 137 | 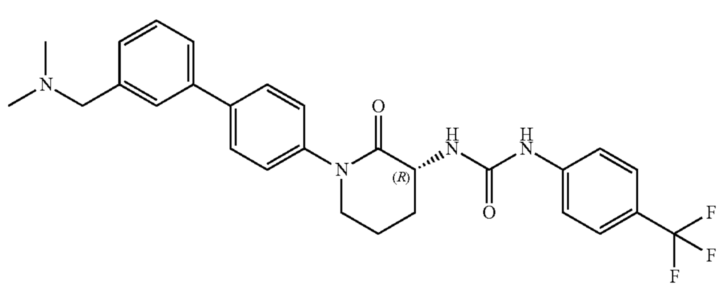 | 511.3 | Method F, RT = 1.7 min, 97.3% | ¹H NMR (400 MHz, DMSO-d₆): δ 9.22 (s, 1H), 7.69 (d, J = 8.5 Hz, 2H), 7.64-7.54 (m, 6H), 7.41 (d, J = 8.5 Hz, 3H), 7.31 (s, 1H), 6.69 (d, J = 7.0 Hz, 1H), 4.42-4.30 (m, 1H), 3.81-3.66 (s, 2H), 2.58-2.53 (s, 6H), 2.31-2.15 (m, 3H), 2.01 (m, 2H), 1.85 (m, 1H) |

Example 138: (R)—N-(3-(4-(2-oxo-3-(3-(4-(trifluoromethyl)phenyl)ureido)piperidin-1-yl)phenyl)pyridin-2-yl)methanesulfonamide

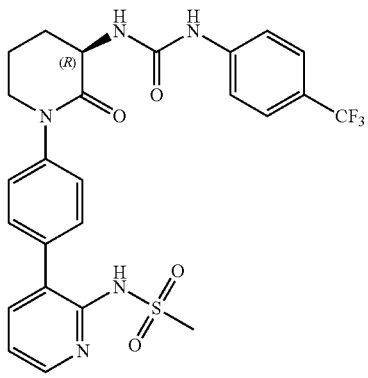

To a solution of Intermediate 4 (0.050 g, 0.099 mmol) in 1,4-dioxane (2 mL) were added N-(3-bromopyridin-2-yl)methanesulfonamide (0.025 g, 0.099 mmol) and potassium phosphate, tribasic (0.042 g, 0.20 mmol). The reaction mixture was purged with nitrogen for 5 min and charged with Pd(dppf)Cl$_2$.DCM adduct (8.1 mg, 9.9 μmol). The reaction mixture was again purged with nitrogen for 3 min and heated at 60° C. for 16 h. The reaction mixture was cooled, filtered through a celite pad and the filtrate was concentrated under reduced pressure. The crude product was purified by RP-HPLC to afford (19 mg, 0.035 mmol, 35% yield). MS(ESI) m/z: 548 (M+H); $^1$H NMR (400 MHz, DMSO-d6): δ 9.67 (s, 1H), 9.26-9.19 (s, 1H), 8.41-8.35 (m, 1H), 7.78-7.71 (m, 1H), 7.64-7.55 (m, 6H), 7.54-7.4 (m, 2H), 7.31-7.24 (m, 1H), 6.73-6.66 (m, 1H), 4.45-4.31 (m, 1H), 3.82-3.7 (m, 2H), 3.0-2.8 (m, 4H), 2.04-1.97 (m, 2H,) 1.90-1.81 (m, 1H). RT=1.859 min (Method F).

The following Examples in Table 3 were made by using analogous procedures as shown in Example 138 from Intermediates 4 or 5.

TABLE 3

| Ex | Structure | LC MS (M + H)+ | HPLC Method, RT (min.) & Purity | 1H NMR |
|---|---|---|---|---|
| 139 | 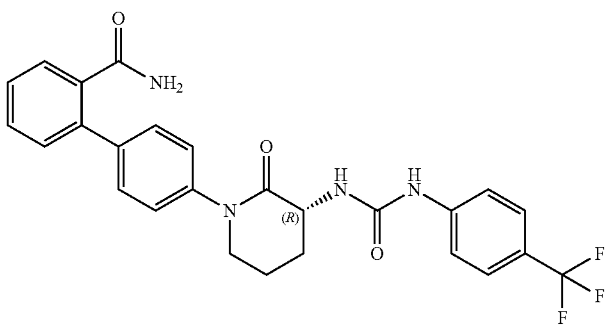 | 497.1 | Method E, RT = 1.810 min, 97.6% | $^1$H NMR (400 MHz, DMSO-d$_6$): δ 9.26-9.20 (m, 1H), 7.72-7.66 (m, 1H), 7.59 (d, J = 4.95 Hz, 4 H), 7.52-7.28 (m, 9 H), 6.73-6.66 (m, 1H), 4.40-4.30 (m, 1H), 3.79-3.66 (m, 2H), 2.37-2.28 (m, 1H), 2.04-1.96 (m, 2H), 1.88-1.75 (m, 1H). |
| 140 | 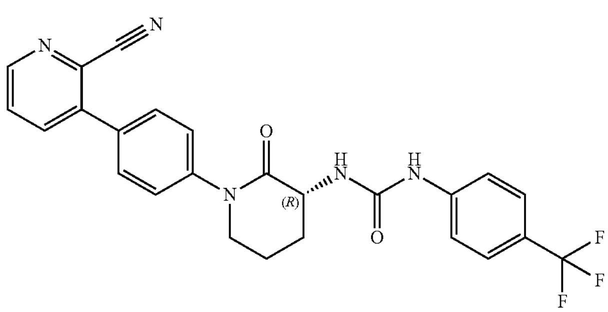 | 480.2 | Method F, RT = 1.765 min, 100% | $^1$H NMR (400 MHz, DMSO-d$_6$): δ 9.26-9.21 (m, 1H) 8.79-8.74 (m, 1H) 8.19-8.10 (m, 1H) 7.86-7.8 (m, 1H) 7.73-7.67 (m, 2H) 7.64-7.49 (m, 6 H) 6.73-6.68 (m, 1H) 4.44-4.33 (m, 1H) 3.86-3.69 (m, 2H) 2.35-2.26 (m, 1H) 2.06-1.97 (m, 2H) 1.91-1.77 (m, 1H) |
| 141 | 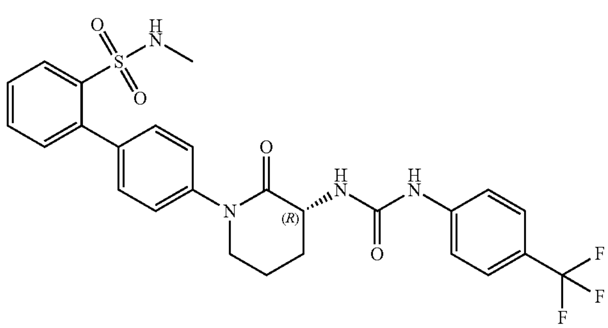 | 547.0 | Method F, RT = 2.106 min, 95.9%, | $^1$H NMR (400 MHz, DMSO-d$_6$): δ 9.24-9.19 (s, 1H) 7.67-7.54 (m, 7 H) 7.32-7.43 (m, 5 H) 7.0 (bs, 1H) 6.65-6.72 (m, 1H) 3.76-3.62 (m, 2H) 2.40-2.35 (m, 4 H) 2.06-1.98 (m, 2H) 1.83-1.81 (m, 1H) |

TABLE 3-continued

| Ex | Structure | LC MS (M + H)+ | HPLC Method, RT (min.) & Purity | 1H NMR |
|---|---|---|---|---|
| 142 | 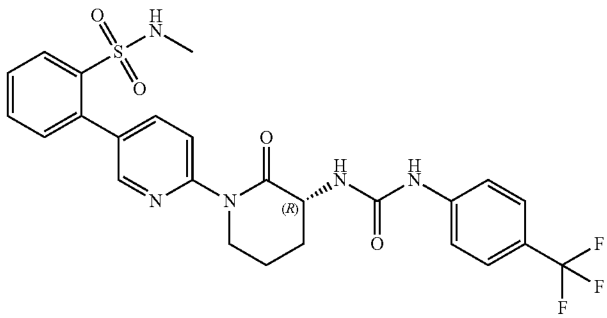 | 548.1 | Method E, RT = 1.98 min, 98.0% | ¹H NMR (400 MHz, DMSO-d₆): δ 9.26 (s, 1H), 8.40 (d, J = 2.0 Hz, 1H), 7.90-7.86 (m, 1H), 7.83-7.78 (m, 1H), 7.81-7.78 (m, 1H), 7.74-7.56 (m, 6H), 7.42 (d, J = 7.3 Hz, 1H), 7.34 (d, J = 4.6 Hz, 1H), 6.74 (d, J = 6.8 Hz, 1H), 4.56-4.48 (m, 1H), 4.37-4.29 (m, 1H), 3.88-3.80 (m, 1H), 2.40 (d, J = 5.1 Hz, 3H), 2.35-2.31 (m, 1H), 1.99-1.96 (m, 2H), 1.78-1.73 (m, 1H). |
| 143 | 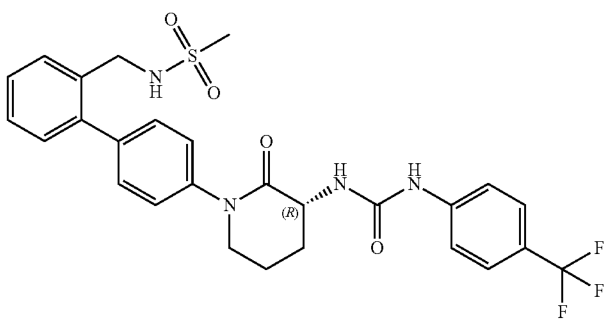 | 561.1 | Method F, RT = 2.059 min, 97.96%, | ¹H NMR (400 MHz, DMSO-d₆): δ 9.24-9.18 (m, 1H), 7.64-7.55 (m, 5H), 7.47-7.33 (m, 7H), 7.29-7.21 (m, 1H), 6.73-6.66 (m, 1H), 4.41-4.31 (m, 1H), 4.16-4.09 (m, 2H), 3.81-3.66 (m, 2H), 2.76 (s, 3H), 2.36-2.28 (m, 1H), 2.05-1.95 (m, 2H), 1.89-1.76 (m, 1H) |
| 144 | 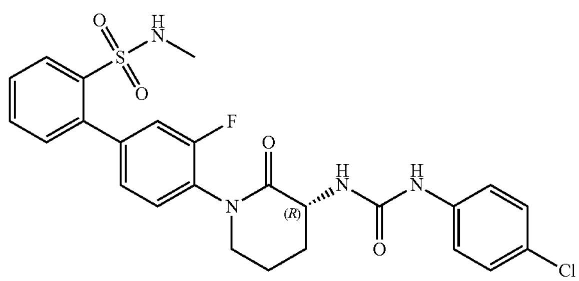 | 531.0 | Method F, RT = 1.99 min, 94.37%, | ¹H NMR (400 MHz, DMSO-d₆): δ 8.96-8.88 (m, 1H), 7.95-7.89 (m, 1H), 7.72-7.59 (m, 2H), 7.46-7.38 (m, 4H), 7.33-7.22 (m, 5H), 6.62-6.55 (m, 1H), 4.41-4.29 (m, 2H), 3.98-3.91 (m, 1H), 3.64 (s, 3H), 2.36-2.24 (m, 2H), 2.05-1.97 (m, 1H), 1.88-1.77 (m, 1H) |
| 145 | 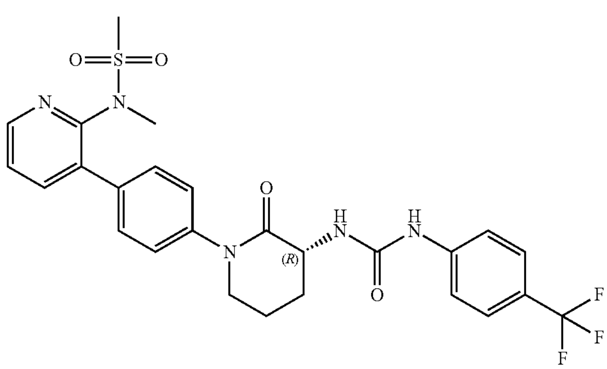 | 562.0 | Method F, RT = 2.041 min, 97.41%, | ¹H NMR (400 MHz, DMSO-d₆): δ 9.25-9.19 (m, 1H), 8.54-8.49 (m, 1H), 7.97-7.89 (m, 1H), 7.65-7.49 (m, 7H), 7.46-7.40 (m, 2H), 6.72-6.65 (m, 1H), 4.42-4.31 (m, 1H), 3.84-3.68 (m, 2H), 3.18 (s, 3H), 2.94 (s, 3H), 2.35-2.28 (m, 1H), 2.06-1.97 (m, 2H), 1.88-1.77 (m, 1H) |

Example 146: (R)-1-(4-chlorophenyl)-3-(1-(5-(2-fluorophenyl)pyridin-2-yl)-2-oxopiperidin-3-yl)urea

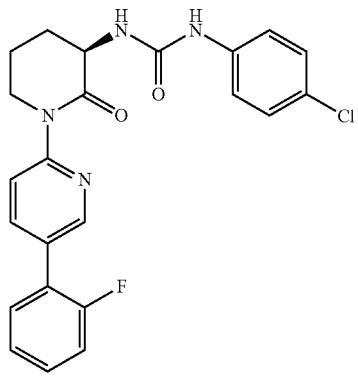 [SMILES: O=C(Nc1ccc(Cl)cc1)N[C@@H]1CCCN(c2ccc(-c3ccccc3F)cn2)C1=O]

Example 146a: tert-butyl (R)-(1-(5-(2-fluorophenyl)pyridin-2-yl)-2-oxopiperidin-3-yl)carbamate

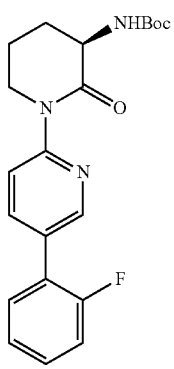 [SMILES: CC(C)(C)OC(=O)N[C@@H]1CCCN(c2ccc(-c3ccccc3F)cn2)C1=O]

To a solution of Intermediate 7 (150 mg, 0.41 mmol) in 1,4-dioxane (5 mL) were added potassium phosphate, tribasic (170 mg, 0.81 mmol) and (2-fluorophenyl)boronic acid (57 mg, 0.41 mmol). The reaction mixture was purged with nitrogen for 5 min and charged with Pd(dppf)Cl$_2$.DCM adduct (33 mg, 0.041 mmol). The reaction mixture was again purged with nitrogen for 3 min and heated at 60° C. for 15 h. The reaction mixture was cooled, filtered through celite pad, and washed with ethyl acetate (20 mL). The filtrate was concentrated under reduced pressure and the residue was purified by column chromatography afford Example 146a (120 mg, 0.31 mmol, 77% yield) as a brown solid. MS(ESI) m/z: 386 (M+H); $^1$H NMR (400 MHz, DMSO-d$_6$): δ 8.61 (s, 1H), 8.00 (d, J=8.0 Hz, 1H), 7.85 (d, J=8.5 Hz, 1H), 7.64-7.59 (m, 1H), 7.43-7.51 (m, 1H), 7.31-7.39 (m, 2H), 7.08 (d, J=8.5 Hz, 1H), 4.29-4.21 (m, 1H), 4.25-4.15 (m, 1H), 3.76-3.85 (m, 1H), 2.03-2.13 (m, 1H), 1.90-1.99 (m, 2H), 1.89-1.73 (m, 1H), 1.40 (s, 9H).

Example 146B: (R)-3-amino-1-(5-(2-fluorophenyl)pyridin-2-yl)piperidin-2-one hydrochloride

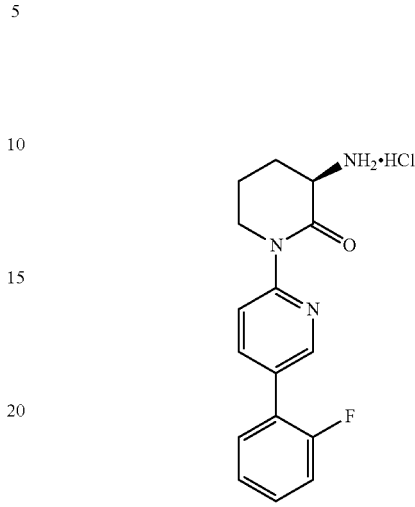

To a cooled solution of Example 146A (120 mg, 0.31 mmol) in 1,4-dioxane (10 mL) was added 4N HCl in 1,4-dioxane (1.6 mL) and stirred at RT for two hours. The solvent was evaporated and the mixture was triturated with diethyl ether (10 ml×2) to afford Example 146B (80 mg, 0.25 mmol, 80% yield) as a light brown solid. MS(ESI) m/z: 286.2 (M+H).

Example 146

To a cooled solution of Example 146B (40 mg, 0.12 mmol) in THF (5 mL) were added TEA (0.052 mL, 0.37 mmol) and 1-chloro-4-isocyanatobenzene (19 mg, 0.12 mmol) and reaction mixture was stirred at RT for 15 hours. The solvent was evaporated under reduced pressure and the crude compound was purified by RP-HPLC to Example 146 (10 mg, 18% yield). MS(ESI) m/z: 439 (M+H); $^1$H NMR (400 MHz, DMSO-d6): δ 8.94 (s, 1H), 8.62 (s, 1H), 8.03-7.99 (m, 1H), 7.89 (d, J=8.6 Hz, 1H), 7.62 (td, J=7.9, 1.6 Hz, 1H), 7.51-7.41 (m, 3H), 7.39-7.32 (m, 2H), 7.30-7.25 (m, 2H), 6.60 (d, J=7.3 Hz, 1H), 4.48 (dt, J=12.0, 6.9 Hz, 1H), 4.26 (dt, J=13.0, 6.5 Hz, 1H), 3.86-3.78 (m, 1H), 2.36-2.27 (m, 1H), 2.03-1.93 (m, 2H), 1.83-1.71 (m, 1H). RT=2.116 min (Method E).

The following Examples in Table 4 were made by using analogous procedures as shown in Example 146 starting from Intermediate 1a, tert-butyl (R)-(1-(4-bromophenyl)-2-oxopiperidin-3-yl)carbamate (obtained during the synthesis of Intermediate 1a), or Intermediates 7-10.

TABLE 4

| Ex | Structure | LC MS (M + H)+ | HPLC Method, RT (min.) & Purity | 1H NMR |
|---|---|---|---|---|
| 147 | 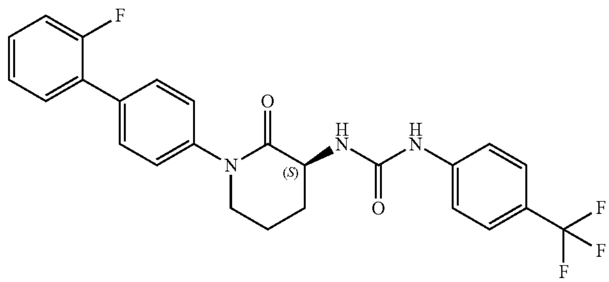 | 472.2 | Method F, RT = 2.121 min, 100.0% | ¹H NMR (400 MHz, DMSO-d₆): δ 9.22 (s, 1H), 7.53-7.64 (m, 7 H), 7.43 (d, J = 8.56 Hz, 3H), 7.27-7.37 (m, 2H), 6.70 (d, J = 6.85 Hz, 1H), 4.31-4.42 (m, 1H), 3.68-3.83 (m, 2H), 2.33 (m, 1H), 1.97-2.06 (m, 2H), 1.76-1.90 (m, 1H). |
| 148 | 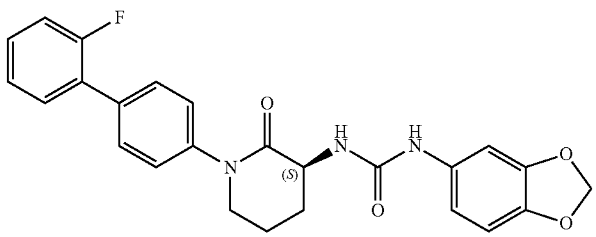 | 448.8 | Method E, RT = 1.76 min, 96.5% | ¹H NMR (400 MHz, DMSO-d₆): δ 8.68 (s, 1H), 7.61-7.52 (m,3H), 7.47-7.39 (m, 3H), 7.36-7.28 (m, 2H), 7.19 (d, J = 2.0 Hz, 1H), 6.83-6.75 (m, 1H), 6.69 (dd, J = 8.3, 2.2 Hz, 1H), 6.45 (d, J = 6.6 Hz, 1H), 5.97-5.93 (m, 2H), 4.38-4.29 (m, 1H), 3.82-3.66 (m, 2H), 2.33-2.25 (m, 1H), 2.01 (m, 2H), 1.80 (m, 1H) |
| 149 | 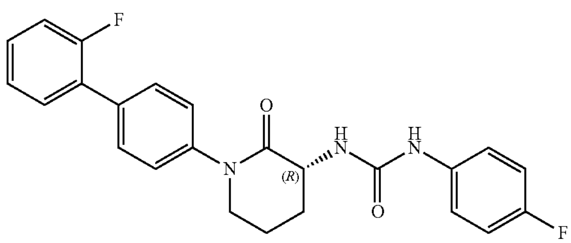 | 422.1 | Method F, RT = 2.080 min, 95.4% | ¹H NMR (400 MHz, DMSO-d₆): δ 8.81 (s, 1H), 7.59-7.53 (m, 3H), 7.45-7.37 (m, 5H), 7.34-7.29 (m, 2H), 7.08-7.04 (m, 2H), 6.51 (d, J = 6.80 Hz, 1H), 4.36-4.33 (m, 1H), 3.77-3.70 (m, 2H), 2.33-2.29 (m, 1H), 2,02-1.97 (m, 2H), 1.82-1.78 (m, 1H). |
| 150 | 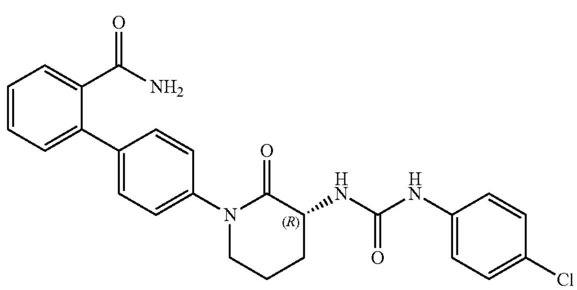 | 463.0 | Method F, RT = 1.654 min, 98.1% | ¹H NMR (400 MHz, DMSO-d₆): δ 8.94 (s, 1H), 7.73-7.69 (m, 1H), 7.51-7.41 (m, 8 H), 7.40-7.33 (m, 3H), 7.29-7.26 (m, 2H), 6.60-6.54 (m, 1H), 4.38-4.29 (m, 1H), 3.78-3.66 (m, 2H), 2.34-2.27 (m, 1H), 2.05-1.96 (m, 2H), 1.85-1.73 (m, 1H) |
| 151 | 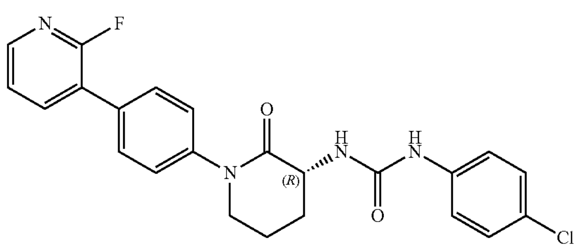 | 439.0 | Method F, RT = 1.900 min, 99.3% | ¹H NMR (400 MHz, DMSO-d₆): δ 8.94 (s, 1H), 8.25-8.24 (d, J = 4.89 Hz, 1H), 8.17-8.12 (ddd, J = 10.09, 7.76, 1.96 Hz, 1H), 7.66-7.63 (dd, J = 8.56, 1.47 Hz, 2H), 7.51-7.41 (m, 5 H), 7.30-7.25 (m, 2H), 6.58-6.57 (d, J = 6.60 Hz, 1H), 4.39-4.31 (m, 1H), 3.82-3.68 (m, 2H), 2.34-2.28 (m, 1H), 2.04-1.97 (m, 2H), 1.87-1.80 (m, 1H). |

TABLE 4-continued

| Ex | Structure | LC MS (M + H)+ | HPLC Method, RT (min.) & Purity | 1H NMR |
|---|---|---|---|---|
| 152 | 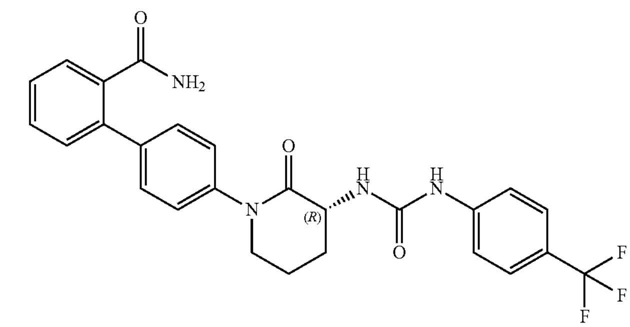 | 497.1 | Method F, RT = 1.813 min, 99.1% | ¹H NMR (400 MHz, DMSO-d₆): δ 9.24 (s, 1H), 7.73-7.69 (m, 1H), 7.62-7.60 (dd, J = 4.40 Hz, 4 H), 7.52-7.30 (m, 9 H), 6.72-6.67 (m, 1H), 4.40-4.30 (m, 1H), 3.77-3.69 (m, 2H), 2.36-2.28 (m, 1H), 2.04-1.96 (m, 2H), 1.89-1.74 (m, 1H) |
| 154 | 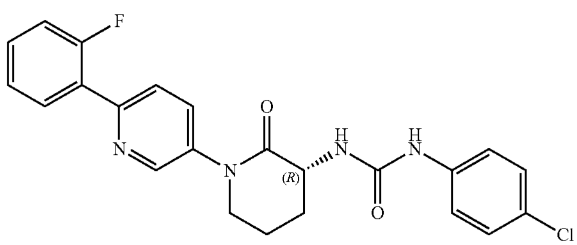 | 439.0 | Method F, RT = 2.103 min, 98.9% | ¹H NMR (400 MHz, DMSO-d₆): δ 8.97 (s, 1H), 8.63 (s, 1H), 8.05-7.99 (m, 1H), 7.90 (d, J = 8.80 Hz, 1H), 7.66-7.59 (m, 1H), 7.52-7.42 (m, 3H), 7.40-7.32 (m, 2H), 7.30-7.25 (m, 2H), 6.61 (d, J = 7.09 Hz, 1H), 4.53-4.45 (m, 1H), 4.27 (dt, J = 12.72, 6.36 Hz, 1H), 3.87-3.78 (m, 1H), 2.35-2.28 (m, 1H), 2.03-1.94 (m, 2H), 1.83-1.73 (m, 1H) |
| 155 | 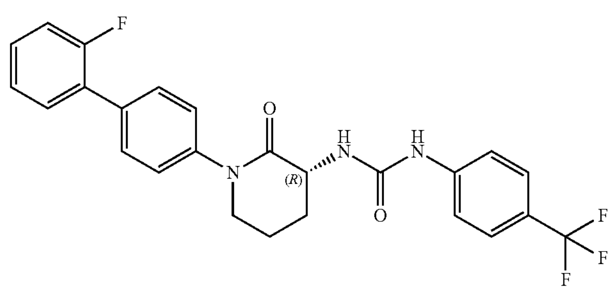 | 472.0 | Method F, RT = 2.464 min, 100% | ¹H NMR (400 MHz, DMSO-d₆): δ 8.73 (s, 1H), 7.87 (d, J = 8.40 Hz, 2H), 7.66 (d, J = 8.00 Hz, 2H), 7.45 (t, J = 8.00 Hz, 1H), 7.32-7.28 (m, 3H), 7.26-7.20 (m, 2H), 6.67 (d, J = 8.40 Hz, 2H), 5.90 (t, J = 5.60 Hz, 1H), 4.33-4.30 (m, 1H), 3.15-3.10 (m, 2H), 1.98-1.93 (m, 1H), 1.82-1.70 (m, 3H). |
| 156 | 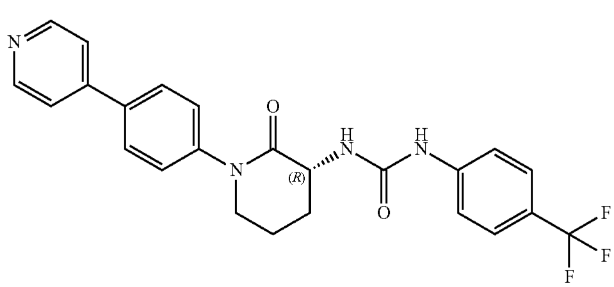 | 455.2 | Method F, RT = 1.665 min, 95.3% | ¹H NMR (400 MHz, DMSO-d₆): δ 9.22 (s, 1H), 8.68 (m, 2H), 7.92-7.77 (m, 4H), 7.67-7.56 (m, 4H), 7.49 (d, J = 8.6 Hz, 2H), 6.71 (s, 1H), 4.44-4.31 (m, 1H), 3.85-3.66 (m, 2H), 2.31 (m, 1H), 2.10-1.95 (m, 2H), 1.92-1.75 (m, 1H). |
| 157 | 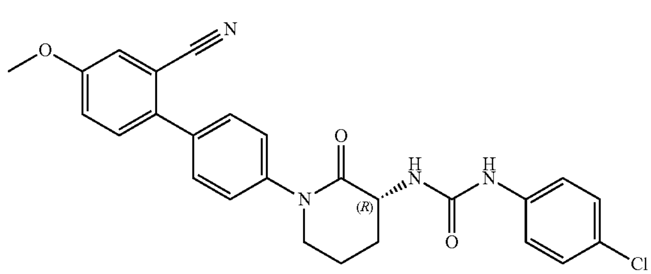 | 475.1 | Method F, RT = 2.126 min, 99.7% | ¹H NMR (400 MHz, DMSO-d₆): δ 8.93 (s, 1H), 7.60-7.50 (m, 4H), 7.48-7.40 (m, 4H), 7.36 (dd, J = 8.8, 2.7 Hz, 1H), 7.30-7.22 (m, 2H), 6.57 (d, J = 6.8 Hz, 1H), 4.40-4.27 (m, 1H), 3.86 (s, 3H), 3.82?-3.67 (m, 2H), 2.35-2.24 (m, 1H), 2.05-1.95 (m, 2H), 1.82-1.80 (m, 1H) |

TABLE 4-continued

| Ex | Structure | LC MS (M + H)+ | HPLC Method, RT (min.) & Purity | 1H NMR |
|---|---|---|---|---|
| 158 | 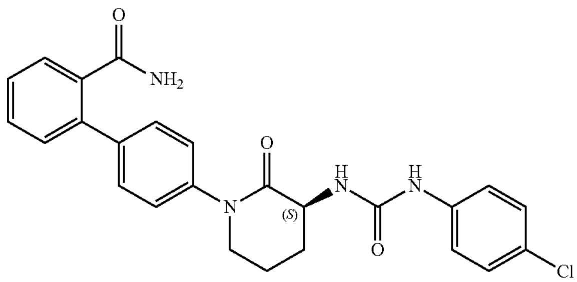 | 463.0 | Method F, RT = 1.668 min, 97.7% | ¹H NMR (400 MHz, DMSO-d₆): δ 8.93 (s, 1H), 7.69 (s, 1H), 7.53-7.23 (m, 13H), 6.56 (d, J = 6.6 Hz, 1H), 4.38-4.28 (m, 1H), 3.72 (tq, J = 12.5, 6.3 Hz, 2H), 2.30 (m, 1H), 2.02-1.94 (m, 2H), 1.86-1.73 (m, 1H). |
| 159 | 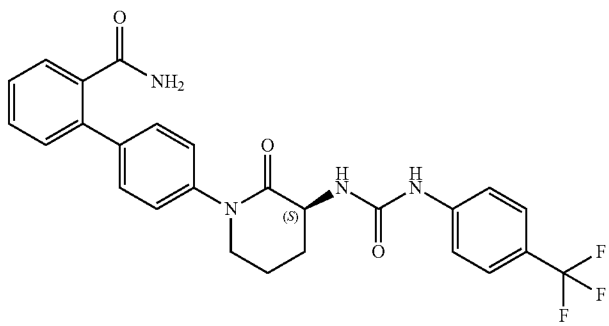 | 497.2 | Method F, RT = 1.590 min, 99.0% | ¹H NMR (400 MHz, DMSO-d₆): δ 9.22 (s, 1H), 7.69 (s, 1H), 7.64-7.55 (m, 4H), 7.52-7.27 (m, 9H), 6.69 (d, J = 6.6 Hz, 1H), 4.41-4.29 (m, 1H), 3.73 (tq, J = 12.7, 6.2 Hz, 2H), 2.37-2.26 (m, 1H), 2.04-1.93 (m, 2H), 1.88-1.74 (m, 1H). |
| 160 | 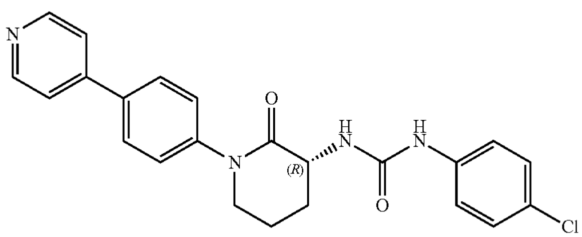 | 421.2 | Method F, RT = 1.506 min, 96.8% | ¹H NMR (400 MHz, DMSO-d₆): δ 8.93 (s, 1H), 8.69-8.60 (m, 2H), 7.89-7.80 (m, 2H), 7.77-7.70 (m, 2H), 7.51-7.39 (m, 4H), 7.31-7.22 (m, 2H), 6.57 (d, J = 6.8 Hz, 1H), 4.41-4.29 (m, 1H), 3.83-3.63 (m, 2H), 2.37-2.22 (m, 1H), 2.06-1.94 (m, 2H), 1.89-1.73 (m, 1H). |
| 161 | 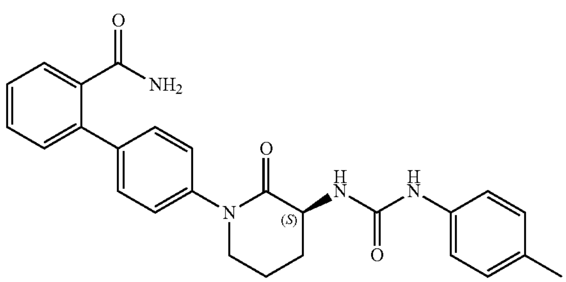 | 443.2 | Method F, RT = 1.346 min, 99.8% | ¹H NMR (400 MHz, DMSO-d₆): δ 8.65 (s, 1H), 7.69 (s, 1H), 7.52-7.23 (m, 11H), 7.03 (d, J = 8.1 Hz, 2H), 6.46 (d, J = 6.4 Hz, 1H), 4.38-4.27 (m, 1H), 3.78-3.66 (m, 2H), 2.37-2.25 (m, 1H), 2.22 (s, 3H), 1.98 (m, 2H), 1.78 (m, 1H). |
| 162 | 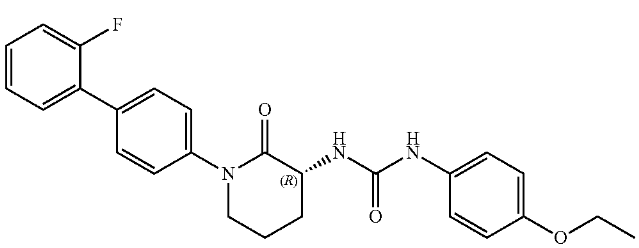 | 448.3 | Method F, RT = 1.9 min, 96.9% | ¹H NMR (400 MHz, DMSO-d₆): δ 8.55 (s, 1H), 7.60-7.51 (m, 2H), 7.45-7.38 (m, 2H), 7.36-7.25 (m, 3H), 7.00 (br. s., 1H), 6.83-6.76 (m, 2H), 6.50 (s, 1H), 6.40 (d, J = 6.5 Hz, 1H), 6.26 (s, 1H), 4.39-4.28 (m, 1H), 3.95 (q, J = 7.0 Hz, 2H), 3.81-3.66 (m, 2H), 2.31-2.23 (m, 1H), 2.05-1.94 (m, 2H), 1.86-1.72 (m, 1H), 1.29 (t, J = 7.0 Hz, 3H) |

TABLE 4-continued

| Ex | Structure | LC MS (M + H)+ | HPLC Method, RT (min.) & Purity | 1H NMR |
|---|---|---|---|---|
| 163 | 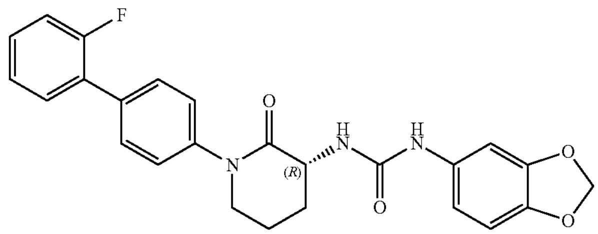 | 448.2 | Method F, RT = 1.768 min, 93.22% | ¹H NMR (400 MHz, DMSO-d₆): δ 8.66 (s, 1H), 7.60-7.50 (m, 3H), 7.48-7.38 (m, 2H), 7.36-7.27 (m, 2H), 7.18 (d, J = 2.5 Hz, 1H), 6.81-6.75 (m, 1H), 6.68 (dd, J = 8.5, 2.0 Hz, 1H), 6.50 (s, 1H), 6.43 (d, J = 6.5 Hz, 1H), 5.93 (s, 2H), 4.38-4.28 (m, 1H), 3.82-3.64 (m, 2H), 2.30 (m, 1H), 1.99 (m, 2H), 1.80 (m, 1H) |
| 164 | 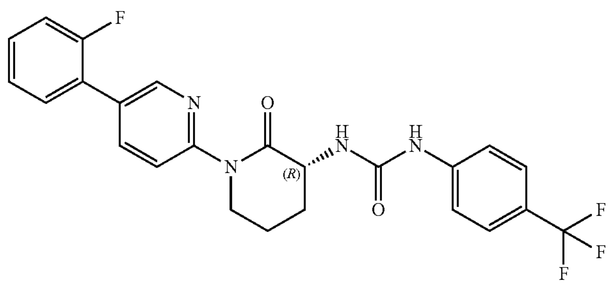 | 473.1 | Method E, RT = 2.292 min, 93.7% | ¹H NMR (400 MHz, DMSO-d₆): δ 9.23 (s, 1H), 8.62 (s, 1H), 8.06-7.98 (m, 1H), 7.90 (d, J = 8.8 Hz, 1H), 7.67-7.55 (m, 5H), 7.52-7.43 (m, 1H), 7.39-7.30 (m, 2H), 6.72 (d, J = 7.1 Hz, 1H), 4.55-4.45 (m, 1H), 4.33-4.22 (m, 1H), 3.89-3.79 (m, 1H), 2.39-2.29 (m, 1H), 2.05-1.94 (m, 2H), 1.85-1.72 (m, 1H) |
| 165 | 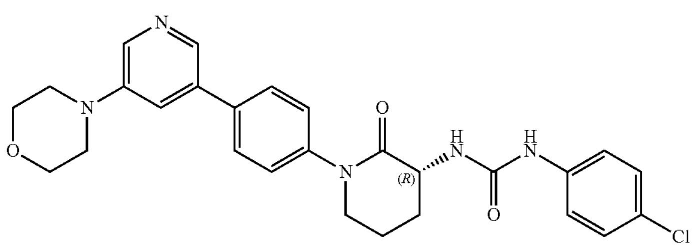 | 506.3 | Method F, RT = 1.783 min, 98.3% | ¹H NMR (400 MHz, DMSO-d₆): δ 8.93 (s, 1H), 8.30 (s, 1H), 7.74 (d, J = 8.6 Hz, 2H), 7.53 (s, 1H), 7.46-7.36 (m, 5H), 7.30-7.21 (m, 2H), 6.57 (d, J = 6.8 Hz, 1H), 4.38-4.28 (m, 1H), 3.79-3.62 (m, 6H), 3.29-3.23 (m, 4H), 2.33-2.23 (m, 1H), 2.05-1.93 (m, 2H), 1.82 (m, 1H) |
| 166 | 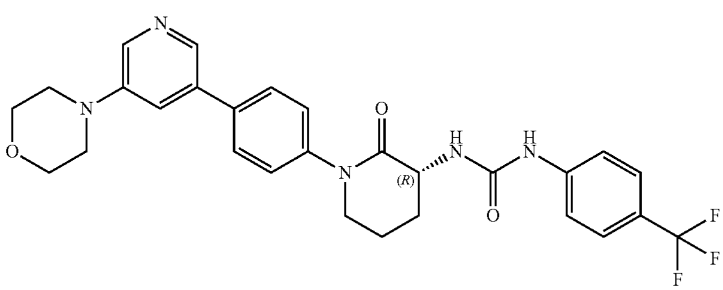 | 540.1 | Method F, RT = 1.929 min, 100% | ¹H NMR (400 MHz, DMSO-d₆): δ 9.23 (s, 1H), 8.32 (dd, J = 11.0, 2.2 Hz, 2H), 7.79-7.72 (m, 2H), 7.64-7.51 (m, 5H), 7.42 (d, J = 8.6 Hz, 2H), 6.71 (d, J = 6.6 Hz, 1H), 4.40-4.31 (m, 1H), 3.81-3.66 (m, 6H), 3.30-3.23 (m, 4H), 2.31 (dd, J = 11.9, 6.7 Hz, 1H), 2.05-1.96 (m, 2H), 1.90-1.76 (m, 1H) |
| 167 | 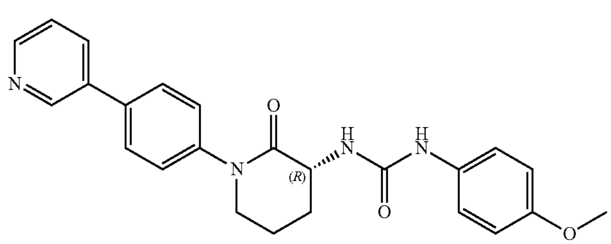 | 417.1 | Method F, RT = 1.485 min, 100% | ¹H NMR (400 MHz, DMSO-d₆): δ 8.90 (d, J = 2.00 Hz, 1H), 8.57-8.56 (m, 2H), 8.10-8.07 (m, 1H), 7.75 (d, J = 8.40 Hz, 2H), 7.51-7.47 (m, 1H), 7.44 (d, J = 8.40 Hz, 2H), 7.31-7.28 (m, 2H), 6.83 (d, J = 5.20 Hz, 2H), 6.41 (d, J = 6.80 Hz, 1H), 4.38-4.31 (m, 1H), 3.76-3.69 (m, 1H), 3.53 (s, 3H), 2.36-2.20 (m, 1H), 2.06-1.98 (m, 2H), 1.74-1.72 (m, 1H). |

TABLE 4-continued

| Ex | Structure | LC MS (M + H)+ | HPLC Method, RT (min.) & Purity | 1H NMR |
|---|---|---|---|---|
| 168 | 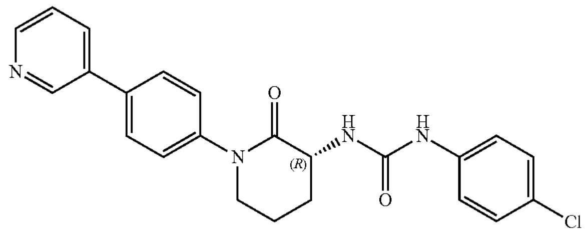 | 421.1 | Method F, RT = 1.739 min, 100% | ¹H NMR (400 MHz, DMSO-d₆): δ 8.93-8.91 (m, 2H), 8.58-8.56 (m, 1H), 8.11-8.08 (m, 1H), 7.76 (d, J = 8.40 Hz, 2H), 7.51-7.41 (m, 5H), 7.27 (d, J = 8.80 Hz, 2H), 6.58 (d, J = 6.80 Hz, 1H), 4.38-4.33 (m, 1H), 3.71-3.68 (m, 2H), 2.31-2.29 (m, 1H), 2.02-1.97 (m, 2H), 1.83-1.76 (m, 1H). |
| 169 | 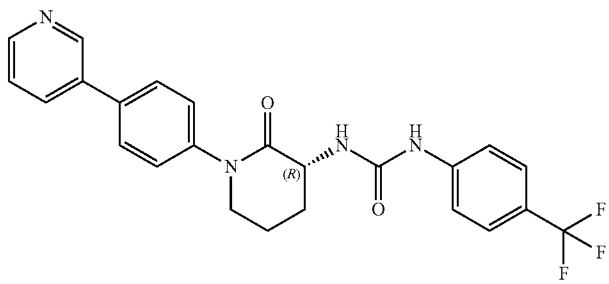 | 455 | Method F, RT = 1.897 min, 98.2% | ¹H NMR (400 MHz, DMSO-d₆): δ 9.23 (s, 1H), 8.91 (d, J = 2.00 Hz, 1H), 8.58-8.56 (m, 1H), 8.11-8.08 (m, 1H), 7.76 (d, J = 8.40 Hz, 2H), 7.62-7.57 (m, 4H), 7.51-7.44 (m, 3H), 6.70 (d, J = 6.80 Hz, 1H), 4.38-4.35 (m, 1H), 3.74-3.69 (m, 2H), 2.33-2.29 (m, 1H), 2.02-2.00 (m, 2H), 1.88-1.85 (m, 1H). |
| 170 | 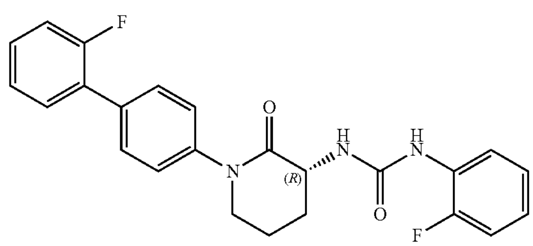 | 422.2 | Method E, RT = 1.906 min, 98.4% | ¹H NMR (400 MHz, METHANOL-d₄): δ 9.04 (br. s., 1H), 8.60 (br. s., 2H), 8.21-8.09 (m, 2H), 7.63-7.52 (m, 2H), 7.48-7.38 (m, 2H), 7.37-7.26 (m, 1H), 7.19 (d, J = 10.0 Hz, 1H), 7.13-7.06 (m, 1H), 6.94 (br. s., 1H), 6.53 (s, 1H), 4.39 (m, 1H), 3.83-3.66 (m, 2H), 2.30 (m, 1H), 2.01 (m, 2H), 1.80 (m, 1H) |
| 171 | 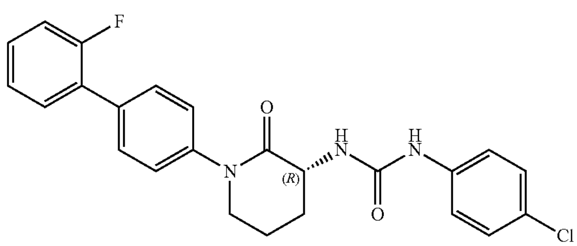 | 439 | Method E, RT = 2.116 min, 94.95% | ¹H NMR (400 MHz, DMSO-d₆): δ 8.94 (s, 1H), 8.62 (s, 1H), 8.03-7.99 (m, 1H), 7.89 (d, J = 8.6 Hz, 1H), 7.62 (td, J = 7.9, 1.6 Hz, 1H), 7.51-7.41 (m, 3H), 7.39-7.32 (m, 2H), 7.30-7.25 (m, 2H), 6.60 (d, J = 7.3 Hz, 1H), 4.48 (dt, J = 12.0, 6.9 Hz, 1H), 4.26 (dt, J = 13.0, 6.5 Hz, 1H), 3.86-3.78 (m, 1H), 2.36-2.27 (m, 1H), 2.03-1.93 (m, 2H), 1.83-1.71 (m, 1H). |
| 172 | 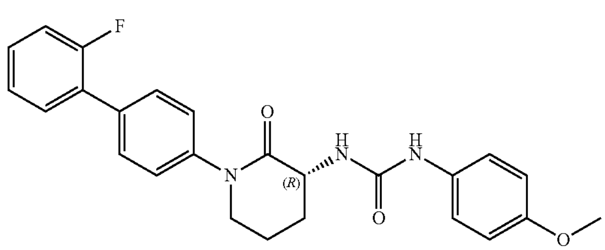 | 434.2 | Method F, RT = 1.778 min, 98.8% | ¹H NMR (400 MHz, DMSO-d₆): δ 8.55 (s, 1H), 7.59-7.53 (m, 3H), 7.46-7.41 (m, 3H), 7.34-7.28 (m, 4H), 6.83 (d, J = 6.80 Hz, 2H), 6.40 (d, J = 6.80 Hz, 1H), 4.35-4.32 (m, 1H), 3.76-3.72 (m, 2H), 3.70 (s, 3H), 2.33-2.29 (m, 1H), 2.01-1.99 (m, 2H), 1.81-1.77 (m, 1H). |

TABLE 4-continued

| Ex | Structure | LC MS (M + H)+ | HPLC Method, RT (min.) & Purity | 1H NMR |
|---|---|---|---|---|
| 173 | 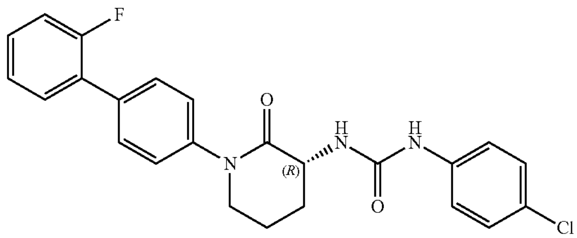 | 438 | Method F, RT = 2.252 min, 100% | ¹H NMR (400 MHz, DMSO-d₆): δ 8.93 (s, 1H), 7.59-7.53 (m, 3H), 7.45-7.41 (m, 5H), 7.34-7.26 (m, 4H), 6.57 (d, J = 6.80 Hz, 1H), 4.40-4.28 (m, 1H), 3.75-3.72 (m, 2H), 2.34-2.33 (m, 1H), 2.02-1.99 (m, 2H), 1.86-1.75 (m, 1H). |
| 174 | 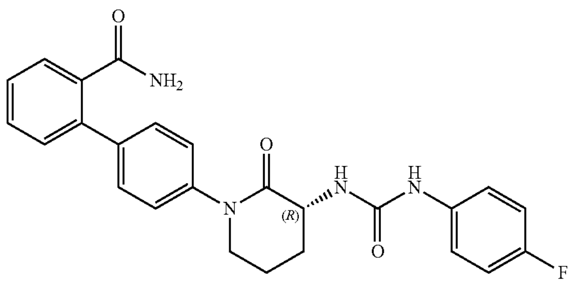 | 447.2 | Method E, RT = 1.292 min, 99.3% | ¹H NMR (400 MHz, METHANOL-d₄): δ 7.59-7.50 (m, 4H), 7.48-7.41 (m, 2H), 7.40-7.34 (m, 4H), 7.04-6.97 (m, 2H), 4.44 (dd, J = 11.5, 6.5 Hz, 1H), 3.90-3.70 (m, 2H), 2.46-2.36 (m, 1H), 2.19-2.08 (m, 2H), 2.01 (m, 1H) |
| 175 | 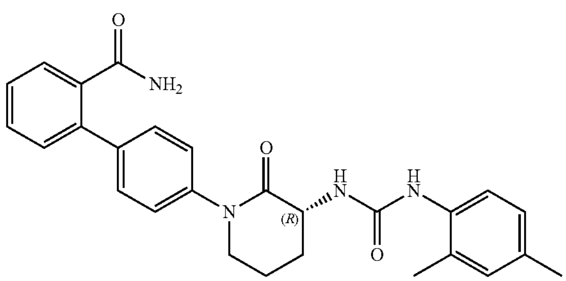 | 457.3 | Method E, RT = 1.406 min, 98.6% | ¹H NMR (400 MHz, METHANOL-d₄): δ 7.60-7.49 (m, 4H), 7.48-7.41 (m, 2H), 7.40-7.32 (m, 3H), 7.05-6.95 (m, 2H), 4.43 (dd, J = 11.3, 6.3 Hz, 1H), 3.88-3.69 (m, 2H), 2.39 (m, 1H), 2.28 (s, 3H), 2.25 (s, 3H), 2.16-2.07 (m, 2H), 2.05-1.94 (m, 1H) |
| 176 | 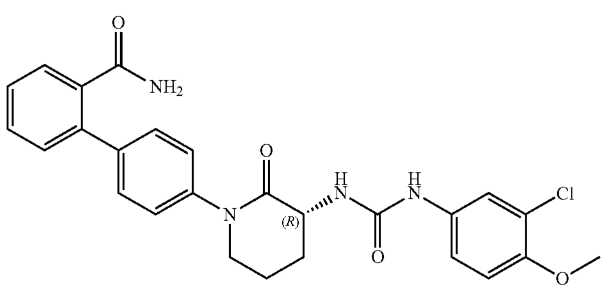 | 493.2 | Method E, RT = 1.384 min, 97.5% | ¹H NMR (400 MHz, METHANOL-d₄): δ 7.59-7.49 (m, 5H), 7.47-7.41 (m, 2H), 7.40-7.34 (m, 2H), 7.21 (dd, J = 8.5, 2.5 Hz, 1H), 6.99 (d, J = 9.0 Hz, 1H), 4.43 (dd, J = 11.5, 6.0 Hz, 1H), 3.89-3.70 (m, 5H), 2.40 (m, 1H), 2.19-2.07 (m, 2H), 2.05-1.93 (m, 1H) |
| 177 | 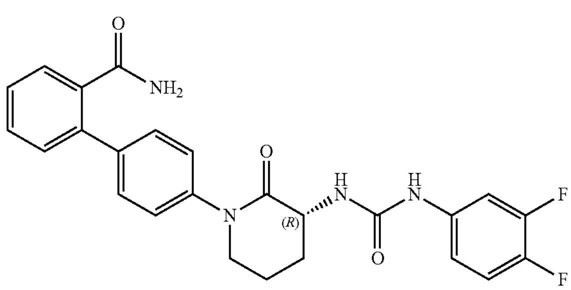 | 469.3 | Method E, RT = 1.406 min, 97.3% | ¹H NMR (400 MHz, METHANOL-d₄): δ 7.60-7.49 (m, 5H), 7.48-7.41 (m, 2H), 7.41-7.34 (m, 2H), 7.19-7.09 (m, 1H), 7.05-6.98 (m, 1H), 4.43 (dd, J = 11.5, 6.0 Hz, 1H), 3.91-3.70 (m, 2H), 2.41 (m, 1H), 2.13 (m, 2H), 1.99 (m, 1H) |

TABLE 4-continued

| Ex | Structure | LC MS (M + H)+ | HPLC Method, RT (min.) & Purity | 1H NMR |
|---|---|---|---|---|
| 178 | 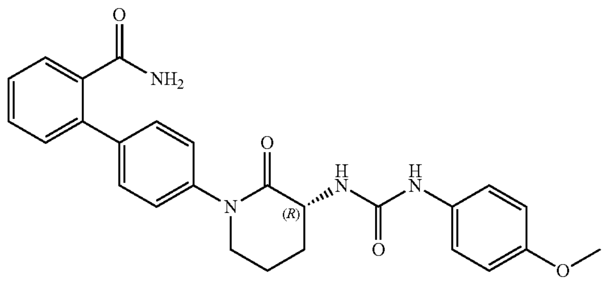 | 459.2 | Method E, RT = 1.223 min, 98.13% | ¹H NMR (400 MHz, METHANOL-d₄): δ 7.58-7.48 (m, 4H), 7.46-7.39 (m, 2H), 7.38-7.33 (m, 2H), 7.28-7.23 (m, 2H), 6.87-6.81 (m, 2H), 4.41 (dd, J = 11.3, 6.8 Hz, 1H), 3.86-3.68 (m, 5H), 2.38 (m, 1H), 2.10 (m, 2H), 1.97 (m, 1H) |
| 179 | 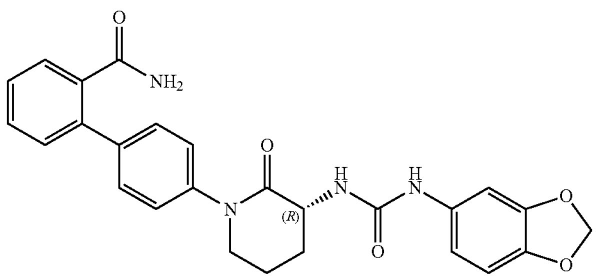 | 473.3 | Method E, RT = 1.221 min, 98.8% | ¹H NMR (400 MHz, METHANOL-d₄): δ 7.58-7.48 (m, 4H), 7.46-7.39 (m, 2H), 7.38-7.32 (m, 2H), 7.05 (d, J = 1.5 Hz, 1H), 6.73-6.65 (m, 2H), 5.89 (s, 2H), 4.40 (dd, J = 11.3, 6.3 Hz, 1H), 3.86-3.67 (m, 2H), 2.43-2.33 (m, 1H), 2.15-2.06 (m, 2H), 2.02-1.89 (m, 1H) |
| 180 | 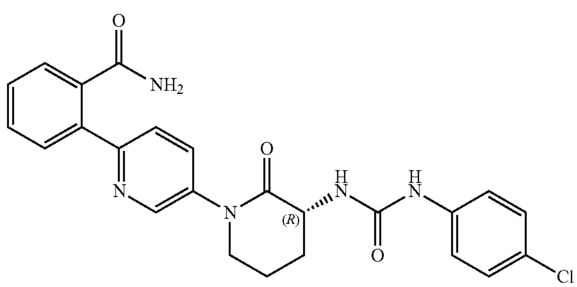 | 464.0 | Method F, RT = 1.570 min, 97.5% | ¹H NMR (400 MHz, DMSO-d₆): δ 8.97 (s, 1H), 8.47-8.42 (m, 1H), 7.86-7.80 (m, 2H), 7.77 (br. s., 1H), 7.57-7.42 (m, 4H), 7.37 (br. s., 1H), 7.31-7.24 (m, 2H), 6.61 (d, J = 7.09 Hz, 1H) 4.55-4.43 (m, 1H), 4.29 (dd, J = 13.0, 5.9 Hz, 1H), 3.87-3.75 (m, 1H), 2.38-2.25 (m, 1H), 2.10-1.98 (m, 2H), 1.84-1.74 (m, 1H) |
| 181 | 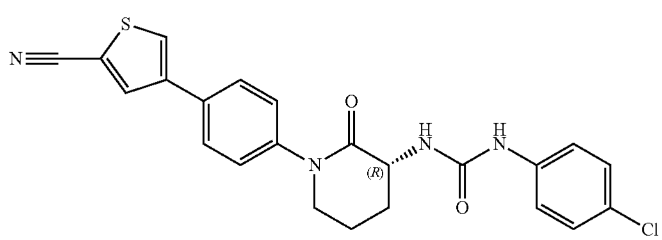 | 451.3 | Method F, RT = 2.095 min, 100% | ¹H NMR (400 MHz, DMSO-d₆): δ 8.93 (s, 1H), 8.47 (d, J = 1.5 Hz, 1H), 8.38 (d, J = 1.2 Hz, 1H), 7.78 (d, J = 8.3 Hz, 2H), 7.41 (dd, J = 14.1, 8.7 Hz, 4H), 7.27 (d, J = 8.8 Hz, 2H), 6.56 (d, J = 6.6 Hz, 1H), 4.40-4.29 (m, 1H), 3.82-3.60 (m, 2H), 2.29 (m, 1H), 2.04-1.93 (m, 2H), 1.81 (m, 1H) |
| 182 | 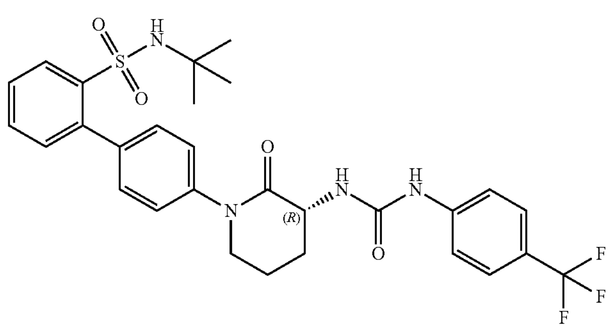 | 589.6 | Method F, RT = 2.498 min, 100% | ¹H NMR (400 MHz, DMSO-d₆): δ 9.23 (s, 1H), 8.05 (dd, J = 8.1, 1.2 Hz, 1H), 7.68-7.53 (m, 6H), 7.45-7.39 (m, 2H), 7.38-7.31 (m, 3H), 6.70 (d, J = 6.6 Hz, 1H), 6.54 (s, 1H), 4.43-4.30 (m, 1H), 3.82-3.69 (m, 2H), 2.38-2.27 (m, 1H), 2.06-1.97 (m, 2H), 1.88-1.74 (m, 1H), 1.01 (s, 9H) |

TABLE 4-continued

| Ex | Structure | LC MS (M + H)+ | HPLC Method, RT (min.) & Purity | 1H NMR |
|---|---|---|---|---|
| 183 | 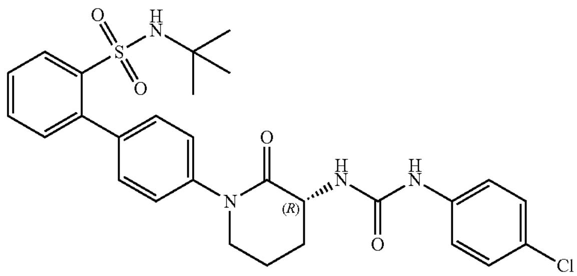 | 555.5 | Method F, RT = 2.105 min, 100% | ¹H NMR (400 MHz, DMSO-d₆): δ 8.93 (s, 1H), 8.04 (dd, J = 7.8, 1.2 Hz, 1H), 7.67-7.53 (m, 2H), 7.46-7.39 (m, 4H), 7.37-7.31 (m, 3H), 7.30-7.23 (m, 2H), 6.60-6.49 (m, 2H), 4.39-4.29 (m, 1H), 3.83-3.67 (m, 2H), 2.32-2.25 (m, 1H), 2.04-1.95 (m, 2H), 1.85-1.74 (m, 1H), 1.00 (s, 9H) |
| 184 | 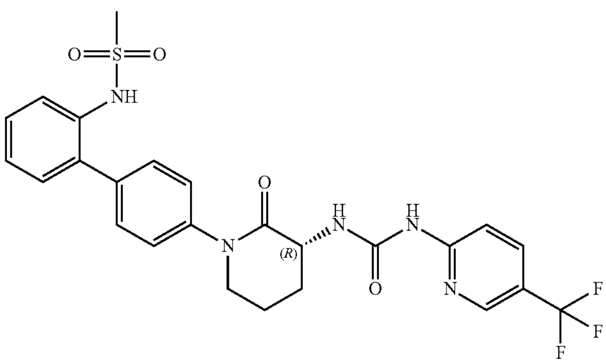 | 548.0 | Method F, RT = 1.96 min, 98.67%, | ¹H NMR (400 MHz, DMSO-d₆): δ 9.86 (s, 1H), 9.01-8.96 (m, 1H), 8.58-8.52 (m, 1H), 8.18-8.11 (m, 1H), 8.09-8.02 (m, 1H), 7.76-7.70 (m, 1H), 7.48-7.46 (m, 2H), 7.45-7.32 (m, 6H), 4.50-4.40 (m, 1H), 3.85-3.66 (m, 2H), 2.73 (s, 3H), 2.40-2.31 (m, 1H), 2.08-1.99 (m, 2H), 1.90-1.79 (m, 1H) |
| 185 | 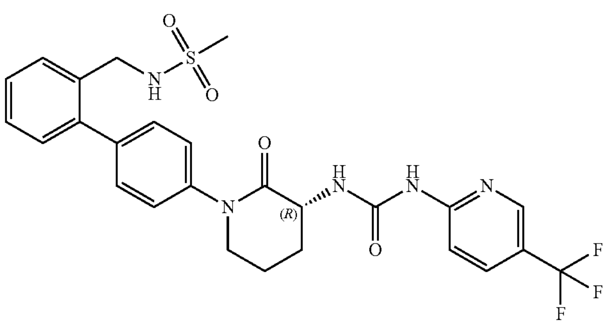 | 562.0 | Method F, RT = 1.97 min, 96.7% | ¹H NMR (400 MHz, DMSO-d₆): δ 9.82 (s, 1H) 9.48 (br. s., 1H) 8.56 (s, 1H) 8.18 (br. s., 1H) 8.06 (dd, J = 8.80, 2.45 Hz, 1H) 7.95 (s, 1H) 7.72 (d, J = 9.05 Hz, 1H) 7.59 (d, J = 7.83 Hz, 1H) 7.29-7.49 (m, 3H) 7.20-7.27 (m, 1H) 7.03-7.11 (m, 2H) 4.40-4.50 (m, 1H) 4.12 (d, J = 6.36 Hz, 2H) 3.69-3.85 (m, 2H) 2.79 (s, 3H) 2.32-2.39 (m, 1H) 1.98-2.08 (m, 2H) 1.78-1.91 (m, 1H) |
| 186 | 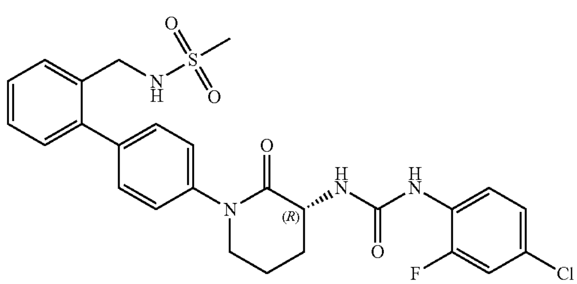 | 545.0 | Method F, RT = 2.01 min, 97.9% | ¹H NMR (400 MHz, DMSO-d₆): δ 8.71 (s, 1H) 8.16 (t, J = 9.05 Hz, 1H) 7.95 (s, 1H) 7.59 (d, J = 7.83 Hz, 1H) 7.30-7.49 (m, 3H) 7.25 (d, J = 7.58 Hz, 1H) 7.18 (d, J = 9.05 Hz, 1H) 7.04-7.14 (m, 4 H) 6.51 (s, 1H) 4.32-4.41 (m, 1H) 4.12 (d, J = 6.11 Hz, 2H) 3.67-3.81 (m, 2H) 2.79 (s, 3H) 2.32 (m, 1H) 1.96-2.05 (m, 2H) 1.74-1.86 (m, 1H) |
| 187 | 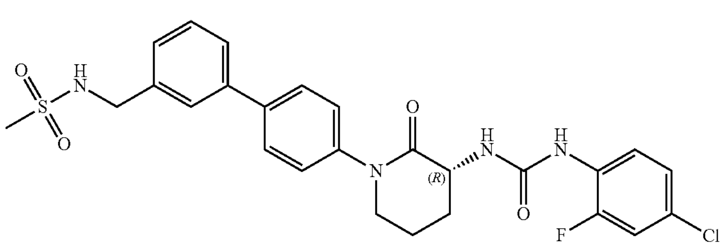 | 545.1 | Method F, RT = 1.968 min, 100% | ¹H NMR (400 MHz, DMSO-d₆): δ 8.71 (s, 1H), 8.16 (t, J = 8.9 Hz, 1H), 7.73-7.63 (m, 3H), 7.59 (d, J = 6.1 Hz, 2H), 7.49-7.32 (m, 5H), 7.18 (d, J = 8.6 Hz, 1H), 7.12 (d, J = 6.6 Hz, 1H), 4.41-4.31 (m, 1H), 4.24 (d, J = 6.1 Hz, 2H), 3.73 (tt, J = 12.4, 6.1 Hz, 2H), 2.88 (s, 3H), 2.31 (m, 1H), 2.06-1.95 (m, 2H), 1.86-1.73 (m, 1H) |

TABLE 4-continued

| Ex | Structure | LC MS (M + H)+ | HPLC Method, RT (min.) & Purity | 1H NMR |
|---|---|---|---|---|
| 188 | 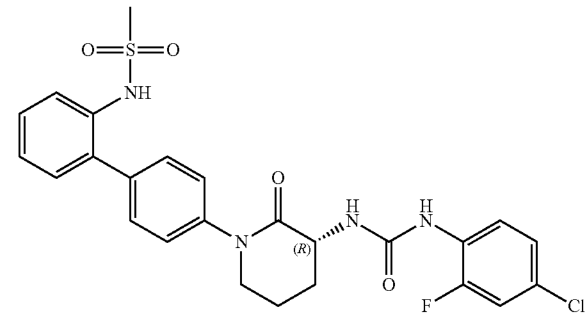 | 531.0 | Method F, RT = 1.985 min, 96% | ¹H NMR (400 MHz, DMSO-d₆): δ 8.99 (s, 1H), 8.70 (s, 1H), 8.15 (t, J = 8.8 Hz, 1H), 7.49 (d, J = 8.1 Hz, 2H), 7.45-7.32 (m, 7H), 7.18 (d, J = 8.6 Hz, 1H), 7.11 (d, J = 6.6 Hz, 1H), 4.42-4.30 (m, 1H), 3.82-3.64 (m, 2H), 2.75-2.70 (m, 3H), 2.30 (m, 1H), 2.05-1.96 (m, 2H), 1.85-1.72 (m, 1H) |
| 189 | 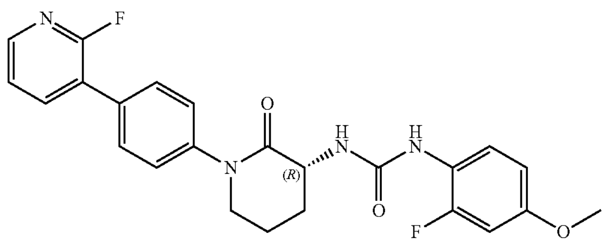 | 453.1 | Method F, RT = 1.728 min, 100% | ¹H NMR (400 MHz, DMSO-d₆): δ 8.32 (s, 1H), 8.25 (d, J = 4.6 Hz, 1H), 8.14 (ddd, J = 10.1, 7.8, 1.8 Hz, 1H), 7.85 (t, J = 9.2 Hz, 1H), 7.64 (d, J = 7.1 Hz, 2H), 7.51-7.42 (m, 3H), 6.90-6.81 (m, 2H), 6.70 (dd, J = 8.4, 2.8 Hz, 1H), 4.40-4.30 (m, 1H), 3.82-3.67 (m, 5H), 2.30 (m, 1H), 2.04-1.94 (m, 2H), 1.85-1.73 (m, 1H) |
| 190 | 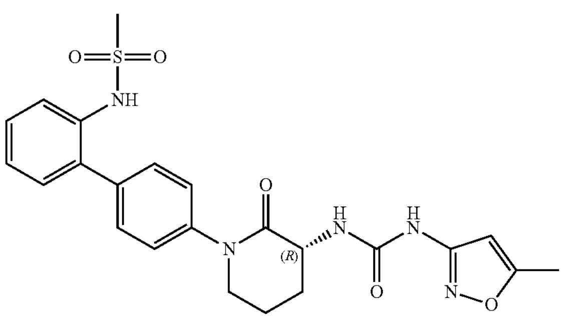 | 484.0 | Method F, RT = 1.607 min, 97% | ¹H NMR (400 MHz, DMSO-d₆): δ 9.50 (s, 1H), 8.98 (s, 1H), 7.48 (d, J = 8.6 Hz, 2H), 7.44-7.33 (m, 6H), 7.00 (d, J = 6.8 Hz, 1H), 6.38 (s, 1H), 4.41-4.30 (m, 1H), 3.80-3.64 (m, 2H), 2.74-2.68 (m, 3H), 2.35-2.23 (m, 4H), 2.04-1.96 (m, 2H), 1.81 (m, 1H) |
| 191 | 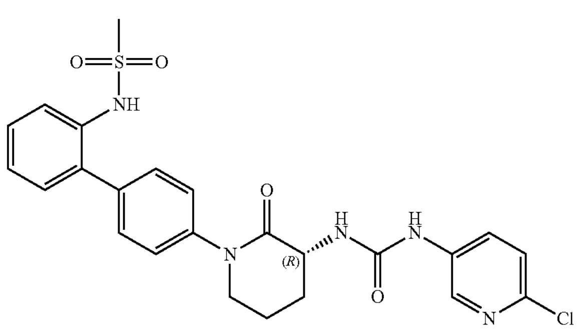 | 514.0 | Method F, RT = 1.677 min, 96% | ¹H NMR (400 MHz, DMSO-d₆): δ 9.13 (s, 1H), 8.40 (d, J = 2.7 Hz, 1H), 7.93 (dd, J = 8.7, 2.8 Hz, 1H), 7.51-7.45 (m, 2H), 7.44-7.32 (m, 8H), 6.73 (d, J = 6.8 Hz, 1H), 4.39-4.29 (m, 1H), 3.80-3.65 (m, 2H), 2.74-2.69 (m, 3H), 2.28 (m, 1H), 2.04-1.96 (m, 2H), 1.84 (m, 1H) |

TABLE 4-continued

| Ex | Structure | LC MS (M + H)+ | HPLC Method, RT (min.) & Purity | 1H NMR |
|---|---|---|---|---|
| 192 | 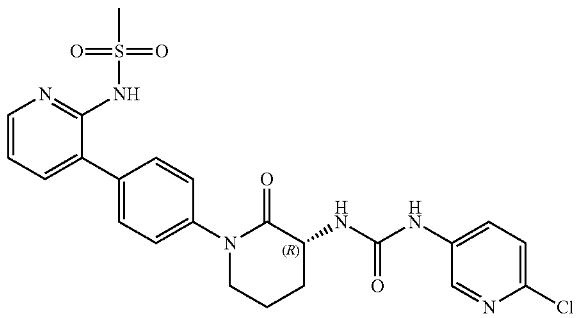 | 516.9 | Method F, RT = 1.41 min, 94.7% | ¹H NMR (400 MHz, DMSO-$d_6$): δ 9.14 (s, 1H) 8.40 (d, J = 2.69 Hz, 1H) 8.21 (br. s., 1H) 7.93 (dd, J = 8.68, 2.81 Hz, 1H) 7.72 (dd, J = 7.34, 1.71 Hz, 1H) 7.54 (d, J = 8.56 Hz, 2H) 7.33-7.43 (m, 4 H) 7.12 (br. s., 1H) 6.74 (d, J = 6.85 Hz, 1H) 4.30-4.38 (m, 1H) 3.67-3.79 (m, 2H) 3.21 (s, 3H) 2.23-2.35 (m, 1H) 1.95-2.03 (m, 2H) 1.75-1.88 (m, 1H) |
| 193 | 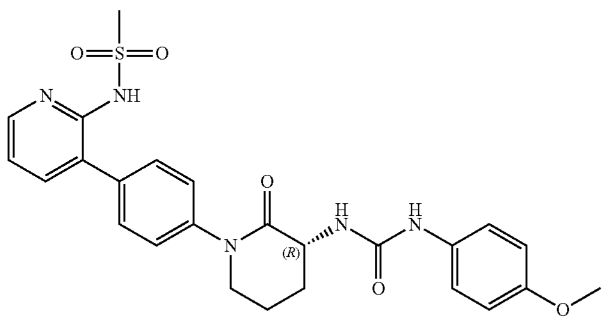 | 510.0 | Method F, RT = 1.43 min, 99.1% | ¹H NMR (400 MHz, DMSO-$d_6$): δ 9.65 (br. s, 1H) 8.55 (s, 1H) 8.33 (br. s., 1H) 7.93 (s, 1H) 7.74 (d, J = 7.09 Hz, 1H) 7.52 (d, J = 7.82 Hz, 2H) 7.39 (d, J = 7.82 Hz, 2H) 7.28 (d, J = 9.05 Hz, 2H) 6.82 (d, J = 9.05 Hz, 2H) 6.41 (d, J = 6.60 Hz, 1H) 4.28-4.37 (m, 1H) 3.70-3.79 (m, 2H) 3.68 (s, 3H) 3.30 (s, 3H) 2.28 (m, 1H) 1.95-2.04 (m, 2H) 1.72-1.84 (m, 1H) |
| 194 | 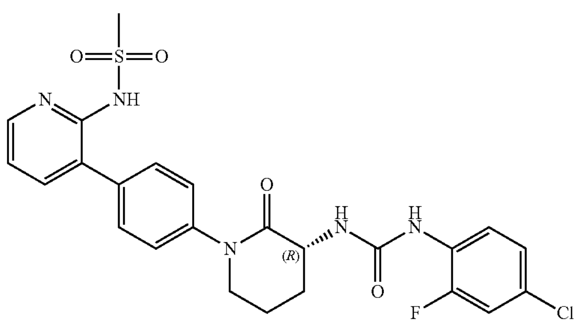 | 532.0 | Method F, RT = 1.74 min, 98.2% | ¹H NMR (400 MHz, DMSO-$d_6$): δ 8.70 (s, 1H) 8.13 (t, J = 8.93 Hz, 1H) 7.93 (s, 1H) 7.74 (d, J = 7.09 Hz, 1H) 7.53 (d, J = 7.83 Hz, 2H) 7.34-7.43 (m, 3H) 7.17 (d, J = 9.29 Hz, 1H) 7.10 (d, J = 7.09 Hz, 1H) 4.31-4.40 (m, 1H) 3.68-3.79 (m, 5 H) 2.30 (m, 1H) 1.95-2.04 (m, 2H) 1.73-1.86 (m, 1H) |
| 195 | 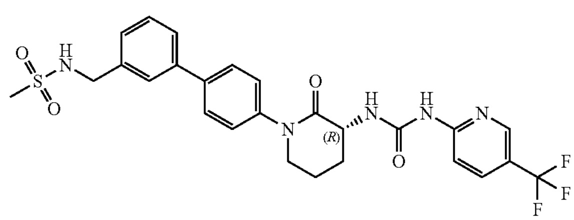 | 562.0 | Method F, RT = 1.928 min, 94% | ¹H NMR (400 MHz, DMSO-$d_6$): δ 9.81 (s, 1H), 8.55 (s, 1H), 8.14 (d, J = 5.4 Hz, 1H), 8.06 (dd, J = 9.0, 2.7 Hz, 1H), 7.76-7.64 (m, 4H), 7.59 (d, J = 6.4 Hz, 2H), 7.49-7.31 (m, 4H), 4.49-4.37 (m, 1H), 4.24 (d, J = 6.4 Hz, 2H), 3.85-3.65 (m, 2H), 2.92-2.85 (m, 3H), 2.40-2.29 (m, 1H), 2.09-1.96 (m, 2H), 1.86 (m, 1H) |
| 196 | 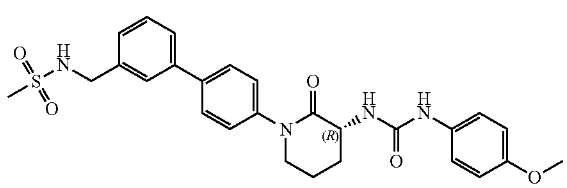 | 523.1 | Method F, RT = 1.665 min, 100% | ¹H NMR (400 MHz, DMSO-$d_6$): δ 8.56 (s, 1H), 7.72-7.64 (m, 3H), 7.62-7.55 (m, 2H), 7.49-7.25 (m, 6H), 6.86-6.77 (m, 2H), 6.41 (d, J = 6.8 Hz, 1H), 4.38-4.28 (m, 1H), 4.24 (d, J = 6.1 Hz, 2H), 3.81-3.66 (m, 5H), 2.88 (s, 3H), 2.30 (m, 1H), 2.04-1.94 (m, 2H), 1.86-1.73 (m, 1H) |

TABLE 4-continued

| Ex | Structure | LC MS (M + H)+ | HPLC Method, RT (min.) & Purity | 1H NMR |
|---|---|---|---|---|
| 197 | 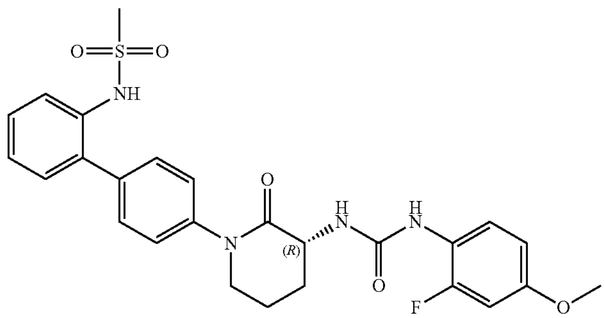 | 527.1 | Method F, RT = 1.737 min, 95% | ¹H NMR (400 MHz, DMSO-d₆): δ 8.99 (s, 1H), 8.32 (s, 1H), 7.92-7.80 (m, 1H), 7.49 (d, J = 8.6 Hz, 2H), 7.45-7.32 (m, 6H), 6.89-6.81 (m, 2H), 6.70 (dd, J = 9.5, 2.4 Hz, 1H), 4.40-4.30 (m, 1H), 3.81-3.68 (m, 5H), 2.72 (s, 3H), 2.30 (m, 1H), 2.05-1.93 (m, 2H), 1.86-1.72 (m, 1H) |
| 198 | 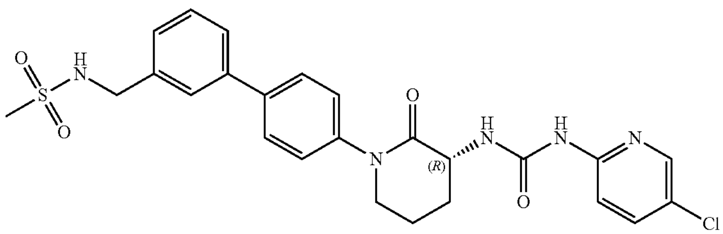 | 528.1 | Method F, RT = 1.816 min, 97% | ¹H NMR (400 MHz, DMSO-d₆): δ 9.48 (s, 1H), 8.22 (d, J = 2.4 Hz, 1H), 7.98 (d, J = 6.4 Hz, 1H), 7.80 (dd, J = 9.0, 2.7 Hz, 1H), 7.72-7.64 (m, 3H), 7.63-7.55 (m, 3H), 7.48-7.38 (m, 3H), 7.35 (d, J = 7.3 Hz, 1H), 4.47-4.38 (m, 1H), 4.24 (d, J = 6.4 Hz, 2H), 3.83-3.65 (m, 2H), 2.88 (s, 3H), 2.37-2.27 (m, 1H), 2.06-1.95 (m, 2H), 1.90-1.77 (m, 1H) |
| 199 | 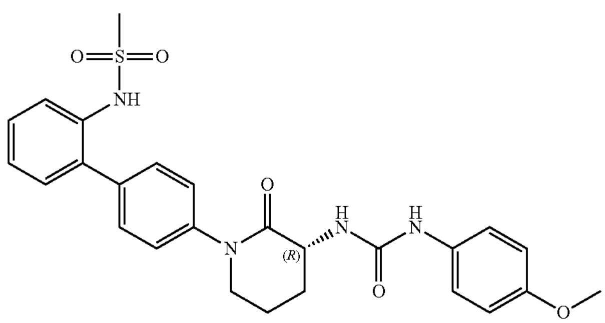 | 509.1 | Method F, RT = 1.674 min, 100% | ¹H NMR (400 MHz, DMSO-d₆): δ 8.98 (br. s., 1H), 8.59 (s, 1H), 7.49 (d, J = 8.3 Hz, 2H), 7.45-7.26 (m, 8H), 6.86-6.78 (m, 2H), 6.43 (d, J = 6.8 Hz, 1H), 4.39-4.29 (m, 1H), 3.80-3.65 (m, 5H), 2.72 (s, 3H), 2.32-2.25 (m, 1H), 2.05-1.94 (m, 2H), 1.85-1.72 (m, 1H) |
| 200 | 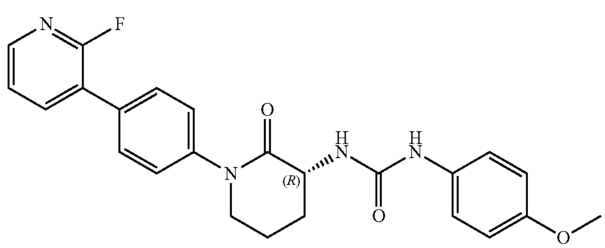 | 435.0 | Method F, RT = 1.647 min, 100% | ¹H NMR (400 MHz, DMSO-d₆): δ 8.56 (s, 1H), 8.24 (d, J = 4.9 Hz, 1H), 8.14 (dd, J = 10.0, 8.1 Hz, 1H), 7.64 (d, J = 7.1 Hz, 2H), 7.51-7.42 (m, 3H), 7.30 (d, J = 9.0 Hz, 2H), 6.82 (d, J = 8.8 Hz, 2H), 6.41 (d, J = 6.4 Hz, 1H), 4.39-4.29 (m, 1H), 3.81-3.67 (m, 5H), 2.30 (m, 1H), 2.05-1.96 (m, 2H), 1.86-1.73 (m, 1H) |
| 201 | 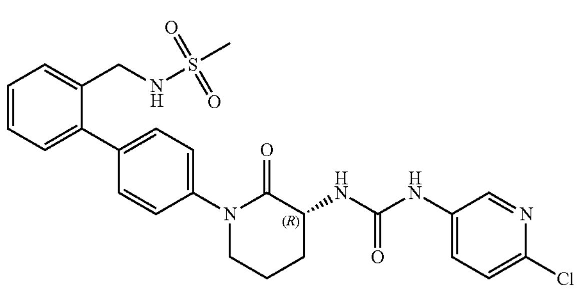 | 528.0 | Method F, RT = 1.69 min, 95.5% | ¹H NMR (400 MHz, DMSO-d₆): δ 9.14 (s, 1H) 8.41 (d, J = 2.69 Hz, 1H) 7.95 (dd, J = 8.80, 2.69 Hz, 1H) 7.59 (d, J = 7.34 Hz, 2H) 7.33-7.48 (m, 8 H) 7.25 (d, J = 7.34 Hz, 1H) 6.74 (d, J = 6.85 Hz, 1H) 4.31-4.40 (m, 1H) 4.12 (d, J = 5.87 Hz, 2H) 3.69-3.81 (m, 2H) 2.80 (s, 3H) 2.30 (m, 1H) 1.96-2.06 (m, 2H) 1.76-1.89 (m, 1H) |

TABLE 4-continued

| Ex | Structure | LC MS (M + H)+ | HPLC Method, RT (min.) & Purity | 1H NMR |
|---|---|---|---|---|
| 202 | 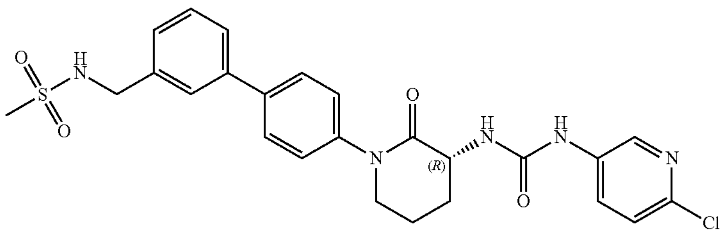 | 528.1 | Method F, RT = 1.646 min, 98% | ¹H NMR (400 MHz, DMSO-d₆): δ 9.14 (s, 1H), 8.41 (d, J =2.9 Hz, 1H), 7.94 (dd, J = 8.9, 2.6 Hz, 1H), 7.73-7.63 (m, 3H), 7.59 (d, J = 5.4 Hz, 2H), 7.50-7.30 (m, 5H), 6.74 (d, J = 6.8 Hz, 1H), 4.41-4.31 (m, 1H), 4.24 (d, J = 6.4 Hz, 2H), 3.82-3.64 (m, 2H), 2.88 (s, 3H), 2.30 (m, 1H), 2.00 (m, 2H), 1.84 (m, 1H) |
| 203 | 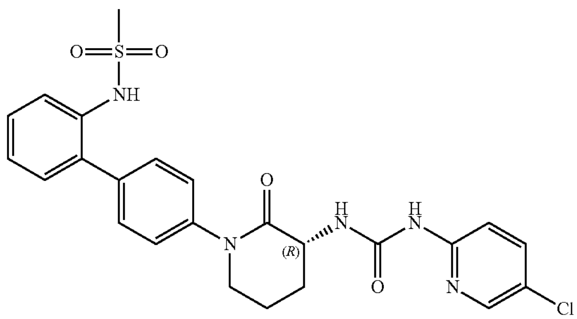 | 539.9 | Method F, RT = 1.79 min, 95.46%, | ¹H NMR (400 MHz, DMSO-d₆): δ 9.86 (s, 1H), 9.01 (s, 1H), 8.58-8.52 (m, 1H), 8.18-8.11 (m, 1H), 8.09-8.02 (m, 1H), 7.76-7.70 (m, 1H), 7.48 (s, 2H), 7.45-7.32 (m, 6H), 4.50-4.40 (m, 1H), 3.85-3.66 (m, 2H), 2.73 (s, 3H), 2.40-2.31 (m, 1H), 2.08-1.99 (m, 2H), 1.90-1.79 (m, 1H) |
| 204 | 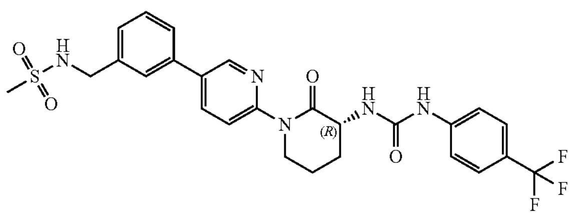 | 562.1 | Method E, RT = 1.916 min, 97.167% | ¹H NMR (400 MHz, DMSO-d₆): δ 9.24 (s, 1H), 8.75 (d, J = 2.4 Hz, 1H), 8.11 (dd, J = 8.6, 2.4 Hz, 1H), 7.88 (d, J = 8.6 Hz, 1H), 7.70 (s, 1H), 7.67-7.56 (m, 6H), 7.49 (t, J = 7.8 Hz, 1H), 7.40 (d, J = 7.6 Hz, 1H), 6.73 (d, J = 7.1 Hz, 1H), 4.54-4.46 (m, 1H), 4.30-4.21 (m, 3H), 3.87-3.79 (m, 1H), 2.89 (s, 3H), 2.37-2.28 (m, 1H), 2.04-1.94 (m, 2H), 1.85-1.73 (m, 1H). |
| 205 | 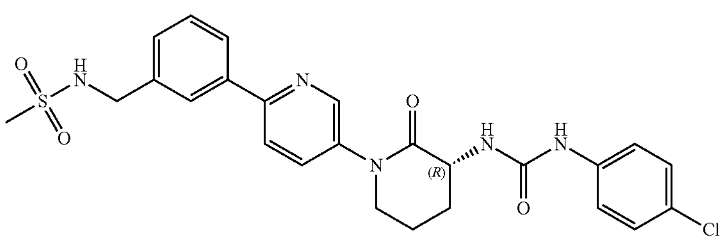 | 528.1 | Method E, RT = 1.761 min, 98.58% | ¹H NMR (400 MHz, DMSO-d₆): δ 8.95 (s, 1H), 8.75 (d, J = 2.4 Hz, 1H), 8.10 (dd, J = 8.7, 2.6 Hz, 1H), 7.88 (d, J = 8.6 Hz, 1H), 7.73-7.57 (m, 3H), 7.51-7.37 (m, 4H), 7.27 (d, J = 8.8 Hz, 2H), 6.61 (d, J = 6.8 Hz, 1H), 4.52-4.44 (m, 1H), 4.29-4.21 (m, 3H), 3.86-3.77 (m, 1H), 2.89 (s, 3H), 2.31 (m, 1H), 2.04-1.91 (m, 2H), 1.83-1.71 (m, 1H). |
| 206 | 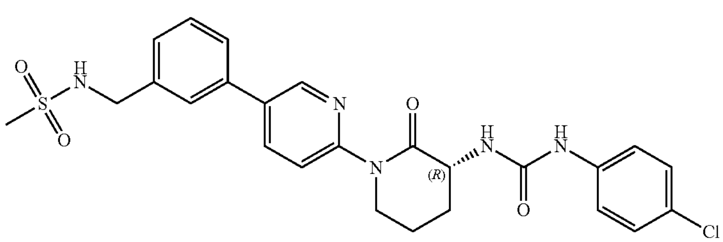 | 528.1 | Method E, RT = 1.758 min, 97.024% | ¹H NMR (400 MHz, DMSO-d₆): δ 8.95 (s, 1H), 8.75 (d, J = 2.2 Hz, 1H), 8.11 (dd, J = 8.6, 2.4 Hz, 1H), 7.87 (d, J = 8.6 Hz, 1H), 7.72-7.37 (m, 7H), 7.28 (d, J = 9.0 Hz, 2H), 6.60 (d, J = 7.1 Hz, 1H), 4.52-4.43 (m, 1H), 4.29-4.20 (m, 3H), 3.87-3.78 (m, 1H), 2.91-2.86 (m, 3H), 2.31 (m, 1H), 2.03-1.94 (m, 2H), 1.83-1.72 (m, 1H). |

TABLE 4-continued

| Ex | Structure | LC MS (M+H)+ | HPLC Method, RT (min.) & Purity | 1H NMR |
|---|---|---|---|---|
| 207 | 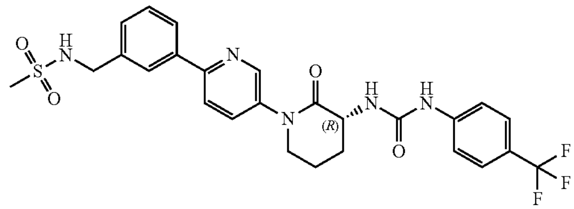 | 562.1 | Method E, RT = 1.914 min, 97.60% | ¹H NMR (400 MHz, DMSO-d₆): δ 9.24 (s, 1H), 8.75 (d, J = 2.4 Hz, 1H), 8.11 (dd, J = 8.8, 2.4 Hz, 1H), 7.88 (d, J = 8.6 Hz, 1H), 7.72-7.55 (m, 7H), 7.49 (t, J = 7.6 Hz, 1H), 7.43-7.37 (m, 1H), 6.73 (d, J = 7.1 Hz, 1H), 4.54-4.46 (m, 1H), 4.29-4.22 (m, 3H), 3.87-3.78 (m, 1H), 2.89 (s, 3H), 2.37-2.28 (m, 1H), 2.04-1.94 (m, 2H), 1.85-1.73 (m, 1H). |
| 208 | 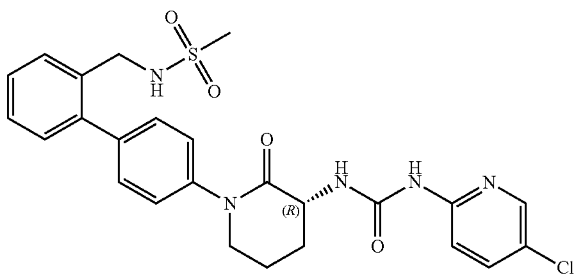 | 528.0 | Method F, RT = 1.85 min, 94.9% | ¹H NMR (400 MHz, DMSO-d₆): δ 9.49 (s, 1H) 8.22 (d, J = 2.45 Hz, 1H) 8.01 (m, 1H) 7.80 (dd, J = 8.93, 2.81 Hz, 1H) 7.56-7.63 (m, 2H) 7.33-7.48 (m, 6 H) 7.25 (d, J = 7.58 Hz, 1H) 6.51 (s, 1H) 4.37-4.47 (m, 1H) 4.12 (d, J = 5.87 Hz, 2H) 3.65-3.83 (m, 2H) 2.79 (s, 3H) 2.29-2.38 (m, 1H) 1.97-2.06 (m, 2H) 1.77-1.88 (m, 1H) |
| 209 | 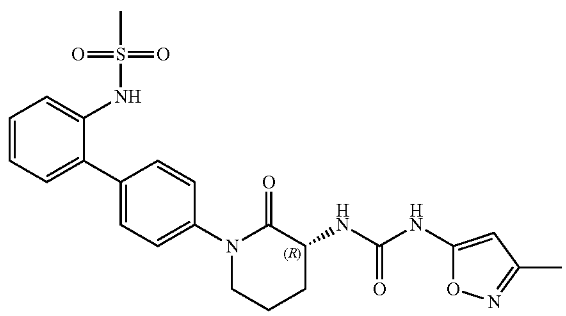 | 484.0 | Method F, RT = 1.606 min, 99% | ¹H NMR (400 MHz, DMSO-d₆): δ 10.22 (s, 1H), 7.49 (d, J = 8.3 Hz, 2H), 7.44-7.30 (m, 7H), 6.82 (d, J = 6.8 Hz, 1H), 5.86 (s, 1H), 4.42-4.29 (m, 1H), 3.82-3.63 (m, 2H), 2.72 (s, 3H), 2.30 (m, 1H), 2.13 (s, 3H), 2.05-1.94 (m, 2H), 1.88-1.74 (m, 1H) |
| 210 | 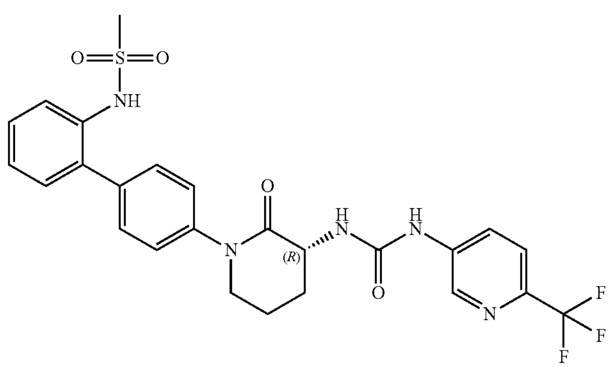 | 548.0 | Method F, RT = 1.875 min, 99% | ¹H NMR (400 MHz, DMSO-d₆): δ 9.44 (s, 1H), 8.97 (br. s., 1H), 8.68 (d, J = 2.7 Hz, 1H), 8.12 (d, J = 2.4 Hz, 1H), 7.76 (d, J = 8.8 Hz, 1H), 7.52-7.44 (m, 2H), 7.43-7.32 (m, 6H), 6.85 (d, J = 6.8 Hz, 1H), 4.43-4.30 (m, 1H), 3.81-3.62 (m, 2H), 2.72 (s, 3H), 2.35-2.24 (m, 1H), 2.04-1.96 (m, 2H), 1.91-1.78 (m, 1H) |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula I

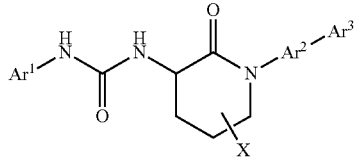

where:
- Ar¹ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl, and is substituted with 1-3 substituents selected from cyano, halo, alkyl, haloalkyl, alkoxy, haloalkoxy, alkylthio, and $SO_2R^6$;
- Ar² is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;
- Ar³ is aryl or heteroaryl, and is substituted with 0-3 substituents selected from cyano, halo, alkyl, haloalkyl, hydroxyalkyl, alkoxyalkyl, $(NR^1R^2)$alkyl, $(CO_2R^3)$alkyl, $(CONR^4R^5)$alkyl, $(SO_2R^6)$alkyl, hydroxy, alkoxy, haloalkoxy, cycloalkoxy, $NR^1R^2$, $CO_2R^3$, $CONR^4R^5$, $SO_2R^6$, oxo, aryl, and heteroaryl;
- $R^1$ is hydrogen, alkyl, alkylcarbonyl, alkylsulfonyl, or haloalkylsulfonyl;
- $R^2$ is hydrogen or alkyl;
- or $NR^1R^2$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and
- $R^3$ is alkyl or haloalkyl;
- $R^4$ is hydrogen, alkyl, or $(R^7R^8N)$alkyl;
- $R^5$ is hydrogen or alkyl;
- or $NR^4R^5$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;
- $R^6$ is alkyl or $R^7R^8N$;
- $R^7$ is hydrogen or alkyl;
- $R^8$ is hydrogen or alkyl;
- or $NR^7R^8$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and
- X is hydrogen, halo, hydroxy, or alkoxy;
- or a pharmaceutically acceptable salt thereof.

2. The compound of claim 1 where:
- Ar¹ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl, and is substituted with 1-3 substituents selected from cyano, halo, alkyl, haloalkyl, alkoxy, haloalkoxy, alkylthio, and $SO_2R^6$;
- Ar² is phenyl or pyridinyl substituted with 0-3 substituents selected from from cyano, halo, alkyl, haloalkyl, alkoxy, and haloalkoxy;
- Ar³ is phenyl, pyridinyl, pyridazinyl, pyrimidinyl, pyrazinyl, pyridinonyl, pyrrolyl, furanyl, thienyl, pyrazolyl, isoxazolyl, isothiazolyl, imidazolyl, oxazolyl, thiazolyl, triazinyl, oxadiazolyl, thiadiazolyl, or benzodioxyl and is substituted with 0-3 substituents selected from cyano, halo, alkyl, haloalkyl, hydroxyalkyl, alkoxyalkyl, $(NR^1R^2)$alkyl, hydroxy, alkoxy, haloalkoxy, cycloalkoxy, $NR^1R^2$, $CO_2R^3$, $CONR^4R^5$, and $SO_2R^6$;
- $R^1$ is hydrogen, alkyl, alkylcarbonyl, alkylsulfonyl, or haloalkylsulfonyl;
- $R^2$ is hydrogen or alkyl;
- or $NR^1R^2$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;
- $R^3$ is alkyl;
- $R^4$ is hydrogen, alkyl, or $(R^7R^8N)$alkyl;
- $R^5$ is hydrogen or alkyl;
- or $NR^4R^5$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy;
- $R^6$ is alkyl or RIM;
- $R^7$ is hydrogen or alkyl;
- $R^8$ is hydrogen or alkyl;
- or $NR^7R^8$ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and
- X is hydrogen, halo, hydroxy, or alkoxy;
- or a pharmaceutically acceptable salt thereof.

3. The compound of claim 2 where AO is phenyl, pyridinyl, pyridazinyl, thiazolyl, or benzodioxoyl and is substituted with 1-3 substituents selected from cyano, halo, alkyl, haloalkyl, alkoxy, haloalkoxy, and alkylthio; Ar² is phenyl or pyridinyl and is substituted with 0-3 substituents selected from cyano and halo; Ar³ is phenyl, pyridinyl, pyrimidinyl, pyridinonyl, thienyl, pyrazolyl, isoxazolyl, benzodioxoyl, and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

4. The compound of claim 1 where AO is phenyl or pyridinyl and is -1,4-substituted with 1 halo, alkyl, haloalkyl, alkoxy, haloalkoxy or alkylthio substituent with respect to the nitrogen attached to Ar¹ and also is substituted with 0-2 fluoro substituents.

5. The compound of claim 1 where Ar² is phenyl or pyridinyl and is substituted with 0-3 substituents selected from cyano, halo, alkyl, haloalkyl, alkoxy, and haloalkoxy.

6. The compound of claim 1 where Ar² is -1,4-substituted with respect to the nitrogen and the Ar³ to which it is attached.

7. The compound of claim 1 where Ar² is phenyl or pyridinyl and is -1,4-substituted with respect to the nitrogen and the Ar³ to which it is attached and is substituted with 0-3 substituents selected from cyano, halo, alkyl, haloalkyl, alkoxy, and haloalkoxy.

8. The compound of claim 1 where Ar³ is phenyl, pyridinyl, pyrimidinyl, pyridinonyl, thienyl, pyrazolyl, isoxazolyl, benzodioxoyl, and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

9. The compound of claim 1 where Ar³ is phenyl or pyridinyl and is substituted with 0-3 substituents selected from cyano, halo, alkyl, haloalkyl, hydroxyalkyl, $(NR^1R^2)$alkyl, alkoxy, haloalkoxy, $NR^1R^2$, $CO_2R^3$, $CONR^4R^5$, and $SO_2R^6$.

10. The compound of claim 1 where X is hydrogen.

11. The compound of claim 1 selected from the group consisting of 1-(4-chlorophenyl)-3-[(3R)-1-{2'-methanesulfonamido-[1, 1'-biphenyl]-4-yl}-2-oxopiperidin-3-yl] urea;

1-[(3R)-1-{2'-methanesulfonamido-[1, 1'-biphenyl]-4-yl}-2-oxopiperidin-3-yl]-3-[4-(trifluoromethyl)phenyl] urea;

4'-[(3R)-3-{[(4-chlorophenyl)carbamoyl]amino}-2-oxopiperidin-1-yl]-3'-fluoro-[1,1'-biphenyl]-2-carboxamide;

1-(4-chlorophenyl)-3-[(3R)-1-{2'-methanesulfonyl-]1,1'-biphenyl]-4-yl}-2-oxopiperidin-3-yl]urea;

1-(4-chlorophenyl)-3-[(3R)-1-{3-fluoro-2'-methanesulfonyl-]1,1'-biphenyl]-4-yl}-2-oxopiperidin-3-yl]urea;

3-[(3R)-1-]2'-(methanesulfonamidomethyl)-]1,1'-biphenyl]-4-yl]-2-oxopiperidin-3-yl]-1-[4-(trifluoromethyl)phenyl]urea;

3-(4-chloro-2-fluorophenyl)-1-[(3R)-1]3'-(methanesulfonamidomethyl)-]1,1'-biphenyl]-4-yl]-2-oxopiperidin-3-yl]urea;

1-(4-chlorophenyl)-3-[(3R)-1-[4-(2-methanesulfonamidopyridin-3-yl)phenyl]-2-oxopiperidin-3-yl]urea;

3-(6-chloropyridin-3-yl)-1-[(3R)-1-{2'-methanesulfonamido-]1,1'-biphenyl]-4-yl-2-oxopiperidin-3-yl]urea;

3-(6-chloropyridin-3-yl)-1-[(3R)-1 43'-(methanesulfonamidomethyl)-[1,1'-biphenyl]-4-yl]-2-oxopiperidin-3-yl]urea;

3-[(3R)-1-[4-(2-methanesulfonamidopyridin-3-yl)phenyl]-2-oxopiperidin-3-yl]-1-]4-(trifluoromethyl)phenyl]urea;

3-[(3R)-1-(2-methanesulfonamidophenyl)pyridin-2-yl]-2-oxopiperidin-3-yl]-1-]4-(trifluoromethyl)phenyl] urea;

3-[(3R)-1-[6-(2-methanesulfonamidophenyl)pyridin-3-yl]-2-oxopiperidin-3-yl]-1-]4-(trifluoromethyl)phenyl] urea;

3-[(3R)-1-{2'-methanesulfonamido-[1,1'-biphenyl]-4-yl}-2-oxopiperidin-3-yl]-1-]6-(trifluoromethyl)pyridin-3-yl]urea;

1-(4-chloro-2-fluorophenyl)-3-[(3R)-1-]4-(2-methanesulfonamidopyridin-3-yl)phenyl]-2-oxopiperidin-3-yl] urea;

1-[(3R)-1-{2'-methanesulfonamido-[1,1'-biphenyl]-4-yl}-2-oxopiperidin-3-yl]-3-(5-methyl-1,2-oxazol-3-yl) urea;

3-[(3R)-1-(2-fluorophenyl)pyridin-2-yl]-2-oxopiperidin-3-yl]-1-]4-(trifluoromethyl)phenyl]urea;

1-(5-chloropyridin-2-yl)-3-[(3R)-1 42'-(methanesulfonamidomethyl)-[1,1'-biphenyl]-4-yl]-2-oxopiperidin-3-yl]urea;

1-(6-chloropyridin-3-yl)-3-[(3R)-1-[2'-(methanesulfonamidomethyl)-[1,1'-biphenyl]-4-yl]-2-oxopiperidin-3-yl]urea; and 3-[(3R)-1-{2'-methanesulfonamido-[1,1'-biphenyl]-4-yl}-2-oxopiperidin-3-yl]-1-(trifluoromethyl)pyridin-2-yl]urea;

or a pharmaceutically acceptable salt thereof.

12. A pharmaceutical composition comprising a compound of claim 1, or a pharmaceutically acceptable salt thereof, and a pharmaceutically acceptable carrier, diluent, or excipient.

* * * * *